(12) United States Patent
Kobori et al.

(10) Patent No.: US 9,029,552 B2
(45) Date of Patent: May 12, 2015

(54) TETRAZOYLOXIME DERIVATIVE AND PLANT DISEASE CONTROL AGENT

(71) Applicant: Nippon Soda Co., Ltd., Chiyoda-ku, Tokyo (JP)

(72) Inventors: Takeo Kobori, Inba-gun (JP); Hazumi Nomura, Odawara (JP); Ichirou Urihara, Tokyo (JP); Hiroyasu Hosokawa, Fujieda (JP); Atsunori Isshiki, Yokohama (JP); Syuichi Ito, Naka-gun (JP); Jun Inagaki, Naka-gun (JP); Kazushige Fujii, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 14/013,754

(22) Filed: Aug. 29, 2013

(65) Prior Publication Data
US 2014/0005385 A1    Jan. 2, 2014

Related U.S. Application Data

(62) Division of application No. 12/733,023, filed as application No. PCT/JP2008/064253 on Aug. 7, 2008, now abandoned.

(30) Foreign Application Priority Data

Aug. 8, 2007    (JP) .................. 2007-206297

(51) Int. Cl.
| | | |
|---|---|---|
| *C07D 401/12* | (2006.01) |
| *A01N 43/84* | (2006.01) |
| *A01N 43/713* | (2006.01) |
| *A01N 43/78* | (2006.01) |
| *C07D 417/12* | (2006.01) |

(52) U.S. Cl.
CPC .............. *A01N 43/84* (2013.01); *C07D 401/12* (2013.01); *A01N 43/713* (2013.01); *A01N 43/78* (2013.01); *C07D 417/12* (2013.01)

(58) Field of Classification Search
CPC ....................................................... C07D 401/12
USPC ........................................ 546/268.4; 514/340
See application file for complete search history.

(56) References Cited

U.S. PATENT DOCUMENTS

| 6,340,697 | B1 | 1/2002 | Kobori et al. |
| 7,183,299 | B2 | 2/2007 | Kobori et al. |
| 8,084,613 | B2 | 12/2011 | Kobori et al. |
| 2005/0070439 | A1 | 3/2005 | Kobori et al. |

FOREIGN PATENT DOCUMENTS

| EP | 1 184 382 A1 | 3/2002 |
| JP | 2001-055387 | 2/2001 |
| JP | 2003-137875 A | 5/2003 |
| JP | 2004-131392 A | 4/2004 |
| JP | 2004-131416 | 4/2004 |

OTHER PUBLICATIONS

International Search Report dated Jul. 15, 2008 in PCT/JP2008/058844.
Office Action dated Oct. 22, 2010, in U.S. Appl. No. 12/599,854.
Silverman, Richard B., *The Organic Chemistry of Drug Design and Drug Action*, $2^{nd}$ Ed., 2004, Elsevier, 29-32.
International Search Report issued for International Application No. PCT/JP2008/064253 on Sep. 9, 2008 with translation.

*Primary Examiner* — Patricia L Morris
(74) *Attorney, Agent, or Firm* — Foley & Lardner LLP

(57) ABSTRACT

According to the present invention, a tetrazoyloxime derivative and a salt thereof, which are excellent in a control effect against plant disease injury, and a plant disease controlling agent containing the same as an active ingredient are provided.

2 Claims, No Drawings

TETRAZOYLOXIME DERIVATIVE AND PLANT DISEASE CONTROL AGENT

CROSS-REFERENCE TO RELATED APPLICATIONS

This application is a Divisional of U.S. application Ser. No. 12/733,023, which is the U.S. National Stage application of PCT/JP2008/064253, filed Aug. 7, 2008, which claims priority from Japanese application no. JP 2007-206297, filed Aug. 8, 2007.

TECHNICAL FIELD

The present invention relates to a novel tetrazoyloxime derivative, and a plant disease control agent containing the same as an active ingredient.

This application claims priority on Japanese Patent Application No. 2007-206297 filed on Aug. 8, 2007, the disclosure of which is incorporated by reference herein.

BACKGROUND ART

In the cultivation of agricultural and horticultural crops, a large number of controlling agents have been used against crop injury. However, many of them are hardly satisfactory as controlling agents because of insufficient control efficacy, restrictions on their use due to appearance of pathogenic fungi having drug resistance, phytotoxicity or pollution on plants, or strong toxicity on humans, domestic animals and fishes. Therefore, there has been required to develop plant disease controlling agents applicable safely and having less of the drawbacks mentioned above.

Relating to the present invention, Patent Documents 1 to 3 disclose tetrazoyloxime derivatives having a structure similar to that of the compounds of the present invention.

[Patent Document 1]
Japanese Unexamined Patent Application, First Publication No. 2004-131416
[Patent Document 2]
Japanese Unexamined Patent Application, First Publication No. 2004-131392
[Patent Document 3]
Japanese Unexamined Patent Application, First Publication No. 2003-137875

DISCLOSURE OF THE INVENTION

Problems to be Solved by the Invention

However, even the compounds described in these patent documents do not have necessarily a sufficient control effect.

Under these circumstances of prior arts, the present invention has been made and an object thereof is to provide a tetrazoyloxime derivative or a salt thereof, which is excellent in a control effect against plant disease injury, and a plant disease controlling agent containing at least one kind of them as an active ingredient.

Means for Solving the Problems

The present inventors have synthesized a large number of tetrazoyloxime derivatives and intensively studied about bioactivity thereof so as to achieve the above object, and found that the tetrazoyloxime derivative represented by formula (1) shown below and a salt thereof exhibit an excellent control effect against plant disease injury, and are applicable safely without causing phytotoxicity against useful plants. Thus, the present invention has been completed.

According to a first aspect of the present invention, tetrazoyloxime derivatives of [1] to [3] shown below, or salts thereof are provided.

[1] A tetrazoyloxime derivative represented by formula (1):

$$\text{(1)}$$

wherein X represents a halogen atom, a $C_{1-8}$ alkyl group, a $C_{1-8}$ alkoxy group, cyano group, a $C_{1-8}$ alkylsulfonyl group, nitro group, a $C_{1-8}$ haloalkyl group, or an unsubstituted or substituted aryl group;
n1 represents any one of integers of 0 to 5, and
when n1 is 2 or more, X(s) may be the same or different with each other;
A represents a tetrazoyl group represented by formula (2):

$$\text{(2)}$$

(in which Y represents a $C_{1-8}$ alkyl group), or a tetrazoyl group represented by formula (3):

$$\text{(3)}$$

(in which Y is the same as defined above); and
Het represents a pyridyl group represented by formula (4):

$$\text{(4)}$$

(in which R represents a halogen atom, a cyano group, a nitro group, a hydroxyl group, a thiol group, a formyl group, a carboxyl group, an unsubstituted or substituted amino group, an unsubstituted or substituted $C_{1-8}$ alkyl group, an unsubstituted or substituted $C_{2-8}$ alkenyl group, an unsubstituted or substituted $C_{2-8}$ alkynyl group, an unsubstituted or substituted aryl group, an unsubstituted or substituted heterocyclic group, $OR^1$, $S(O)_m R^1$, $COR^1$, or $CO_2 R^1$,
$R^1$ represents an unsubstituted or substituted amino group, an unsubstituted or substituted $C_{1-8}$ alkyl group, an unsubstituted or substituted $C_{3-8}$ cycloalkyl group, an unsubstituted or substituted $C_{2-8}$ alkenyl group, an unsubstituted or substituted $C_{2-8}$ alkynyl group, or an unsubstituted or substituted aryl group, m represents any one of integers of 0 to 2,
n2 represents any one of integers of 0 to 3, and
when n2 is 2 or more, plural R(s) may be the same or different from each other,
when n2 is 0, Z represents a group represented by formula: $Q^1C(=O)NH$— (in which $Q^1$ represents a $C_{1-8}$ haloalkyl group, a $C_{2-8}$ haloalkenyl group, a $C_{2-8}$ alkynyl group, a $C_{2-8}$ haloalkynyl group, a $C_{1-8}$ haloalkoxy group, a $C_{2-8}$ alkenyloxy group, a $C_{2-8}$ haloalkenyloxy group, a $C_{2-8}$ alkynyloxy group, a $C_{2-8}$ haloalkynyloxy group, a $C_{1-8}$ alkoxy group substituted with an alkoxycarbonylamino group, a $C_{1-8}$ alkoxy group substituted with a $C_{3-8}$ cycloalkyl group, a $C_{1-8}$ branched alkoxy group substituted with an unsubstituted aryl group, a $C_{1-8}$ alkoxy group substituted with substituted aryl, a $C_{1-8}$ alkoxy group substituted with an unsubstituted or substituted heterocyclic group, a $C_{1-8}$ alkoxy group substituted with an unsubstituted or substituted $C_{1-8}$ alkoxy group, a $C_{1-8}$ alkoxy group substituted with an unsubstituted or substituted aryloxy group, an $C_{1-8}$ alkoxy group substituted with an unsubstituted or substituted aralkyloxy group, a $C_{2-8}$ alkynyloxy group substituted with an unsubstituted or substituted aryl group, a $C_{1-8}$ alkoxy group substituted with an unsubstituted or substituted $C_{1-8}$ alkylthio group, a $C_{1-8}$ alkoxy group substituted with an unsubstituted or substituted arylthio group, a $C_{1-8}$ alkoxy group substituted with an unsubstituted or substituted $C_{1-8}$ alkylsulfinyl group, a $C_{1-8}$ alkoxy group substituted with an unsubstituted or substituted arylsulfinyl group, a $C_{1-8}$ alkoxy group substituted with an unsubstituted or substituted $C_{1-8}$ alkylsulfonyl group, a $C_{1-8}$ alkoxy group substituted with an unsubstituted or substituted arylsulfonyl group, a $C_{1-8}$ alkoxy group substituted with an amino group which is unsubstituted or substituted with an (unsubstituted or substituted alkyl group), a $C_{1-8}$ alkoxy group which is substituted with an amino group substituted with an (unsubstituted or substituted aralkyl group), an unsubstituted or substituted aryloxy group, a $C_{1-8}$ alkyl group substituted with a carboxyl group, a $C_{1-8}$ alkyl group substituted with an amino group which is unsubstituted or substituted with an (unsubstituted or substituted aralkyl group), a $C_{1-8}$ alkyl group substituted with an amino group which is substituted with an (unsubstituted or substituted alkyl group), a $C_{1-8}$ alkyl group substituted with an unsubstituted or substituted aryloxy group, a $C_{1-8}$ alkyl group substituted with an acyl group, or a $C_{1-8}$ alkyl group substituted with an unsubstituted or substituted heterocyclicoxy group),
when n2 is 1 and R is a halogen atom, Z represents a hydrogen atom, an amino group, or a group represented by formula: $Q^2C(=O)NH$— (in which $Q^2$ represents a hydrogen atom, a $C_{1-8}$ haloalkyl group, a $C_{2-8}$ alkenyl group, a $C_{2-8}$ haloalkenyl group, a $C_{2-8}$ alkynyl group, a $C_{2-8}$ haloalkynyl group, a $C_{1-8}$ alkoxy group, a $C_{1-8}$ haloalkoxy group, a $C_{2-8}$ alkenyloxy group, a $C_{2-8}$ haloalkenyloxy group, a $C_{2-8}$ alkynyloxy group, a $C_{2-8}$ haloalkynyloxy group, a $C_{3-8}$ cycloalkyl group, a $C_{3-8}$ cycloalkyloxy group, a $C_{1-8}$ alkylamino group, a $C_{1-8}$ alkoxy group substituted with an unsubstituted or substituted amino group, a $C_{1-8}$ alkoxy group substituted with a $C_{3-8}$ cycloalkyl group, an unsubstituted or substituted aralkyloxy group, a $C_{1-8}$ alkoxy group substituted with an unsubstituted or substituted heterocyclic group, a $C_{1-8}$ alkoxy group substituted with an unsubstituted or substituted $C_{1-8}$ alkoxy group, a $C_{1-8}$ alkoxy group substituted with an unsubstituted or substituted aryloxy group, a $C_{1-8}$ alkoxy group substituted with an unsubstituted or substituted aralkyloxy group, a $C_{2-8}$ alkynyloxy group substituted with an unsubstituted or substituted aryl group, a $C_{1-8}$ alkoxy group substituted with an unsubstituted or substituted $C_{1-8}$ alkylthio group, a $C_{1-8}$ alkoxy group substituted with an unsubstituted or substituted arylthio group, a $C_{1-8}$ alkoxy group substituted with an unsubstituted or substituted $C_{1-8}$ alkylsulfinyl group, a $C_{1-8}$ alkoxy group substituted with an unsubstituted or substituted arylsulfinyl group, a $C_{1-8}$ alkoxy group substituted with an unsubstituted or substituted $C_{1-8}$ alkylsulfonyl group, a $C_{1-8}$ alkoxy group substituted with an unsubstituted or substituted arylsulfonyl group, an unsubstituted or substituted aryloxy group, a $C_{1-8}$ alkyl group substituted with a carboxyl group, a $C_{1-8}$ alkyl group substituted with an unsubstituted or substituted amino group, a $C_{1-8}$ alkyl group substituted with an unsubstituted or substituted aryloxy group, a $C_{1-8}$ alkyl group substituted with an unsubstituted or substituted $C_{1-8}$ alkylthio group, a $C_{1-8}$ alkyl group substituted with an unsubstituted or substituted alkoxy group, a $C_{1-8}$ alkyl group substituted with an unsubstituted or substituted heterocyclicoxy group), when n2 is 1 or more and at least one R is a cyano group, a nitro group, a hydroxyl group, a thiol group, a formyl group, a carboxyl group, an unsubstituted or substituted amino group, an unsubstituted or substituted $C_{1-8}$ alkyl group, an unsubstituted or substituted $C_{2-8}$ alkenyl group, an unsubstituted or substituted $C_{2-8}$ alkynyl group, an unsubstituted or substituted aryl group, an unsubstituted or substituted heterocyclic group, $OR^1$, $S(O)_mR^1$, $COR^1$, or $CO_2R^1$, or when n2 is 2 or more and at least two R(s) are halogen atoms, Z represents a hydrogen atom, an amino group, or a group represented by formula: $Q^3C(=O)NH$— (in which $Q^3$ represents a hydrogen atom, a $C_{1-8}$ alkyl group, a $C_{1-8}$ haloalkyl group, a $C_{2-8}$ alkenyl group, a $C_{2-8}$ haloalkenyl group, a $C_{2-8}$ alkynyl group, a $C_{2-8}$ haloalkynyl group, a $C_{1-8}$ alkoxy group, a $C_{1-8}$ haloalkoxy group, a $C_{2-8}$ alkenyloxy group, a $C_{2-8}$ haloalkenyloxy group, a $C_{2-8}$ alkynyloxy group, a $C_{2-8}$ haloalkynyloxy group, a $C_{3-8}$ cycloalkyl group, a $C_{3-8}$ cycloalkyloxy group, a $C_{1-8}$ alkylamino group, a $C_{1-8}$ alkoxy group substituted with an unsubstituted or substituted amino group, a $C_{1-8}$ alkoxy group substituted with a $C_{3-8}$ cycloalkyl group, an unsubstituted or substituted aralkyloxy group, a $C_{1-8}$ alkoxy group substituted with an unsubstituted or substituted heterocyclic group, a $C_{1-8}$ alkoxy group substituted with an unsubstituted or substituted $C_{1-8}$ alkoxy group, a $C_{1-8}$ alkoxy group substituted with an unsubstituted or substituted aryloxy group, a $C_{1-8}$ alkoxy group substituted with an unsubstituted or substituted aralkyloxy group, a $C_{2-8}$ alkynyloxy group substituted with an unsubstituted or substituted aryl group, a $C_{1-8}$ alkoxy group substituted with an unsubstituted or substituted $C_{1-8}$ alkylthio group, a $C_{1-8}$ alkoxy group substituted with a substituted or unsubstituted arylthio group, a $C_{1-8}$ alkoxy group substituted with an unsubstituted or substituted $C_{1-8}$ alkylsulfinyl group, a $C_{1-8}$ alkoxy group substituted with an unsubstituted or substituted arylsulfinyl group, a $C_{1-8}$ alkoxy group substituted with an unsubstituted or substituted $C_{1-8}$ alkylsulfonyl group, a $C_{1-8}$ alkoxy group substituted with an unsubstituted or substituted arylsulfonyl group, an unsubstituted or substituted aryloxy group, a $C_{1-8}$ alkyl group substituted with a carboxyl group, a $C_{1-8}$ alkyl group substituted with an unsubstituted or substituted amino group, a $C_{1-8}$ alkyl group substituted with an unsubstituted or substituted aryloxy group, a $C_{1-8}$ alkyl group substituted with an unsubstituted or substituted $C_{1-8}$ alkylthio group, a $C_{1-8}$ alkyl group substituted with an unsubstituted or substituted alkoxy group, an alkyl group substituted with an acyl group, or a $C_{1-8}$ alkyl group substituted with an unsubstituted or substituted heterocyclicoxy group), or a thiazoyl group represented by formula (5):

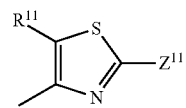

(5)

(in which $R^{11}$ represents a hydrogen atom, a halogen atom, a cyano group, a nitro group, a hydroxyl group, a thiol group, a formyl group, a carboxyl group, an unsubstituted or substituted amino group, an unsubstituted or substituted $C_{1-8}$ alkyl group, an unsubstituted or substituted $C_{2-8}$ alkenyl group, an unsubstituted or substituted $C_{2-8}$ alkynyl group, an unsubstituted or substituted aryl group, an unsubstituted or substituted heterocyclic group, $OR^1$, $S(O)_mR^1$, $COR^1$, or $CO_2R^1$, $R^1$ is the same as defined above, when $R^{11}$ is a hydrogen atom, $Z^{11}$ represents a group represented by formula: $Q'C(=O)NH—$ (in which $Q^1$ is the same as defined above), when $R^{11}$ is a halogen atom, $Z^{11}$ represents a hydrogen atom, an amino group, or a group represented by formula: $Q^2C(=O)NH—$ (in which $Q^2$ is the same as defined above), and when $R^{11}$ is a cyano group, a nitro group, a hydroxyl group, a thiol group, a formyl group, a carboxyl group, an unsubstituted or substituted amino group, an unsubstituted or substituted $C_{1-8}$ alkyl group, an unsubstituted or substituted $C_{2-8}$ alkenyl group, an unsubstituted or substituted $C_{2-8}$ alkynyl group, an unsubstituted or substituted aryl group, an unsubstituted or substituted heterocyclic group, $OR^1$, $S(O)_mR^1$, $COR^1$, or $CO_2R^1$, represents a hydrogen atom, an amino group, or a group represented by formula: $Q^3C(=O)NH—$ (in which $Q^3$ is the same as defined above), and a salt thereof.

[2] The tetrazoyloxime derivative according to [1], wherein n1 is 0, or X is halogen atom, and a salt thereof.

[3] The tetrazoyloxime derivative according to [1] or [2], wherein Y is a methyl group, and a salt thereof.

According to a second aspect of the present invention, a plant disease controlling agent including the tetrazoyloxime derivative according to any one of [1] to [3] or a salt thereof as an active ingredient is provided.

Effects of the Invention

According to the present invention, a tetrazoyloxime derivative which is excellent in a control effect against plant disease injury, or a salt thereof, and a plant disease controlling agent containing the same as an active ingredient are provided.

BEST MODE FOR CARRYING OUT THE INVENTION

The present invention will be explained in detail by itemizing into 1) a tetrazoyloxime derivative and a salt thereof, and 2) a plant disease controlling agent.

1) Tetrazoyloxime Derivative and a Salt Thereof

The first aspect of the present invention is directed to a tetrazoyloxime derivative represented by formula (1) shown above, and a salt thereof.

In formula (1) shown above, X represents a halogen atom, a $C_{1-8}$ alkyl group, a $C_{1-8}$ alkoxy group, a cyano group, a $C_{1-8}$ alkylsulfonyl group, a nitro group, a $C_{1-8}$ haloalkyl group, or an unsubstituted or substituted aryl group.

Specific examples of the halogen atom for X include a fluorine atom, a chlorine atom, a bromine atom, and an iodine atom.

Specific examples of the $C_{1-8}$ alkyl group include a methyl group, an ethyl group, an n-propyl group, an i-propyl group, an n-butyl group, an i-butyl group, an s-butyl group, a t-butyl group, an n-pentyl group, and an n-hexyl group.

Specific examples of the $C_{1-8}$ alkoxy group include a methoxy group, an ethoxy group, an n-propoxy group, an i-propoxy group, an n-butoxy group, an i-butoxy group, an s-butoxy group, a t-butoxy group, and an n-hexyloxy group.

Specific examples of the $C_{1-8}$ alkylsulfonyl group include a methylsulfonyl group, an ethylsulfonyl group, an n-propylsulfonyl group, an isopropylsulfonyl group, and a t-butylsulfonyl group.

Specific examples of the $C_{1-8}$ haloalkyl group include a fluoromethyl group, a chloromethyl group, a bromomethyl group, a difluoromethyl group, a dichloromethyl group, a trifluoromethyl group, a trichloromethyl group, a trifluoroethyl group, a pentafluoroethyl group, a 3,3,3,2,2-pentafluoropropyl group, and a 2,2,2-trifluoro-1-trifluoromethylethyl group.

An aryl group an unsubstituted or substituted aryl group means a monocyclic or polycyclic aryl group, and the polycyclic aryl group includes, in addition to a completely unsaturated group, a partially unsaturated group. Specifically, a phenyl group, a 1-naphthyl group, a 2-naphthyl group, an azulenyl group, an indanyl group, and a tetralinyl group are exemplified, and a $C_{6-10}$ aryl group is preferred.

The substituent of the aryl group of the unsubstituted or substituted aryl group is not particularly limited as long as it is chemically acceptable. Specific examples of the substituent include substituents shown below:

(1) halogen atoms such as a fluorine atom, a chlorine atom, a bromine atom, and an iodine atom, (2) alkyl groups such as a methyl group, an ethyl group, an n-propyl group, an i-propyl group, an n-butyl group, an s-butyl group, an i-butyl group, a t-butyl group, an n-pentyl group, and an n-hexyl group, (3) cycloalkyl groups such as a cyclopropyl group, a cyclobutyl group, a cyclopentyl group, a cyclohexyl group, and a cycloheptyl group, (4) alkoxy groups such as a methoxy group, an ethoxy group, an n-propoxy group, an isopropoxy group, an n-butoxy group, an i-butoxy group, an s-butoxy group, and a t-butoxy group, (5) alkenyl groups such as a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group, (6) cycloalkenyl groups such as a 2-cyclopropenyl group, a 2-cyclopentenyl group, a 3-cyclohexenyl group, and a 4-cyclooctenyl group, (7) alkenyloxy groups such as a vinyloxy group, an allyloxy group, a 1-propenyloxy group, a 2-butenyloxy group, a (8) alkynyl groups such as ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, and a 1,1-dimethyl-2-butynyl group, (9) alkynyloxy groups such as an ethynyloxy group and a propargyloxy group,

(10) aryl groups such as a phenyl group, a 1-naphthyl group, and a 2-naphthyl group,

(11) aryloxy groups such as a phenoxy group and a 1-naphthoxy group,

(12) aralkyl groups such as a benzyl group and a phenethyl group,

(13) aralkyloxy groups such as a benzyloxy group and a phenethyloxy group,

(14) acyl groups such as a formyl group, an acetyl group, a propionyl group, a benzoyl group, a cyclohexylcarbonyl group, and a phthaloyl group,

(15) alkoxycarbonyl groups such as a methoxycarbonyl group, an ethoxycarbonyl group, an n-propoxycarbonyl group, an isopropoxycarbonyl group, an n-butoxycarbonyl group, and a t-butoxycarbonyl group,

(16) carboxyl groups,

(17) hydroxyl groups,

(18) haloalkyl groups such as a chloromethyl group, a chloroethyl group, a 1,2-dichloro-n-propyl group, a 1-fluoro-n-butyl group, a perfluoro-n-pentyl group, a haloalkoxy groups such as 2-chloro-n-propoxy group, a 2,3-dichlorobutoxy group, and a trifluoromethoxy group,

(19) haloalkenyl groups such as a 2-chloro-1-propenyl group and a 2-fluoro-1-butenyl group,

(20) haloalkynyl groups such as a 4,4-dichloro-1-butynyl group, a 4-fluoro-1-pentynyl group, and a 5-bromo-2-pentynyl group,

(21) haloalkenyloxy groups such as a 2-chloro-1-propenyloxy group and a 3-bromo-2-butenyloxy group,

(22) haloalkynyl groups such as a 3-chloro-propargyl group and a 3-iodo-propargyl group,

(23) haloalkynyloxy groups such as a 3-chloro-propargyloxy group and a 3-iodo-propargyloxy group,

(24) haloaryl groups such as a 4-chlorophenyl group, a 4-fluorophenyl group, and a 2,4-dichlorophenyl group,

(25) haloaryloxy groups such as a 4-fluorophenoxy group and a 4-chloro-1-naphthoxy group,

(26) halogen-substituted acyl groups such as a chloroacetyl group, a trifluoroacetyl group, a trichloroacetyl group, and a 4-chlorobenzoyl group,

(27) alkoxyalkyl groups such as a methoxymethyl group, an ethoxymethyl group, a 1-ethoxyethyl group, and a 2-ethoxyethyl group,

(28) alkoxyalkoxy groups such as a methoxymethoxy group, an ethoxymethoxy group, a 1-ethoxyethoxy group, and a 2-ethoxyethoxy group,

(29) cyano groups,

(30) isocyano groups,

(31) nitro groups,

(32) isocyanato groups,

(33) cyanato groups,

(34) amino groups,

(35) alkylamino groups such as a methylamino group, a dimethylamino group, and a diethylamino group,

(36) arylamino groups such as an anilino group, a naphthylamino group, and an anthranyl amino group,

(37) aralkylamino groups such as a benzylamino group and a phenethylamino group,

(38) alkylsulfonylamino groups such as a methylsulfonylamino group, an ethylsulfonylamino group, an n-propylsulfonylamino group, an isopropylsulfonylamino group, and an n-butylsulfonylamino group,

(39) arylsulfonylamino groups such as a phenylsulfonylamino group,

(40) heteroarylsulfonylamino groups such as a piperazinylsulfonylamino group

(41) acylamino groups such as a formylamino group, an acetylamino group, a propanoylamino group, a butyrylamino group, an isopropylcarbonylamino group, and a benzoylamino group

(42) alkoxycarbonylamino groups such as a methoxycarbonylamino group and an ethoxycarbonylamino group,

(43) haloalkylsulfonylamino groups such as a fluoromethylsulfonylamino group, a chloromethylsulfonylamino group, a bromomethylsulfonylamino group, a difluoromethylsulfonylamino group, a dichloromethylsulfonylamino group, a 1,1-difluoroethylsulfonylamino group, a trifluoromethylsulfonylamino group, a 2,2,2-trifluoroethylsulfonylamino group, and a pentafluorosulfonylamino group,

(44) bis(alkylsulfonyl)amino groups such as a bis(methylsulfonyl)amino group, a bis(ethylsulfonyl)amino group, an (ethylsulfonyl)(methylsulfonyl)amino group, a bis(n-propylsulfonyl)amino group, a bis(isopropylsulfonyl)amino group, a bis(n-butylsulfonyl)amino group, and a bis(t-butylsulfonyl)amino group,

(45) bis(haloalkylsulfonyl)amino groups such as a bis(fluoromethylsulfonyl)amino group, a bis(chloromethylsulfonyl)amino group, a bis(bromomethylsulfonyl)amino group, a bis(dichloromethylsulfonyl)amino group, a bis(1,1-difluoroethylsulfonyl)amino group, a bis(trifluoromethylsulfonyl)amino group, a bis(2,2,2-trifluoroethyl)amino group, and a bis(pentafluoroethylsulfonyl)amino group,

(46) unsubstituted or substituted hydrazino groups such as a hydrazino group, an N'-phenylhydrazino group, an N'-methoxycarbonylhydrazino group, an N'-acetylhydrazino group, and an N'-methylhydrazino group,

(47) unsubstituted or substituted aminocarbonyl groups such as an aminocarbonyl group, a dimethylaminocarbonyl group, a phenylaminocarbonyl group, and an N-phenyl-N-methylcarbonyl group,

(48) unsubstituted or substituted hydrazinocarbonyl groups such as a hydrazinocarbonyl group, an N'-methylhydrazinocarbonyl group, and an N'-phenylhydrazinocarbonyl group,

(49) unsubstituted or substituted iminoalkyl groups such as an N-methyliminomethyl group, a 1-N-phenyliminoethyl group, an N-hydroxyiminomethyl group, and an N-methoxyiminomethyl group,

(50) thiol groups,

(51) isothiocyanato groups,

(52) thiocyanato groups,

(53) alkylthio groups such as a methylthio group, an ethylthio group, an n-propylthio group, an isopropylthio group, an n-butylthio group, an isobutylthio group, an s-butylthio group, and a t-butylthio group,

(54) alkenylthio groups such as vinylthio group, an allylthio group,

(55) alkynylthio groups such as an ethynylthio group and a propargylthio group,

(56) arylthio groups such as a phenylthio group and a naphthylthio group,

(57) heteroarylthio groups such as 2-piperidylthio group, a 3-pyridazylthio group,

(58) aralkylthio groups such as a benzylthio group and a phenethylthio group,

(59) heteroarylalkylthio groups such as a 2-pyridylmethylthio group and a 2-furylmethylthio group,

(60) alkylthiocarbonyl groups such as a methylthiocarbonyl group, an ethylthiocarbonyl group, an n-propylthiocarbonyl group, an isopropylthiocarbonyl group, an n-butylthiocarbonyl group, an isobutylthiocarbonyl group, an s-butylthiocarbonyl group, and a t-butylthiocarbonyl group,

(61) alkylthioalkyl groups such as a methylthiomethyl group and a 1-methylthioethyl group,

(62) arylthioalkyl groups such as a phenylthiomethyl group and a 1-phenylthioethyl group,

(63) alkylthioalkoxy groups such as a methylthiomethoxy group and a 1-methylthioethoxy group,

(64) arylthioalkoxy groups such as a phenylthiomethoxy group and a 1-phenylthioethoxy group,

(65) alkylsulfinyl groups such as a methylsulfinyl group, an ethylsulfinyl group, and a t-butylsulfenyl group,
(66) alkenylsulfinyl groups such as an allylsulfinyl group,
(67) alkynylsulfinyl groups such as a propargylsulfinyl group,
(68) arylsulfinyl groups such as a phenylsulfinyl group,
(69) heteroarylsulfinyl groups such as a 2-pyridylsulfinyl group and a 3-pyridylsulfinyl group,
(70) aralkylsulfinyl groups such as a benzylsulfinyl group and a phenethylsulfinyl group,
(71) heteroarylalkylsulfenyl groups such as a 2-pyridylmethylsulfinyl group and a 3-pyridylmethylsulfinyl group,
(72) alkylsulfonyl groups such as a methylsulfonyl group, an ethylsulfonyl group, and a t-butylsulfonyl group,
(73) alkenylsulfonyl groups such as an allylsulfonyl group,
(74) alkynylsulfonyl groups such as a propargylsulfonyl group,
(75) arylsulfonyl groups such as a phenylsulfonyl group,
(76) heteroarylsulfonyl groups such as 2-pyridylsulfonyl group and a 3-pyridylsulfonyl group,
(77) aralkylsulfonyl groups such as a benzylsulfonyl group and a phenethylsulfonyl group,
(78) heteroarylalkylsulfonyl groups such as a 2-pyridylmethylsulfonyl group and a 3-pyridylmethylsulfonyl group,
(79) unsaturated 5-membered heterocyclic groups such as a furan-2-yl group, a furan-3-yl group, a thiophen-2-yl group, a thiophen-3-yl group, a pyrrol-2-yl group, a pyrrol-3-yl group, an oxazol-2-yl group, an oxazol-4-yl group, an oxazol-5-yl group, a thiazol-2-yl group, a thiazol-4-yl group, a thiazol-5-yl group, an isooxazol-3-yl group, an isooxazol-4-yl group, an isooxazol-5-yl group, an isothiazol-3-yl group, an isothiazol-4-yl group, an isothiazol-5-yl group, an imidazol-2-yl group, an imidazol-4-yl group, an imidazol-5-yl group, a pyrazol-3-yl group, a pyrazol-4-yl group, a pyrazol-5-yl group, a 1,3,4-oxadiazol-2-yl group, a 1,3,4-thiadiazol-2-yl group, a 1,2,3-triazol-4-yl group, a 1,2,4-triazol-3-yl group, and a 1,2,4-triazol-5-yl group,
(80) unsaturated 6-membered heterocyclic groups such as a pyridin-2-yl group, a pyridin-3-yl group, a pyridin-4-yl group, a 5-chloro-3-pyridyl group, a 3-trifluoromethyl-2-pyridyl group, a pyridazin-3-yl group, a pyridazin-4-yl group, a pyrazin-2-yl group, a pyrimidin-5-yl group, a 1,3,5-triazin-2-yl group, and a 1,2,4-triazin-3-yl group,
(81) saturated or partially unsaturated heterocyclic groups such as a tetrahydrofuran-2-yl group, a tetrahydropyran-4-yl group, a piperidin-3-yl group, a pyrrolidin-2-yl group, a morpholino group, a piperidino group, an N-methylpiperazino group, and an oxazolin-2-yl group,
(82) heterocyclicoxy groups such as a 2-pyridyloxy group and a 3-isooxazolyloxy group,
(83) heteroarylalkyl groups such as a 2-pyridylmethyl group and a 3-pyridylmethyl group, and
(84) heteroarylalkoxy groups such as a 2-pyridylmethoxy group and a 3-pyridylmethoxy group.

These substituents exemplified in (1) to (84) can also be substituted with those exemplified in (1) to (84).

Specific examples of the substituted aryl group include a 4-fluorophenyl group, a 2,4-dichlorophenyl group, a 3,5-dichlorophenyl group, a 2,6-difluorophenyl group, a 4-methoxyphenyl group, and a 3,4-dimethoxyphenyl group.

Among these, X is preferably a halogen atom.

n1 represents any one of integers of 0 to 5, and preferably any one of integers of 0 to 3.

When n1 is 2 or more, X(s) may be the same or different with each other.

A represents a tetrazoyl group represented by formula (2) or formula (3), and preferably formula (2).

In formulas (2) and (3), Y represents a $C_{1-8}$ alkyl group. Examples of the $C_{1-8}$ alkyl group include a methyl group, an ethyl group, an n-propyl group, an i-propyl group, an n-butyl group, an i-butyl group, an s-butyl group, a t-butyl group, an n-pentyl group, and an n-hexyl group.

Among these, Y is preferably a $C_{1-3}$ alkyl group, and particularly preferably a methyl group.

Het represents a pyridyl group represented by formula (4) or a thiazolyl group represented by formula (5).

In formulas (4) and (5), R represents a halogen atom, a cyano group, a nitro group, a hydroxyl group, a thiol group, a formyl group, a carboxyl group, an unsubstituted or substituted amino group, an unsubstituted or substituted $C_{1-8}$ alkyl group, an unsubstituted or substituted $C_{2-8}$ alkenyl group, an unsubstituted or substituted $C_{2-8}$ alkynyl group, an unsubstituted or substituted aryl group, an unsubstituted or substituted heterocyclic group, $OR^1$, $S(O)_m R^1$, $COR^1$, or $CO_2R^1$.

Specific examples of the halogen atom, the $C_{1-8}$ alkyl group of the unsubstituted or substituted $C_{1-8}$ alkyl group, and the aryl group of the unsubstituted or substituted aryl group for R are the same as those for X.

Specific examples of the $C_{2-8}$ alkenyl group of the unsubstituted or substituted $C_{2-8}$ alkenyl group for R include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group.

Specific examples of the $C_{2-8}$ alkynyl group of the unsubstituted or substituted $C_{2-8}$ alkynyl group for R include an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, and a 1,1-dimethyl-2-butynyl group.

Specific examples of the heterocyclic group of the unsubstituted or substituted heterocyclic group for R include unsaturated 5-membered heterocyclic groups such as a furan-2-yl group, a furan-3-yl group, a thiophen-2-yl group, a thiophen-3-yl group, a pyrrol-2-yl group, a pyrrol-3-yl group, an oxazol-2-yl group, an oxazol-4-yl group, an oxazol-5-yl group, a thiazol-2-yl group, a thiazol-4-yl group, a thiazol-5-yl group, an isooxazol-3-yl group, an isooxazol-4-yl group, an isooxazol-5-yl group, an isothiazol-3-yl group, an isothiazol-4-yl group, an isothiazol-5-yl group, an imidazol-2-yl group, an imidazol-4-yl group, an imidazol-5-yl group, a pyrazol-3-yl group, a pyrazol-4-yl group, a pyrazol-5-yl group, a 1,3,4-oxadiazol-2-yl group, a 1,3,4-thiadiazol-2-yl group, a 1,2,3-triazol-4-yl group, a 1,2,4-triazol-3-yl group, and a 1,2,4-triazol-5-yl group; unsaturated 6-membered heterocyclic groups such as a pyridin-2-yl group, a pyridin-3-yl group, a pyridin-4-yl group, a 5-chloro-3-pyridyl group, a 3-trifluoromethyl-2-pyridyl group, a pyridazin-3-yl group, a pyridazin-4-yl group, a pyrazin-2-yl group, a pyrimidin-5-yl group, a 1,3,5-triazin-2-yl group, and a 1,2,4-triazin-3-yl group; and saturated or partially unsaturated heterocyclic groups such as a tetrahydrofuran-2-yl group, a tetrahydropyran-4-yl group, a piperidin-3-yl group, a pyrrolidin-2-yl group, a morpholino group, a piperidino group, a piperazino group, an N-methylpiperazino group, an aziridino group, an azetidino group, a pyrrolidino group, a morpholino group, and an oxazolin-2-yl group.

As the substituent of the amino group, the $C_{1-8}$ alkyl group, the $C_{2-8}$ alkenyl group, the $C_{2-8}$ alkynyl group, the aryl group, and the heteroaryl group, for example, the same substituents as those of the aryl group for X can be exemplified in a chemically acceptable range.

Specific examples of the substituted amino group include a methylamino group, a dimethylamino group, a methylethylamino group, a diethylamino group, a t-butoxycarbonylmethylamino group, a t-butoxycarbonylamino group, an acetylmethylamino group, an acetylethylamino group, and a benzoylmethylamino group.

Specific examples of the substituted $C_{1-8}$ alkyl group include a chloromethyl group, a methoxymethyl group, a methylthiomethyl group, a methylsulfonylmethyl group, a dimethylaminomethyl group, a trichloromethyl group, a trifluoromethyl group, and a 2-chloroethyl group.

Specific examples of the substituted $C_{2-8}$ alkenyl group include a 2-chloroethenyl group, a 2-fluoroethenyl group, a 3,3,3-trifluoro-1-pentenyl group, a 1,2,2-trifluoroethenyl group, a 2,3,3-trifluoro-2-propenyl group, a 2,3,3-triiodo-2-propenyl group, and a 2-methoxyethenyl group.

Specific examples of the substituted $C_{2-8}$ alkynyl group include a 2-chloroethynyl group, a 2-fluoroethynyl group, a 3-fluoro-1-propynyl group, a 3,3,3-trifluoro-1-propynyl group, a 3-fluoro-2-propynyl group, and a 3-iodo-2-propynyl group.

Specific examples of the substituted aryl group include a 4-chlorophenyl group, a 2,4-dichlorophenyl group, a 3,4-dichlorophenyl group, a 4-trifluoromethylphenyl group, a 4-methoxyphenyl group, a 3,4-dimethoxyphenyl group, a 3,4-methylenedioxyphenyl group, a 4-trifluoromethoxyphenyl group, and a 4-methoxy-1-naphthyl group.

Specific examples of the substituted heterocyclic group include a 3-trifluoromethylpyridin-2-yl group, a 4-trifluoromethoxy-2-pyridyl group, a 3-methyl-1-pyrazolyl group, a 4-trifluoromethyl-1-imidazolyl group, and a 3,4-difluoropyrrolidino group.

$R^1$ of $OR^1$, $COR^1$, $S(O)_mR^1$, and $CO_2R^1$ for R represents an unsubstituted or substituted amino group, an unsubstituted or substituted $C_{1-8}$ alkyl group, an unsubstituted or substituted $C_{3-8}$ cycloalkyl group, an unsubstituted or substituted $C_{2-8}$ alkenyl group, an unsubstituted or substituted $C_{2-8}$ alkynyl group, an unsubstituted or substituted aryl group, or an unsubstituted or substituted heterocyclic group.

As specific examples of the unsubstituted or substituted amino group, the unsubstituted or substituted $C_{1-8}$ alkyl group, the unsubstituted or substituted $C_{2-8}$ alkenyl group, the unsubstituted or substituted $C_{2-8}$ alkynyl group, the unsubstituted or substituted aryl group, and the unsubstituted or substituted heterocyclic group, for example, the same groups as those for R can be exemplified.

Specific examples of the $C_{3-8}$ cycloalkyl group of the unsubstituted or substituted $C_{3-8}$ cycloalkyl group include a cyclopropyl group, a cyclobutyl group, a cyclopentyl group, a cyclohexyl group, and a cycloheptyl group.

Specific examples of the substituted $C_{3-8}$ cycloalkyl group include a 2-methylcyclopropyl group, a 2-chloro-cyclopropyl group, a 2-trifluoromethylcyclobutyl group, a 2,3,4-trifluorocyclopentyl group, and a 2,2,3,3-tetrafluorocyclopropyl group.

Specific examples of $OR^1$ include a methoxy group, an ethoxy group, an n-propoxy group, an i-propoxy group, an n-butoxy group, an s-butoxy group, an i-butoxy group, a t-butoxy group, a methoxymethoxy group, an ethoxymethoxy group, a 2-methoxyethoxy group, a 1-ethoxyethoxy group, a vinyloxy group, a 1-propenyloxy group, a 2-propenyloxy group, an ethynyloxy group, a 1-propynyloxy group, a 2-propynyloxy group, an aminooxy group, a methylaminooxy group, a diethylaminooxy group, a methoxycarbonylaminooxy group, a phenoxy group, a trichloromethoxy group, a trifluoromethoxy group, a difluoromethoxy group, a 2,2,2-trifluoroethoxy group, a pentafluoroethoxy group, and a 2-fluoroethoxy group.

Specific examples of $COR^1$ include an acetyl group, a benzoyl group, a propanoyl group, an i-propylcarbonyl group, a t-butylcarbonyl group, a cyclopropylcarbonyl group, a cyclobutylcarbonyl group, a cyclopentylcarbonyl group, a vinylcarbonyl group, a 1-propenylcarbonyl group, a 2-propenylcarbonyl group, an i-propenylcarbonyl group, a 1-propynylcarbonyl group, a 2-propynylcarbonyl group, a 3-butenylcarbonyl group, a methylaminocarbonyl group, a dimethylaminocarbonyl group, an N-methyl-N-ethylaminocarbonyl group, an aziridinocarbonyl group, an azetidinocarbonyl group, a pyrrolidinocarbonyl group, a piperidinocarbonyl group, a morpholinocarbonyl group, a piperazinocarbonyl group, and an N-methylpiperazinocarbonyl group.

Specific examples of $CO_2R^1$ include a methoxycarbonyl group, a trifluoromethoxycarbonyl group, a 1-pentenyloxycarbonyl group, a 2-propynyloxycarbonyl group, and a phenoxycarbonyl group.

Specific examples of $S(O)_mR^1$ for R include a dimethylaminothio group, a chloromethylthio group, a 3-butenylthio group, an ethynylthio group, a 3-methylphenylthio group, a methylsulfinyl group, an ethylsulfinyl group, a 1-butenylsulfinyl group, an n-hexylsulfinyl group, a 2,3-dimethylphenylsulfinyl group, a methylsulfonyl group, a dimethylaminosulfonyl group, an N-ethyl-N-methylaminosulfonyl group, an n-hexylsulfonyl group, a 2-methyl-2-butenylsulfonyl group, a 2-propynylsulfonyl group, a 2-naphthylsulfonyl group, a phenylsulfonyl group, a 2-nitrophenylsulfonyl group, and a p-tolylsulfonyl group.

Among these, a halogen atom, an unsubstituted or substituted amino group, a $C_{1-8}$ alkyl group, $OR_1$, and $SR_1$ are preferable, and an unsubstituted or substituted amino group, a $C_{1-8}$ alkyl group, $OR^1$, and $SR_1$ are more preferable.

An amino group and a dialkylamino group can be preferably exemplified as the unsubstituted or substituted amino group, a $C_{1-4}$ alkyl group can be preferably exemplified as the $C_{1-8}$ alkyl group, a $C_{1-4}$ alkoxy group can be preferably exemplified as $OR_1$, and a $C_{1-4}$ alkylthio group can be preferably exemplified as $SR_1$.

m represents any one of integers of 0 to 2.

n2 represents any one of integers of 0 to 3.

When n2 is 2 or more, plural R(s) may be the same or different from each other.

When n2 is 0, Z represents a group represented by formula: $Q^1C(=O)NH$— (in which $Q^1$ represents a $C_{1-8}$ haloalkyl group, a $C_{2-8}$ haloalkenyl group, a $C_{2-8}$ alkynyl group, a $C_{2-8}$ haloalkynyl group, a $C_{1-8}$ haloalkoxy group, a $C_{2-8}$ alkenyloxy group, a $C_{2-8}$ haloalkenyloxy group, a $C_{2-8}$ alkynyloxy group, a $C_{2-8}$ haloalkynyloxy group, a $C_{1-8}$ alkoxy group substituted with an alkoxycarbonylamino group, a $C_{1-8}$ alkoxy group substituted with a $C_{3-8}$ cycloalkyl group, a $C_{1-8}$ branched alkoxy group substituted with an unsubstituted aryl group, a $C_{1-8}$ alkoxy group substituted with a substituted aryl group, a $C_{1-8}$ alkoxy group substituted with a substituted or unsubstituted heterocyclic group, a $C_{1-8}$ alkoxy group substituted with an unsubstituted or substituted $C_{1-8}$ alkoxy group, a $C_{1-8}$ alkoxy group substituted with an unsubstituted or substituted aryloxy group, a $C_{1-8}$ alkoxy group substituted with an unsubstituted or substituted aralkyloxy group, a $C_{2-8}$ alkynyloxy group substituted with an unsubstituted or substituted aryl group, a $C_{1-8}$ alkoxy group substituted with an unsubstituted or substituted $C_{1-8}$ alkylthio group, a $C_{1-8}$ alkoxy group substituted with an unsubstituted or substituted arylthio group, a $C_{1-8}$ alkoxy group substituted with an unsubstituted or substituted $C_{1-8}$ alkylsulfinyl group, a $C_{1-8}$ alkoxy group substituted with an unsubstituted or substituted arylsulfinyl group, a $C_{1-8}$ alkoxy group substituted with an unsubstituted or substituted $C_{1-8}$ alkylsulfonyl group, a $C_{1-8}$ alkoxy group substituted with an unsubstituted or substituted arylsulfonyl group, a $C_{1-8}$ alkoxy group substituted with an amino group which is unsubstituted or substituted with an (unsubstituted or substituted alkyl group), a $C_{1-8}$ alkoxy group which is substituted with an amino group substituted with an (unsubstituted or substituted aralkyl group), an unsubstituted or substituted aryloxy group, a $C_{1-8}$ alkyl group substituted with a carboxyl group, a $C_{1-8}$ alkyl group substituted with an amino group which is unsubstituted or substituted with an (unsubstituted or substituted aralkyl group), a $C_{1-8}$ alkyl group substituted with an amino group which is substituted with an (unsubstituted or substituted alkyl group), a $C_{1-8}$ alkyl group substituted with an unsubstituted or substituted aryloxy group, a $C_{1-8}$ alkyl group substituted with an acyl group, or a $C_{1-8}$ alkyl group substituted with an unsubstituted or substituted heterocyclic group).

Specific examples of the $C_{1-8}$ haloalkyl group for $Q^1$ include a chloromethyl group, a chloroethyl group, a 1,2-dichloro-n-propyl group, a 1-fluoro-n-butyl group, and a perfluoro-n-pentyl group.

Specific examples of the $C_{2-8}$ haloalkenyl group for $Q^1$ include a 1-chlorovinyl group, a 2-bromovinyl group, a 3-fluoroallyl group, and a 2-fluorocrotyl group.

Specific examples of the $C_{2-8}$ alkynyl group for $Q^1$ include an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, and a 1,1-dimethyl-2-butynyl group.

Specific examples of the $C_{2-8}$ haloalkynyl group for $Q^1$ include a chloroethynyl group, a bromoethynyl group, an iodoethynyl group, a 3-chloro-1-propynyl group, a 3-chloro-1-butynyl group, and a 3-bromo-1-butynyl group.

Specific examples of the $C_{1-8}$ haloalkoxy group for $Q^1$ include a chloromethoxy group, a difluoromethoxy group, a trifluoromethoxy group, a 1,1-difluoroethoxy group, and a hexafluoroethoxy group.

Specific examples of the $C_{2-8}$ alkenyloxy group for $Q^1$ include an ethenyloxy group, a 1-propenyloxy group, a 1-methylvinyloxy group, an allyloxy group, a 1-methylallyloxy group, and a 2-butenyloxy group.

Specific examples of the $C_{2-8}$ haloalkenyloxy group for $Q^1$ include a 3-chloro-2-propenyloxy group, a 3,3-dichloro-2-propenyloxy group, a 4-chloro-2-butenyloxy group, a 4,4-dichloro-3-butenyloxy group, and a 4,4-difluoro-3-butenyloxy group.

Specific examples of the $C_{2-8}$ alkynyloxy group for $Q^1$ include a 2-propynyloxy group, a 2-butynyloxy group, and a 1-methyl-2-propynyloxy group.

Specific examples of the $C_{2-8}$ haloalkynyloxy group for $Q^1$ include a 2-chloroethynyloxy group, a 3-chloro-2-propynyloxy group, and a 3-fluoro-2-propynyloxy group.

Specific examples of the alkoxycarbonyl group of the $C_{1-8}$ alkoxy group substituted with an alkoxycarbonylamino group for $Q^1$ include a methoxycarbonyl group, an ethoxycarbonyl group, an n-propoxycarbonyl group, an isopropoxycarbonyl group, an n-butoxycarbonyl group, and a t-butoxycarbonyl group. As the $C_{1-8}$ alkoxy group, for example, the same alkoxy groups as those for X can be exemplified. Hereinafter, specific examples of the $C_{1-8}$ alkoxy group are the same specific examples. Specific examples of the $C_{1-8}$ alkoxy group substituted with an alkoxycarbonylamino group include an N-methoxycarbonylaminomethoxy group, an N-t-butoxycarbonylaminomethoxy group, a 2-(N-ethoxycarbonylamino)ethoxy group, and a 2-(N-t-butoxycarbonyl-N-benzylamino) ethoxy group.

Specific examples of the $C_{3-8}$ cycloalkyl group of the $C_{1-8}$ alkoxy group substituted with a $C_{3-8}$ cycloalkyl group for $Q^1$ include a cyclopropyl group, a cyclobutyl group, a cyclopentyl group, a cyclohexyl group, and a cycloheptyl group. Specific examples of the $C_{1-8}$ alkoxy group substituted with a $C_{3-8}$ cycloalkyl group include a cyclopropylmethoxy group, a 1-cyclopropyl-ethoxy group, a cyclohexylmethoxy group, and a 2-cyclohexyl-ethoxy group.

Specific examples of the $C_{1-8}$ branched alkoxy group substituted with an unsubstituted aryl group include a 1-phenylethoxy group, a 1-phenyl-1-methylethoxy group, and a 2-phenyl-1-methylethoxy group.

As the aryl group of the $C_{1-8}$ alkoxy group substuituted with a substituted aryl group for $Q^1$, for example, the same aryl groups as those for X can be exemplified. The substituent of the aryl group is not particularly limited and, for example, the same substituents as those of the aryl group for X can be exemplified in a chemically acceptable range. Specific examples of the $C_{1-8}$ alkoxy group substituted with a substituted aryl group include a 2-methylphenylmethoxy group, a 3-methylphenylmethoxy group, a 4-chlorophenylmethoxy group, a 1-(4-chlorophenyl)ethoxy group, a 3-chlorophenylmethoxy group, a 2-methoxyphenylmethoxy group, a 3-methoxyphenylmethoxy group, a 4-methylsulfonylphenylmethoxy group, and a 3-phenylphenylmethoxy group.

As the heterocyclic group of the $C_{1-8}$ alkoxy group substuituted with an unsubstituted or substituted heterocyclic group for $Q^1$, for example, the same heterocyclic groups as those for R can be exemplified. The substituent of the heterocycle is not particularly limited and, for example, the same substituents as those of the aryl group for X can be exemplified in a chemically acceptable range. Specific examples of the $C_{1-8}$ alkoxy group substituted with an unsubstituted or substituted heterocyclic group include a 2-pyridylmethoxy group, a 6-methylpyridin-2-ylmethoxy group, a 4-pyridylmethoxy group, a 1-(4-pyridyl)-1-methylethoxy group, a 2-oxazolylmethoxy group, and a 2-benzoxazolylmethoxy group.

The substituent of the $C_{1-8}$ alkoxy group substituted with an unsubstituted or substituted $C_{1-8}$ alkoxy group for $Q^1$ is not particularly limited and, for example, the same substituents as those of the aryl group for X can be exemplified in a chemically acceptable range. Specific examples of the $C_{1-8}$ alkoxy group substituted with an unsubstituted or substituted $C_{1-8}$ alkoxy group include a methoxymethoxy group, an ethoxymethoxy group, a 2-isopropoxyethoxy group, a 2-(methoxyethoxy)ethoxy group, a 2-trifluoromethoxyethoxy group, and a 2-pentafluoroethoxyethoxy group.

Specific examples of the aryloxy group of the $C_{1-8}$ alkoxy group substituted with an unsubstituted or substituted aryloxy group for $Q^1$ include a phenoxy group and a 1-naphthoxy group. The substituent of the aryloxy group is not particularly limited and, for example, the same substituents as those of the aryl group for X can be exemplified in a chemically acceptable range. Specific examples of the $C_{1-8}$ alkoxy group substituted with an unsubstituted or substituted aryloxy group include a phenoxymethoxy group, a 2-phenoxyethoxy group, a 2-(4-chlorophenoxy)ethoxy group, and a 2-(4-methoxyphenoxy)ethoxy group.

As the aralkyloxy group of the $C_{1-8}$ alkoxy group substuituted with an unsubstituted or substituted aralkyloxy group for Q', for example, a benzyloxy group and a phenethyloxy group can be exemplified. The substituent thereof is not particularly limited and, for example, the same substituents as those of the aryl group for X can be exemplified in a chemically acceptable range. Specific examples of the $C_{1-8}$ alkoxy group substituted with an unsubstituted or substituted aralkyloxy group include a benzyloxymethoxy group, a 2-benzyloxyethoxy group, a phenethyloxymethoxy group, and a (4-chlorophenylmethoxy)methoxy group.

As the aryl group of the $C_{2-8}$ alkynyloxy group substuituted with an unsubstituted or substituted aryl group for Q', for example, the same aryl groups as those for X can be exemplified. As the $C_{2-8}$ alkynyloxy group, for example, the same alkynyl groups as those for R can be exemplified. The substituent of the aryl group is not particularly limited and, for example, the same substituents as those of the aryl group for X can be exemplified in a chemically acceptable range. Specific examples of the $C_{2-8}$ alkynyloxy group substituted with an unsubstituted or substituted aryl group include a 3-phenyl-2-propynyloxy group, a 1-phenyl-2-propynyloxy group, and a 3-phenyl-1,1-dimethyl-2-propynyloxy group.

Specific examples of the alkylthio group of the $C_{1-8}$ alkoxy group substituted with an unsubstituted or substituted $C_{1-8}$ alkylthio group for $Q^1$ include a methylthio group, an ethylthio group, an n-propylthio group, an isopropylthio group, an n-butylthio group, an isobutylthio group, an s-butylthio group, and a t-butylthio group. The substituent thereof is not particularly limited and, for example, the same substituents as those of the aryl group for X can be exemplified in a chemically acceptable range. Specific examples of the $C_{1-8}$ alkoxy group substituted with an unsubstituted or substituted $C_{1-8}$ alkylthio group include a methylthiomethoxy group, a methylthio-n-butoxy group, and a 1-methylthioethoxy group.

Specific examples of the arylthio group of the $C_{1-8}$ alkoxy group substituted with an unsubstituted or substituted arylthio group for $Q^1$ include a phenylthio group and a naphthylthio group. The substituent thereof is not particularly limited and, for example, the same substituents as those of the aryl group for X can be exemplified in a chemically acceptable range. Specific examples of the $C_{1-8}$ alkoxy group substituted with a substituted or unsubstituted arylthio group include a phenylthiomethoxy group, a 2-phenylthioethoxy group, a naphthylthiomethoxy group, and a 1-phenylthioethoxy group.

Specific examples of the alkylsulfinyl group of the $C_{1-8}$ alkoxy group substituted with an unsubstituted or substituted $C_{1-8}$ alkylsulfinyl group for $Q^1$ include a methylsulfinyl group, an ethylsulfinyl group, and a t-butylsulfinyl group. The substituent thereof is not particularly limited and, for example, the same substituents as those of the aryl group for X can be exemplified in a chemically acceptable range. Specific examples of the $C_{1-8}$ alkoxy group substituted with an unsubstituted or substituted $C_{1-8}$alkylsulfinyl group include a methylsulfinylmethoxy group, a methylsulfinyl-n-butoxy group, and a 1-methylsulfinylethoxy group.

Specific examples of the arylsulfinyl group of the $C_{1-8}$ alkoxy group substuituted with an unsubstituted or substituted arylsulfinyl group for $Q^1$ include a phenylsulfenyl group. The substituent thereof is not particularly limited and, for example, the same substituents as those of the aryl group for X can be exemplified in a chemically acceptable range. Specific examples of the $C_{1-8}$ alkoxy group substituted with an unsubstituted or substituted arylsulfinyl group include a phenylsulfinylmethoxy group, a 2-phenylsulfinylethoxy group, a naphthylsulfinylmethoxy group, and a 1-phenylsulfenylethoxy group.

Specific examples of the alkylsulfonyl group of the $C_{1-8}$ alkoxy group substituted with an unsubstituted or substituted $C_{1-8}$ alkylsulfonyl group for $Q^1$ include a methylsulfonyl group, an ethylsulfonyl group, and a t-butylsulfonyl group. The substituent thereof is not particularly limited and, for example, the same substituents as those of the aryl group for X can be exemplified in a chemically acceptable range. Specific examples of the $C_{1-8}$ alkoxy group substituted with an unsubstituted or substituted $C_{1-8}$ alkylsulfonyl group include a methylsulfonylmethoxy group, a methylsulfonyl-n-butoxy group, and a 1-methylsulfonylethoxy group.

Specific examples of the arylsulfonyl group of the $C_{1-8}$ alkoxy group substituted with an unsubstituted or substituted arylsulfonyl group for $Q^1$ include a phenylsulfonyl group. The substituent thereof is not particularly limited and, for example, the same substituents as those of the aryl group for X can be exemplified in a chemically acceptable range. Specific examples of the $C_{1-8}$ alkoxy group substituted with an unsubstituted or substituted arylsulfonyl group include a phenylsulfonylmethoxy group, a 2-phenylsulfonylethoxy group, a naphthylsulfonylmethoxy group, and a 1-phenylsulfonylethoxy group.

Specific examples of the aralkyl group of the $C_{1-8}$ alkoxy group substituted with an amino group which is unsubstituted or substituted with an (unsubstituted or substituted aralkyl group) for $Q^1$ include a benzyl group, a phenethyl group, and a 1-naphthylmethyl group. The substituent thereof is not particularly limited and, for example, the same substituents as those of the aryl group for X can be exemplified in a chemically acceptable range. Specific examples of the $C_{1-8}$ alkoxy group substituted with an amino group which is unsubstituted or substituted with an (unsubstituted or substituted aralkyl group) include an aminomethoxy group, a 3-aminopropoxy group, a 6-aminohexyloxy group, a 1-aminoethoxy group, benzylaminomethoxy group, an N-benzyl-N-methylaminomethoxy group, and an N-benzyl-N-methoxycarbonylaminomethoxy group.

As the alkyl group of the $C_{1-8}$ alkoxy group which is substituted with an amino group substituted with an (unsubstituted or substituted alkyl group) for Q', for example, the same alkyl groups as those for X can be exemplified. The substituent thereof is not particularly limited and, for example, the same substituents as those of the aryl group for X can be exemplified in a chemically acceptable range. Specific examples of the $C_{1-8}$ alkoxy group which is substituted with an amino group substituted with an (unsubstituted or substituted alkyl group) include a methylaminomethoxy group, a 3-methylaminopropoxy group, a 6-methylaminohexyloxy group, a 1-methylaminoethoxy group, a dimethylaminomethoxy group, a 2-ethylaminoethoxy group, and an N-methyl-N-methoxycarbonylaminomethoxy group.

The substituent of the unsubstituted or substituted aryloxy group for $Q^1$ is not particularly limited, and the same substituents as those of the aryl group for X can be exemplified in a chemically acceptable range. Specific examples of the unsubstituted or substituted aryloxy group include a phenoxy group, a naphthyloxy group, a 4-chlorophenoxy group, a 4-methoxyphenoxy group, a 2,4-dichlorophenoxy group, and a 2-trifluoromethylphenoxy group.

As the $C_{1-8}$ alkyl group of the $C_{1-8}$ alkyl group substituted with a carboxyl group for $Q^1$, for example, the same substituents as those of the alkyl group for X can be exemplified. Hereinafter, specific examples of the $C_{1-8}$ alkoxy group are the same specific examples. Specific examples of the $C_{1-8}$ alkyl group substituted with a carboxyl group include a 2-carboxyethyl group and a 6-carboxyhexyl group.

Specific examples of the aralkyl group of the $C_{1-8}$ alkyl group substituted with an amino group which is unsubstituted or substituted with an (unsubstituted or substituted aralkyl group) for $Q^1$ include a benzyl group, a phenethyl group, and a 1-naphthylmethyl group. The substituent thereof is not particularly limited and, for example, the same substituents as those of the aryl group for X can be exemplified in a chemically acceptable range. Specific examples of the $C_{1-8}$ alkyl group substituted with an amino group which is unsubstituted or substituted with an (unsubstituted or substituted aralkyl group) include an aminomethyl group, a 3-aminopropyl group, a 6-aminohexyl group, a 1-aminoethyl group, a benzylaminomethyl group, an N-benzyl-N-methylaminomethyl group, and an N-benzyl-N-methoxycarbonylaminomethyl group.

As the alkyl group of the $C_{1-8}$ alkyl group which is substituted with an amino group substituted with an (unsubstituted or substituted alkyl group) for $Q^1$, for example, the same alkyl groups as those for X can be exemplified. The substituent thereof is not particularly limited and, for example, the same substituents as those of the aryl group for X can be exemplified in a chemically acceptable range. Specific examples of the $C_{1-8}$ alkyl group which is substituted with an amino group substituted with an (unsubstituted or substituted alkyl group) include a methylaminomethyl group, a 3-methylaminopropyl group, a 6-methylaminohexyl group, a 1-methylaminoethyl group, a dimethylaminomethyl group, a 2-ethylaminoethyl group, and an N-methyl-N-methoxycarbonylaminomethyl group.

Specific examples of the aryloxy group of the $C_{1-8}$ alkyl group substituted with an unsubstituted or substituted aryloxy group for $Q^1$ include a phenoxy group and a naphthyloxy group. The substituent thereof is not particularly limited and, for example, the same substituents as those of the aryl group for X can be exemplified in a chemically acceptable range. Specific examples of the $C_{1-8}$ alkyl group substituted with an unsubstituted or substituted aryloxy group include a phenoxymethyl group, a naphthyloxymethyl group, a 2-phenoxyethyl group, and a 1-phenoxyethyl group.

Specific examples of the acyl group of the $C_{1-8}$ alkyl group substituted with an acyl group for $Q^1$ include a formyl group, an acetyl group, a propionyl group, a benzoyl group, a cyclohexylcarbonyl group, and a phthaloyl group. Specific examples of the acyl group of the $C_{1-8}$ alkyl group substituted with an acyl group include a 4-acetyl-n-butyl group, an acetylmethyl group, a 1-acetylethyl group, and a 3-benzoyl-n-propyl group.

As the heterocyclicoxy group of the $C_{1-8}$ alkyl group substituted with an unsubstituted or substituted heterocyclicoxy group for $Q^1$, for example, those in which an oxygen atom is bonded to the bonding position of those of the heterocyclic group for R can be exemplified. The substituent of the heterocycle is not particularly limited and, for example, the same substituents as those of the aryl group for X can be exemplified in a chemically acceptable range. Specific examples of the $C_{1-8}$ alkyl group substituted with an unsubstituted or substituted heterocyclicoxy group include a 2-pyridyloxymethyl group, a 2-(2-pyridyloxy)ethyl group, a 1-(2-pyridyloxy) ethyl group, a (1-(2-pyridyloxy)-1-methyl)ethyl group, a 3-pyridyloxymethyl group, a 2-oxazolyloxymethyl group, and a 4-piperazyloxymethyl group.

Among these, $Q^1$ is preferably an alkenyloxy group in which carbon attached to the oxygen atom is tertiary carbon, such as a 1,1-dimethyl-2-propenyloxy group, an alkynyloxy group in which carbon attached to the oxygen atom is tertiary carbon, such as a 1,1-dimethyl-2-butynyloxy group, a $C_{1-8}$ alkoxy group substituted with an alkoxycarbonylamino group, a $C_{1-8}$ alkoxy group substituted with a $C_{3-8}$ cycloalkyl group, a $C_{1-8}$ branched alkoxy group substituted with an unsubstituted aryl group, a $C_{1-8}$ alkoxy group substituted with a substituted aryl group, a $C_{1-8}$ alkoxy group substituted with a substituted or unsubstituted heterocyclic group, a $C_{1-8}$ alkoxy group substituted with an unsubstituted or substituted $C_{1-8}$ alkoxy group, a $C_{1-8}$ alkoxy group substituted with an unsubstituted or substituted aryloxy group, a $C_{1-8}$ alkoxy group substituted with an unsubstituted or substituted aralkyloxy group, a $C_{2-8}$ alkynyloxy group substituted with an unsubstituted or substituted aryl group, a $C_{1-8}$ alkoxy group substituted with an unsubstituted or substituted $C_{1-8}$ alkylthio group, a $C_{1-8}$ alkoxy group substituted with a substituted or unsubstituted arylthio group, a $C_{1-8}$ alkoxy group substituted with an unsubstituted or substituted $C_{1-8}$ alkylsulfinyl group, a $C_{1-8}$ alkoxy group substituted with an unsubstituted or substituted arylsulfinyl group, a $C_{1-8}$ alkoxy group substituted with an unsubstituted or substituted $C_{1-8}$ alkylsulfonyl group, a $C_{1-8}$ alkoxy group substituted with an unsubstituted or substituted arylsulfonyl group, a $C_{1-8}$ alkoxy group substituted with an amino group which is unsubstituted or substituted with an (unsubstituted or substituted alkyl group), a $C_{1-8}$ alkoxy group which is substituted with an amino group substituted with an (unsubstituted or substituted aralkyl group), an unsubstituted or substituted aryloxy group, a $C_{1-8}$ alkyl group substituted with a carboxyl group, a $C_{1-8}$ alkyl group substituted with an amino group which is unsubstituted or substituted with an (unsubstituted or substituted aralkyl group), a $C_{1-8}$ alkyl group which is substituted with an amino group substituted with an (unsubstituted or substituted alkyl group), a $C_{1-8}$ alkyl group substituted with an unsubstituted or substituted aryloxy group, an alkyl group substituted with an acyl group, or an alkyl group substituted with an unsubstituted or substituted heterocyclicoxy group, and more preferably an alkenyloxy group in which carbon attached to the oxygen atom is tertiary carbon, such as a 1,1-dimethyl-2-propenyloxy group, an alkynyloxy group in which carbon attached to the oxygen atom is tertiary carbon, such as a 1,1-dimethyl-2-butynyloxy group, a $C_{1-8}$ alkoxy group substituted with a $C_{3-8}$ cycloalkyl group, a $C_{1-8}$ branched alkoxy group substituted with an unsubstituted aryl group, a $C_{1-8}$ alkoxy group substituted with a substituted aryl group, a $C_{1-8}$ alkoxy group substituted with an unsubstituted or substituted heterocyclic group, a $C_{1-8}$ alkoxy group substituted with an unsubstituted or substituted $C_{1-8}$ alkoxy group, a $C_{1-8}$ alkoxy group substituted with an unsubstituted or substituted aryloxy group, a $C_{1-8}$ alkoxy group substituted with an unsubstituted or substituted aralkyloxy group, a $C_{2-8}$ alkynyloxy group substituted with an unsubstituted or substituted aryl group, a $C_{1-8}$ alkoxy group substituted with an unsubstituted or substituted $C_{1-8}$ alkylthio group, a $C_{1-8}$ alkoxy group substituted with an amino group which is unsubstituted or substituted with an (unsubstituted or substituted alkyl group), a $C_{1-8}$ alkoxy group which is substituted with an amino group substituted with an (unsubstituted or substituted aralkyl group), a $C_{1-8}$ alkyl group substituted with an amino group which is unsubstituted or substituted with an (unsubstituted or substituted aralkyl group), a $C_{1-8}$ alkyl group which is substituted with an amino group substituted with an (unsubstituted or substituted alkyl group), a $C_{1-8}$ alkyl group substituted with an unsubstituted or substituted aryloxy group, a $C_{1-8}$ alkyl group substituted with an acyl group, or a $C_{1-8}$ alkyl group substituted with an unsubstituted or substituted heterocyclicoxy group.

Furthermore, the alkenyloxy group in which carbon attached to the oxygen atom is tertiary carbon, such as a 1,1-dimethyl-2-propenyloxy group is preferably a 1,1-dialkyl-substituted alkenyl group, the alkynyloxy group in which carbon attached to the oxygen atom is tertiary carbon, such as a 1,1-dimethyl-2-butynyloxy group is preferably a 1,1-dialkyl-substituted alkynyloxy group, the $C_{1-8}$ alkoxy group substituted with a $C_{3-8}$ cycloalkyl is preferably a $C_{3-6}$ cycloalkyl $C_{1-2}$ alkyl group, the $C_{1-8}$ branched alkoxy group substituted with an unsubstituted aryl group is preferably a $C_{1-4}$ branched alkoxy group substituted with an unsubstituted aryl group at the 1- or 2-position, the $C_{1-8}$ alkoxy group substituted with a substituted aryl group is preferably a $C_{1-4}$ alkoxy group which is substituted with an aryl group substituted with a cyano group, a halogen atom, an alkoxy group, an alkyl group, an aryl group, or an alkylsulfonyl group, more preferably a $C_{1-4}$ alkoxy group which is substituted with a substituted aryl group substituted at the 2- or 3-position of the aryl group, and still more preferably a $C_{1-4}$ alkyl group which is substituted with an aryl group substituted with a cyano group, a halogen atom, an alkoxy group, an alkyl group, an aryl group, or an alkylsulfonyl group at the 2- or 3-position, the $C_{1-8}$ alkoxy group substituted with an unsubstituted or substituted heterocyclic group is preferably a $C_{1-4}$ alkoxy group substituted with an unsubstituted or substituted aromatic heterocyclic group, a $C_{1-8}$ alkoxy group substituted with an unsubstituted or substituted $C_{1-8}$ alkoxy group is preferably a $C_{1-4}$ alkoxy group substituted with an unsubstituted or substituted $C_{1-4}$ alkoxy group, the $C_{1-8}$ alkoxy group substituted with an unsubstituted or substituted aryloxy group is preferably a $C_{1-4}$ alkoxy group substituted with an unsubstituted or substituted phenoxy group, the $C_{1-8}$ alkoxy group substituted with an unsubstituted or substituted aralkyloxy group is preferably a $C_{1-4}$ alkoxy group substituted with an unsubstituted or substituted benzyloxy group, the $C_{2-8}$ alkynyloxy group substituted with an unsubstituted or substituted aryl group is preferably a 1,1-dialkyl-substituted $C_{2-8}$ alkynyloxy group substituted with an unsubstituted or substituted phenyl group, the $C_{1-8}$ alkoxy group substituted with an unsubstituted or substituted $C_{1-8}$ alkylthio group is preferably a $C_{1-4}$ alkoxy group substituted with an unsubstituted or substituted $C_{1-4}$ alkylthio group, the $C_{1-8}$ alkoxy group substituted with an amino group which is unsubstituted or substituted with an (unsubstituted or substituted alkyl group) is preferably a $C_{1-4}$ alkoxy group substituted with an amino group which is unsubstituted or substituted with an (unsubstituted or substituted alkyl group), the $C_{1-8}$ alkoxy group which is substituted with an amino group substituted with an (unsubstituted or substituted aralkyl group) is preferably $C_{1-4}$ alkoxy group which is substituted with an amino group substituted with an (unsubstituted or substituted (benzyl group or phenethyl group)), the $C_{1-8}$ alkyl group substituted with an amino group which is unsubstituted or substituted with an (unsubstituted or substituted aralkyl group) is preferably a $C_{1-4}$ alkyl group substituted with an amino group which is unsubstituted or substituted with an (unsubstituted or substituted (benzyl group or phenethyl group)), the $C_{1-8}$ alkyl group which is substituted with an amino group substituted with an (unsubstituted or substituted alkyl group) is preferably a $C_{1-4}$ alkyl group which is substituted with an amino group substituted with an (unsubstituted or substituted alkyl group), the $C_{1-8}$ alkyl group substituted with an unsubstituted or substituted aryloxy group is preferably a $C_{1-4}$ alkyl group substituted with an unsubstituted or substituted phenoxy group, the $C_{1-8}$ alkyl group substituted with an acyl group is preferably a $C_{1-4}$ alkyl group substituted with a formyl group or an alkylcarbonyl group, or the $C_{1-8}$ alkyl group substituted with an unsubstituted or substituted heterocyclicoxy group is preferably a $C_{1-4}$ alkyl group substituted with an unsubstituted or substituted aromatic heterocyclicoxy group.

When n2 is 1 and R is a halogen atom, Z represents a hydrogen atom, an amino group, or a group represented by formula: $Q^2C(=O)NH-$ (in which $Q^2$ represents a hydrogen atom, a $C_{1-8}$ haloalkyl group, a $C_{2-8}$ alkenyl group, a $C_{2-8}$ haloalkenyl group, a $C_{2-8}$ alkynyl group, a $C_{2-8}$ haloalkynyl group, a $C_{1-8}$ alkoxy group, a $C_{1-8}$ haloalkoxy group, a $C_{2-8}$ alkenyloxy group, a $C_{2-8}$ haloalkenyloxy group, a $C_{2-8}$ alkynyloxy group, a $C_{2-8}$ haloalkynyloxy group, a $C_{3-8}$ cycloalkyl group, a $C_{3-8}$ cycloalkyloxy group, a $C_{1-8}$ alkylamino group, a $C_{1-8}$ alkoxy group substituted with an unsubstituted or substituted amino group, a $C_{1-8}$ alkoxy group substituted with a $C_{3-8}$ cycloalkyl group, an unsubstituted or substituted aralkyloxy group, a $C_{1-8}$ alkoxy group substituted with a substituted or unsubstituted heterocyclic group, a $C_{1-8}$ alkoxy group substituted with an unsubstituted or substituted $C_{1-8}$ alkoxy group, a $C_{1-8}$ alkoxy group substituted with an unsubstituted or substituted aryloxy group, a $C_{1-8}$ alkoxy group substituted with an unsubstituted or substituted aralkyloxy group, a $C_{2-8}$ alkynyloxy group substituted with an unsubstituted or substituted aryl group, a $C_{1-8}$ alkoxy group substituted with an unsubstituted or substituted $C_{1-8}$ alkylthio group, a $C_{1-8}$ alkoxy group substituted with a substituted or unsubstituted arylthio group, a $C_{1-8}$ alkoxy group substituted with an unsubstituted or substituted $C_{1-8}$ alkylsulfinyl group, a $C_{1-8}$ alkoxy group substituted with an unsubstituted or substituted arylsulfinyl group, a $C_{1-8}$ alkoxy group substituted with an unsubstituted or substituted $C_{1-8}$ alkylsulfonyl group, a $C_{1-8}$ alkoxy group substituted with an unsubstituted or substituted arylsulfonyl group, an unsubstituted or substituted aryloxy group, a $C_{1-8}$ alkyl group substituted with a carboxyl group, a $C_{1-8}$ alkyl group substituted with an unsubstituted or substituted amino group, a $C_{1-8}$ alkyl group substituted with an unsubstituted or substituted aryloxy group, a $C_{1-8}$ alkyl group substituted with an unsubstituted or substituted $C_{1-8}$ alkylthio group, a $C_{1-8}$ alkyl group substituted with an unsubstituted or substituted alkoxy group, a $C_{1-8}$ alkyl group substituted with an acyl group, or a $C_{1-8}$ alkyl group substituted with an unsubstituted or substituted heterocyclicoxy group).

Specific examples of the $C_{1-8}$ haloalkyl group, the $C_{2-8}$ haloalkenyl group, the $C_{2-8}$ alkynyl group, the $C_{2-8}$ haloalkynyl group, the $C_{1-8}$ haloalkoxy group, the $C_{2-8}$ alkenyloxy group, the $C_{2-8}$ haloalkenyloxy group, the $C_{2-8}$ alkynyloxy group, the $C_{2-8}$ haloalkynyloxy group, the $C_{1-8}$ alkoxy group substituted with an $C_{3-8}$ cycloalkyl group, the $C_{1-8}$ alkoxy group substituted with a substituted or unsubstituted heterocyclic group, the $C_{1-8}$ alkoxy group substituted with an unsubstituted or substituted $C_{1-8}$ alkoxy group, the $C_{1-8}$ alkoxy group substituted with an unsubstituted or substituted aryloxy group, the $C_{1-8}$ alkoxy group substituted with an unsubstituted or substituted aralkyloxy group, the $C_{2-8}$ alkynyloxy group substituted with an unsubstituted or substituted aryl group, the $C_{1-8}$ alkoxy group substituted with an unsubstituted or substituted $C_{1-8}$ alkylthio group, the $C_{1-8}$ alkoxy group substituted with an unsubstituted or substituted arylthio group, the $C_{1-8}$ alkoxy group substituted with an unsubstituted or substituted $C_{1-8}$ alkylsulfinyl group, the $C_{1-8}$ alkoxy group substituted with an unsubstituted or substituted arylsulfinyl group, the $C_{1-8}$ alkoxy group substituted with an unsubstituted or substituted $C_{1-8}$ alkylsulfonyl group, the $C_{1-8}$ alkoxy group substituted with an unsubstituted or substituted arylsulfonyl group, the unsubstituted or substituted aryloxy group, the $C_{1-8}$ alkyl group substituted with a carboxyl group, the $C_{1-8}$ alkyl group substituted with an unsubstituted or substituted aryloxy group, the $C_{1-8}$ alkyl group substituted with an acyl group, the or $C_{1-8}$ alkyl group substituted with an unsubstituted or substituted heterocyclicoxy group for $Q^2$ include the same specific examples as those of $Q^1$.

Specific examples of the $C_{3-8}$ cycloalkyl group for $Q^2$ include a cyclopropyl group, a cyclohexyl group, a cyclobutyl group, a cyclopentyl group, a cyclohexyl group, a cycloheptyl group, and a cyclooctyl group.

Specific examples of the $C_{3-8}$ cycloalkyloxy group for $Q^2$ include a cyclopropyloxy group, a cyclohexyloxy group, a cyclobutyloxy group, a cyclopentyloxy group, a cyclohexyloxy group, a cycloheptyloxy group, and a cyclooctyloxy group.

Specific examples of the $C_{1-8}$ alkylamino group for $Q^2$ include a methylamino group, a diethylamino group, an ethylmethylamino group, a di n-heptylamino group, and a t-butylamino group.

The substituent of the amino group of the $C_{1-8}$ alkoxy group substituted with an unsubstituted or substituted amino group for $Q^2$ is not particularly limited and, for example, the same substituents as those of the aryl group for X can be exemplified in a chemically acceptable range. Specific examples of the $C_{1-8}$ alkoxy group substituted with an unsubstituted or substituted amino group include a 2-aminoethoxy group, a 6-aminohexyloxy group, an N-acetylaminoethoxy group, a 2-(N-acetylamino)ethoxy group, a 1-(N-acetylamino)ethoxy group, a 2-(N-acetyl-N-methylamino)ethoxy group, a 2-(N-benzoyl)aminoethoxy group, an N-methoxycarbonylaminomethoxy group, an N-t-butoxycarbonylaminomethoxy group, a 2-(N-ethoxycarbonylamino)ethoxy group, and a 2-(N-t-butoxycarbonyl-N-benzylamino) ethoxy group.

Specific examples of the aralkyloxy group of the unsubstituted or substituted aralkyloxy group for $Q^2$ include a benzyloxy group, a phenethyloxy group, and a 1-naphthylmethoxy group. The substituent thereof is not particularly limited and, for example, the same substituents as those of the aryl group for X can be exemplified in a chemically acceptable range. Specific examples of the unsubstituted or substituted aralkyloxy group include a benzyloxy group, a phenethyloxy group, a 1-phenylethoxy group, a 1-phenyl-1-methylethoxy group, a 2-phenyl-1-methylethoxy group, a 2-methylphenylmethoxy group, a 3-methylphenylmethoxy group, a 4-chlorophenylmethoxy group, a 1-(4-chlorophenyl)ethoxy group, a 3-chlorophenylmethoxy group, a 2-methoxyphenylmethoxy group, a 3-methoxyphenylmethoxy group, a 4-methylsulfonylphenylmethoxy group, and a 3-phenylphenylmethoxy group.

Specific examples of the alkylthio group of the $C_{1-8}$ alkyl group substituted with an unsubstituted or substituted $C_{1-8}$ alkylthio group for $Q^2$ include a methylthio group, an ethylthio group, an n-propylthio group, an isopropylthio group, an n-butylthio group, an isobutylthio group, an s-butylthio group, and a t-butylthio group. The substituent is not particularly limited and, for example, the same substituents as those of the aryl group for X can be exemplified in a chemically acceptable range. Specific examples of the $C_{1-8}$ alkyl group substituted with an unsubstituted or substituted $C_{1-8}$ alkylthio group include a methylthiomethyl group, a methylthio-n-butyl group, and a 1-methylthioethyl group.

As the alkoxy group of the $C_{1-8}$ alkyl group substituted with an unsubstituted or substituted alkoxy group for $Q^2$, for example, the same alkoxy groups as those for X can be exemplified. The substituent thereof is not particularly limited and, for example, the same substituents as those of the aryl group for X can be exemplified in a chemically acceptable range. Specific examples of the $C_{1-8}$ alkyl group substituted with an unsubstituted or substituted alkoxy group include a methoxymethyl group, an ethoxymethyl group, a 2-isopropoxyethyl group, an n-propoxyethyl group, a t-butoxy-1-butyl group, a 2-(2-methoxyethoxy)ethyl group, a 2-trifluoromethoxyethyl group, and a 2-pentafluoroethoxyethyl group.

Among these, Z is preferably a group represented by formula: $Q^2C(\!=\!O)NH\!-\!$, and $Q^2$ is preferably a $C_{2-8}$ haloalkenyl group, a $C_{2-8}$ alkynyl group, a $C_{2-8}$ haloalkynyl group, a $C_{1-8}$ haloalkoxy group, a $C_{2-8}$ alkenyloxy group, a $C_{2-8}$ haloalkenyloxy group, a $C_{2-8}$ alkynyloxy group, a $C_{2-8}$ haloalkynyloxy group, a $C_{1-8}$ alkoxy group substituted with an amino group which is unsubstituted or substituted with an (unsubstituted or substituted alkyl group), a $C_{1-8}$ alkoxy group which is substituted with an amino group substituted with an (unsubstituted or substituted aralkyl group), a $C_{1-8}$ alkoxy group substituted with an alkoxycarbonylamino group, a $C_{1-8}$ alkoxy group substituted with a $C_{3-8}$ cycloalkyl group, a $C_{1-8}$ branched alkoxy group substituted with an unsubstituted aryl group, a $C_{1-8}$ alkoxy group substituted with a substituted aryl group, a $C_{1-8}$ alkoxy group substituted with a substituted or unsubstituted heterocyclic group, a $C_{1-8}$ alkoxy group substituted with an unsubstituted or substituted $C_{1-8}$ alkoxy group, a $C_{1-8}$ alkoxy group substituted with an unsubstituted or substituted aryloxy group, a $C_{1-8}$ alkoxy group substituted with an unsubstituted or substituted aralkyloxy group, a $C_{2-8}$ alkynyloxy group substituted with an unsubstituted or substituted aryl group, a $C_{1-8}$ alkoxy group substituted with an unsubstituted or substituted $C_{1-8}$ alkylthio group, a $C_{1-8}$ alkoxy group substituted with an unsubstituted or substituted arylthio group, a $C_{1-8}$ alkoxy group substituted with an unsubstituted or substituted $C_{1-8}$ alkylsulfinyl group, a $C_{1-8}$ alkoxy group substituted with an unsubstituted or substituted arylsulfinyl group, a $C_{1-8}$ alkoxy group substituted with an unsubstituted or substituted $C_{1-8}$ alkylsulfonyl group, a $C_{1-8}$ alkoxy group substituted with an unsubstituted or substituted arylsulfonyl group, an unsubstituted or substituted aryloxy group, a $C_{1-8}$ alkyl group substituted with a carboxyl group, a $C_{1-8}$ alkyl group which is substituted with an amino group substituted with an (unsubstituted or substituted alkyl group), a $C_{1-8}$ alkyl group substituted with an amino group which is unsubstituted or substituted with an (unsubstituted or substituted aralkyl group), a $C_{1-8}$ alkyl group substituted with an unsubstituted or substituted aryloxy group, a $C_{1-8}$ alkyl group substituted with an amino group, or a $C_{1-8}$ alkyl group substituted with an unsubstituted or substituted heterocyclicoxy group, and more preferably an alkenyloxy group, in which carbon attached to the oxygen atom is tertiary carbon, such as a 1,1-dimethyl-2-propenyloxy group, an alkynyloxy group in which carbon attached to the oxygen atom is tertiary carbon, such as a 1,1-dimethyl-2-butynyloxy group, a $C_{1-8}$ alkoxy group substituted with a $C_{3-8}$ cycloalkyl group, a $C_{1-8}$ branched alkoxy group substituted with an unsubstituted aryl group, a $C_{1-8}$ alkoxy group substituted with a substituted aryl group, a $C_{1-8}$ alkoxy group substituted with an unsubstituted or substituted heterocyclic group, a $C_{1-8}$ alkoxy group substituted with an unsubstituted or substituted $C_{1-8}$ alkoxy group, a $C_{1-8}$ alkoxy group substituted with an unsubstituted or substituted aryloxy group, a $C_{1-8}$ alkoxy group substituted with an unsubstituted or substituted aralkyloxy group, a $C_{2-8}$ alkynyloxy group substituted with an unsubstituted or substituted aryl group, a $C_{1-8}$ alkoxy group substituted with an unsubstituted or substituted $C_{1-8}$ alkylthio group, a $C_{1-8}$ alkoxy group substituted with an amino group which is unsubstituted or substituted with an (unsubstituted or substituted alkyl group), a $C_{1-8}$ alkoxy group which is substituted with an amino group substituted with an (unsubstituted or substituted aralkyl group), a $C_{1-8}$ alkyl group substituted with an amino group which is unsubstituted or substituted with an (unsubstituted or substituted aralkyl group), a $C_{1-8}$ alkyl group which is substituted with an amino group substituted with an (unsubstituted or substituted alkyl group), a $C_{1-8}$ alkyl group substituted with an unsubstituted or substituted aryloxy group, a $C_{1-8}$ alkyl group substituted with an acyl group, or a $C_{1-8}$ alkyl group substituted with an unsubstituted or substituted heterocyclicoxy group.

As more preferred above functional groups, the same as those for $Q^1$ can be exemplified.

When n2 is 1 or more and at least one R is a cyano group, a nitro group, a hydroxyl group, a thiol group, a formyl group, a carboxyl group, an unsubstituted or substituted amino group, an unsubstituted or substituted $C_{1-8}$ alkyl group, an unsubstituted or substituted $C_{2-8}$ alkenyl group, an unsubstituted or substituted $C_{2-8}$ alkynyl group, an unsubstituted or substituted aryl group, an unsubstituted or substituted heterocyclic group, $OR^1$, $S(O)_m R^1$, $COR^1$, or $CO_2 R^1$, or n2 is 2 or more and at least two R(s) are halogen atoms, Z represents a hydrogen atom, an amino group, or a group represented by formula: $Q^3 C(=O)NH-$ (in which $Q^3$ represents a hydrogen atom, a $C_{1-8}$ alkyl group, a $C_{1-8}$ haloalkyl group, a $C_{2-8}$ alkenyl group, a $C_{2-8}$ haloalkenyl group, a $C_{2-8}$ alkynyl group, a $C_{2-8}$ haloalkynyl group, a $C_{1-8}$ alkoxy group, a $C_{1-8}$ haloalkoxy group, a $C_{2-8}$ alkenyloxy group, a $C_{2-8}$ haloalkenyloxy group, a $C_{2-8}$ alkynyloxy group, a $C_{2-8}$ haloalkynyloxy group, a $C_{3-8}$ cycloalkyl group, a $C_{3-8}$ cycloalkyloxy group, a $C_{1-8}$ alkylamino group, a $C_{1-8}$ alkoxy group substituted with an unsubstituted or substituted amino group, a $C_{1-8}$ alkoxy group substituted with a $C_{3-8}$ cycloalkyl group, an unsubstituted or substituted aralkyloxy group, a $C_{1-8}$ alkoxy group substituted with an unsubstituted or substituted heterocyclic group, a $C_{1-8}$ alkoxy group substituted with an unsubstituted or substituted $C_{1-8}$ alkoxy group, a $C_{1-8}$ alkoxy group substituted with an unsubstituted or substituted aryloxy group, a $C_{1-8}$ alkoxy group substituted with an unsubstituted or substituted aralkyloxy group, a $C_{2-8}$ alkynyloxy group substituted with an unsubstituted or substituted aryl group, a $C_{1-8}$ alkoxy group substituted with an unsubstituted or substituted $C_{1-8}$ alkylthio group, a $C_{1-8}$ alkoxy group substituted with a substituted or unsubstituted arylthio group, a $C_{1-8}$ alkoxy group substituted with an unsubstituted or substituted $C_{1-8}$ alkylsulfinyl group, a $C_{1-8}$ alkoxy group substituted with an unsubstituted or substituted arylsulfinyl group, $C_{1-8}$ alkoxy group substituted with an unsubstituted or substituted $C_{1-8}$ alkylsulfonyl group, a $C_{1-8}$ alkoxy group substituted with an unsubstituted or substituted arylsulfonyl group, an unsubstituted or substituted aryloxy group, a $C_{1-8}$ alkyl group substituted with a carboxyl group, a $C_{1-8}$ alkyl group substituted with an unsubstituted or substituted amino group, a $C_{1-8}$ alkyl group substituted with an unsubstituted or substituted aryloxy group, a $C_{1-8}$ alkyl group substituted with an unsubstituted or substituted $C_{1-8}$ alkylthio group, a $C_{1-8}$ alkyl group substituted with an unsubstituted or substituted alkoxy group, a $C_{1-8}$ alkyl group substituted with an acyl group, or a $C_{1-8}$ alkyl group substituted with an unsubstituted or substituted heterocyclicoxy group).

As the $C_{1-8}$ alkyl group for $Q^3$, for example, the same as those of $C_{1-8}$ alkyl group for X can be exemplified.

As specific examples of other functional group contained in $Q^3$, the same as those for $Q^2$ can be exemplified.

Among these, formula: $Q^3 C(=O)NH-$ is preferable. Among these, $Q^3$ is preferably a $C_{1-8}$ alkyl group, a $C_{1-8}$ haloalkyl group, a $C_{2-8}$ alkenyl group, a $C_{1-8}$ alkoxy group, a $C_{2-8}$ alkenyloxy group, a $C_{2-8}$ alkynyloxy group, a $C_{3-8}$ cycloalkyl group, a $C_{3-8}$ cycloalkyloxy group, a $C_{1-8}$ alkylamino group, a $C_{1-8}$ alkoxy group substituted with an unsubstituted or substituted amino group, a $C_{1-8}$ alkoxy group substituted with a $C_{3-8}$ cycloalkyl group, an unsubstituted or substituted aralkyloxy group, a $C_{1-8}$ alkoxy group substituted with an unsubstituted or substituted heterocyclic group, a $C_{1-8}$ alkoxy group substituted with an unsubstituted or substituted $C_{1-8}$ alkoxy group, a $C_{1-8}$ alkoxy group substituted with an unsubstituted or substituted aryloxy group, a $C_{1-8}$ alkoxy group substituted with an unsubstituted or substituted aralkyloxy group, a $C_{2-8}$ alkynyloxy group substituted with an unsubstituted or substituted aryl group, a $C_{1-8}$ alkoxy group substituted with an unsubstituted or substituted $C_{1-8}$ alkylthio group, a $C_{1-8}$ alkoxy group substituted with an unsubstituted or substituted arylthio group, a $C_{1-8}$ alkoxy group substituted with an unsubstituted or substituted $C_{1-8}$ alkylsulfinyl group, $C_{1-8}$ alkoxy group substituted with an unsubstituted or substituted arylsulfinyl group, a $C_{1-8}$ alkoxy group substituted with an unsubstituted or substituted $C_{1-8}$ alkylsulfonyl group, a $C_{1-8}$ alkoxy group substituted with an unsubstituted or substituted arylsulfonyl group, an unsubstituted or substituted aryloxy group, a $C_{1-8}$ alkyl group substituted with a carboxyl group, a $C_{1-8}$ alkyl group substituted with an unsubstituted or substituted amino group, a $C_{1-8}$ alkyl group substituted with an unsubstituted or substituted aryloxy group, a $C_{1-8}$ alkyl group substituted with an unsubstituted or substituted $C_{1-8}$ alkylthio group, a $C_{1-8}$ alkyl group substituted with an unsubstituted or substituted alkoxy group, a $C_{1-8}$ alkyl group substituted with an acyl group, or a $C_{1-8}$ alkyl group substituted with an unsubstituted or substituted heterocyclicoxy group, and still more prefereably the same as those for $Q^1$.

In formula (5), $R^{11}$ represents a hydrogen atom, a halogen atom, a cyano group, a nitro group, a hydroxyl group, a thiol group, an unsubstituted or substituted amino group, an unsubstituted or substituted $C_{1-8}$ alkyl group, an unsubstituted or substituted $C_{2-8}$ alkenyl group, an unsubstituted or substituted $C_{2-8}$ alkynyl group, an unsubstituted or substituted aryl group, an unsubstituted or substituted heterocyclic group, $OR^1$, $S(O)_m R^1$, $COR^1$, or $CO_2 R^1$.

$R^1$ is the same as defined above.

When $R^{11}$ is a hydrogen atom, $Z^{11}$ represents a group represented by formula: $Q^1 C(=O)NH-$ (in which $Q^1$ is the same as defined above).

When $R^{11}$ is a halogen atom, $Z^{11}$ represents a hydrogen atom, an amino group, or a group represented by formula: $Q^2 C(=O)NH-$ (in which $Q^2$ is the same as defined above).

When $R^{11}$ is a cyano group, a nitro group, a hydroxyl group, a thiol group, an unsubstituted or substituted amino group, an unsubstituted or substituted $C_{1-8}$ alkyl group, an unsubstituted or substituted $C_{2-8}$ alkenyl group, an unsubstituted or substituted $C_{2-8}$ alkynyl group, an unsubstituted or substituted aryl group, an unsubstituted or substituted heterocyclic group, $OR^1$, $S(O)_m R^1$, $COR^1$, or $CO_2 R^1$, $Z^{11}$ represents a hydrogen atom, an amino group, or a group represented by formula: $Q^3 C(=O)NH-$ (in which $Q^3$ is the same as defined above).

As the specific examples of $R^{11}$, the same specific examples as those for R in formula (4) can be exemplified. As the specific examples of $Z^{11}$, the same specific examples as those for Z in formula (4) can be exemplified.

As preferred $Z^{11}$, the same as those for Z can be exemplified.

Stereoisomers of (E) and (Z) isomers, based on the double bond of carbon-nitrogen in the oxime moiety, exist in the tetrazoyloxime derivative represented by formula (1). These two stereoisomers and a mixture thereof are included in the present invention. The synthesized product is usually obtained in the form of the (Z) isomer only, or a mixture of (E) and (Z) isomers. Each of (E) and (Z) isomers can be isolated by separation and purification, known methods such as silica gel chromatography. Both (Z) and (E) isomers have activity and (Z) isomer is particularly preferable.

Salts of the compound represented by formula (1) are not particularly limited as long as they are agriculturally or horiculturally acceptable salts. Examples of the salts include salts of inorganic acids, such as hydrochloride, nitrate, sulfate, and phosphate; and salts of organic acids, such as acetate, lactate, propionate, and benzoate.

(Preparation Method)

The tetrazoyloxime derivative represented by formula (1) can be prepared, for example, by the method described in pamphlet of WO 03/016303.

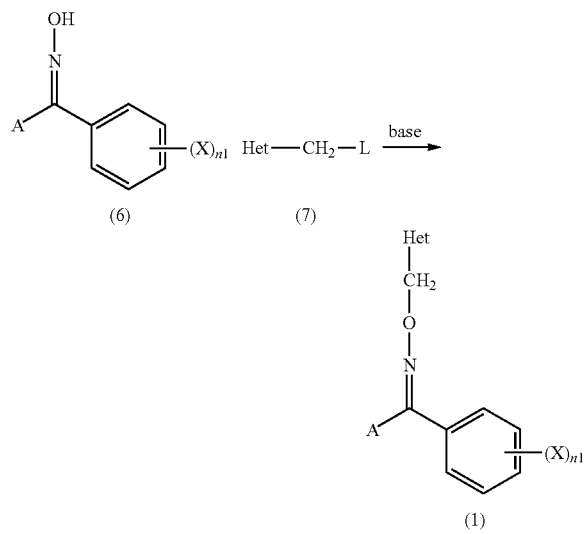

(In the above formulas, A, X, Het and n1 is the same as defined above, and L represents a leaving group such as halogen atom.)

That is to say, the compound represented by formula (1) of the present invention can be obtained by reacting an oxime compound represented by formula (6) with a compound represented by formula (7) in the presence of a base.

As the base used for the reaction, inorganic bases such as sodium hydroxide, potassium hydroxide, sodium hydride, sodium carbonate, and potassium carbonate; and organic bases such as triethylamine, 4-(dimethylamino)pyridine, and pyridine can be used. These bases can be used alone, or two or more kinds of them can be used in combination.

The used amount of the base is usually from 0.01 to 100 mol, and preferably from 0.1 to 5 mol, per mol of the compopund represented by formula (6).

This reaction can be performed in the presence or absence of a solvent.

The solvent to be used is not particularly limited as long as it is a solvent which is inert to the present reaction. Examples of the solvent include hydrocarbon-based solvents such as pentane, hexane, heptane, benzene, toluene, and xylene; halogen-based solvents such as dichloromethane, chloroform, and hydrocarbon tetrachloride; nitrile-based solvents such as acetonitrile and propionitrile; ether-based solvents such as diethylether, dioxane, and tetrahydrofuran; amide-based solvents such as N,N-dimethylformamide, N,N-dimethylacetamide, and N-methyl pyrrolidone; sulfoxide-based solvents such as dimethyl sulfoxide; water; and a mixed solvent thereof.

The reaction temperature of the reaction is usually within a range from $-70°$ C. to $+200°$ C., and preferably from $-20°$ C. to $+100°$ C.

The reaction time varies depending on the reaction scale, but is usually within a range from 30 minutes to 24 hours.

Salts of the compound represented by formula (1) can be prepared by reacting the compound represented by formula (1) with an acid by a conventional method.

After completion of any reaction, the objective compound represented by formula (1) and a salt thereof can be isolated by performing a usual work-up operation. If it is necessary to purify the product, conventionally known purification means such as distillation, recrystallization or column chromatography can be employed.

Specific examples of the thus prepared tetrazoyloxime derivative represented by formula (1) of the present invention are shown in Table 1 to Table 4 shown below. Abbreviations in the tables have meanings shown below. Me: methyl, Et: ethyl, Pr: propyl, Bu: butyl, Hex: hexyl, i: iso, n: normal, s: secondary, t: tertiary, c: cyclo, Ph: phenyl, and Py: pyridyl

TABLE 1

| No | Z | $R_{n2}$ | $(X)_{n1}$ | mp °C. |
|---|---|---|---|---|
| 1-1 | H | 4-Me | — | |
| 1-2 | $NH_2$ | 4-Me | — | |
| 1-3 | $NH_2$ | 4-Bu-t | — | |
| 1-4 | $NH_2$ | 4-$OC_2H_5$ | — | |
| 1-5 | $NH_2$ | 5-$CH_3$ | — | |
| 1-6 | $NH_2$ | 4-$OCH_3$ | — | |
| 1-7 | $NH_2$ | 4-$C_2H_5$ | — | |
| 1-8 | NHCHO | 4-Me | — | |
| 1-9 | $NHCOCH_3$ | 4-Me | — | |
| 1-10 | $NHCOC_2H_5$ | 4-Me | — | |
| 1-11 | NHCOPr-n | 4-Me | — | |
| 1-12 | NHCOPr-i | 4-Me | — | |
| 1-13 | NHCOBu-n | 4-Me | — | |
| 1-14 | NHCOBu-i | 4-Me | — | |
| 1-15 | NHCOBu-s | 4-Me | — | |
| 1-16 | NHCOBu-t | 4-Me | — | |
| 1-17 | NHCOBu-t | 4-OMe | — | |
| 1-18 | $NHCOCH_2CF_3$ | 4-Me | — | |
| 1-19 | $NHCOC_2H_5$ | 4-Me | — | |
| 1-20 | $NHCOCH_2CH_2F$ | 4-Me | — | |
| 1-21 | $NHCOC(CH_3)_2CF_3$ | 4-Me | — | |
| 1-22 | $NHCOCH_2CH_2CF_3$ | 4-Me | — | |
| 1-23 | $NHCOCH_2C_2F_5$ | 4-Me | — | |
| 1-24 | $NHCOCH_2CH=CH_2$ | 4-Me | — | |
| 1-25 | $NHCOCH_2CH=CMe_2$ | 4-Me | — | |
| 1-26 | $NHCOC(CH_3)_2CH=CH_2$ | 4-Me | — | |
| 1-27 | $NHCOC(CH_3)_2CH=CHCH_3$ | 4-Me | — | |
| 1-28 | $NHCOCH_2CH=CHCl$ | 4-Me | — | |
| 1-29 | $NHCOCH_2CH=CHCF_3$ | 4-Me | — | |
| 1-30 | $NHCOCH_2Cl=Cl_2$ | 4-Me | — | |
| 1-31 | NHCO(1,1-dimethyl-2-propynyl) | 4-Me | — | |
| 1-32 | NHCO(2-butynyl) | 4-Me | — | |
| 1-33 | NHCO(1,1-dimethyl-2-butynyl) | 4-Me | — | |

TABLE 1-continued

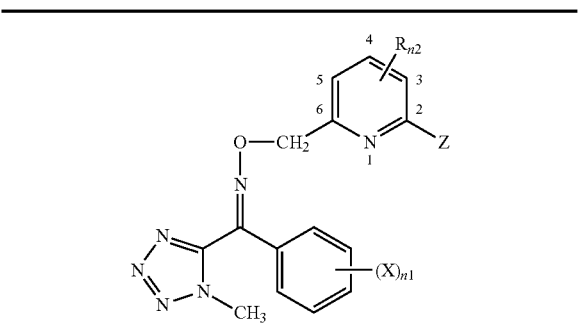
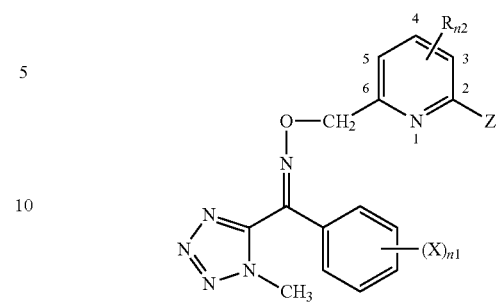

| No | Z | R$_{n2}$ | (X)$_{n1}$ | mp °C. |
|---|---|---|---|---|
| 1-34 | NHCO(1,1-dimethyl-2-pentynyl) | 4-Me | — | |
| 1-35 | NHCO(1-propynyl) | 4-Me | — | |
| 1-36 | NHCO(1,1-dimethyl-3-Iodo-2-pentynyl) | 4-Me | — | |
| 1-37 | NHCO(4,4,4-trifluoro-2-butynyl) | 4-Me | — | |
| 1-38 | NHCOPr-c | 4-Me | — | |
| 1-39 | NHCOHex-c | 4-Me | — | |
| 1-40 | NHCO(CH$_2$)$_4$CO$_2$H | 4-Me | — | |
| 1-41 | NHCOCH$_2$CH$_2$NHCOBu-t | 4-Me | — | |
| 1-42 | NHCOCH$_2$CH$_2$NHCO$_2$Et | 4-Me | — | |
| 1-43 | NHCOCH$_2$CH$_2$CH$_2$NHCOCH$_3$ | 4-Me | — | |
| 1-44 | NHCOCH$_2$CH$_2$CH$_2$NHMe | 4-Me | — | |
| 1-45 | NHCOCH$_2$CH$_2$N(Me)COCH$_3$ | 4-Me | — | |
| 1-46 | NHCOCH$_2$CH$_2$NHCOPh | 4-Me | — | |
| 1-47 | NHCOCH$_2$CH$_2$N(Me)COPh | 4-Me | — | |
| 1-48 | NHCOCH$_2$CH$_2$NHPh | 4-Me | — | |
| 1-49 | NHCO(CH$_2$)$_4$NH$_2$ | 4-Me | — | |
| 1-50 | NHCOCH$_2$NHCH$_2$Ph | 4-Me | — | |
| 1-51 | NHCOCH$_2$N(CH$_2$Ph)(CO$_2$Bu-t) | 4-Me | — | |
| 1-52 | NHCOCH$_2$CH$_2$OC$_6$H$_4$Cl-4 | 4-Me | — | |
| 1-53 | NHCOCH$_2$OPh | 4-Me | — | |
| 1-54 | NHCOCH$_2$OC$_6$H$_4$F-3 | 4-Me | — | |
| 1-55 | NHCOCH$_2$OC$_6$H$_4$OCF$_3$-3 | 4-Me | — | |
| 1-56 | NHCO(CH$_2$)$_4$SMe | 4-Me | — | |
| 1-57 | NHCOCH$_2$OEt | 4-Me | — | |
| 1-58 | NHCOCH$_2$CH$_2$OPr-i | 4-Me | — | |
| 1-59 | NHCOCH$_2$CH$_2$OBu-i | 4-Me | — | |
| 1-60 | NHCOCH$_2$CH$_2$OCH$_2$CH$_2$OMe | 4-Me | — | |
| 1-61 | NHCO$_2$CH$_3$ | 4-Me | — | |
| 1-62 | NHCO$_2$C$_2$H$_5$ | 4-Me | — | |
| 1-63 | NHCO$_2$Pr-n | 4-Me | — | |
| 1-64 | NHCO$_2$Pr-i | 4-Me | — | |
| 1-65 | NHCO$_2$Bu-i | 4-Me | — | |
| 1-66 | NHCO$_2$Bu-n | 4-Me | — | |
| 1-67 | NHCO$_2$Bu-s | 4-Me | — | |
| 1-68 | NHCO$_2$Bu-t | 4-i-Pr | — | 68-70 |
| 1-69 | NHCO$_2$Bu-t | 5-Me | — | 60-63 |
| 1-70 | NHCO$_2$Bu-t | 4-t-Bu | — | 68-69 |
| 1-71 | NHCO$_2$Bu-t | 4-Me | — | |
| 1-72 | NHCO$_2$Bu-t | 4-Et | — | 42-46 |
| 1-73 | NHCO$_2$Bu-t | 4-CH=CH2 | — | |
| 1-74 | NHCO$_2$Bu-t | 4-OMe | — | 151-153 |
| 1-75 | NHCO$_2$Bu-t | 4-OEt | — | 54-55 |
| 1-76 | NHCO$_2$Bu-t | 4-OCH$_2$CH$_2$OEt | — | <50 |
| 1-77 | NHCO$_2$Bu-t | 4-OPr-i | — | |
| 1-78 | NHCO$_2$Bu-t | 4-OBu-n | — | |
| 1-79 | NHCO$_2$Bu-t | 4-SMe | — | 142-144 |
| 1-80 | NHCO$_2$Bu-t | 4-SOMe | — | 86-88 |
| 1-81 | NHCO$_2$Bu-t | 4-SO$_2$Me | — | 117-118 |
| 1-82 | NHCO$_2$Bu-t | 4-NMe$_2$ | — | |
| 1-83 | NHCO$_2$Bu-t | 4-N(Me)(CO$_2$Bu-t) | — | |
| 1-84 | NHCO$_2$Bu-t | 5-CN | — | 68-72 |
| 1-85 | NHCO$_2$Bu-t | 4-CN | — | 70-75 |
| 1-86 | NHCO$_2$Bu-t | 4-morpholino | — | |
| 1-87 | NHCO$_2$Bu-t | 5-Ph | — | 99-102 |
| 1-88 | NHCO$_2$Bu-t | 5-CO$_2$C$_2$H$_5$ | — | 74-77 |
| 1-89 | NHCO$_2$Bu-t | 5-CONHCH$_3$ | — | |
| 1-90 | NHCO$_2$Bu-t | CF$_3$ | — | |
| 1-91 | NHCO$_2$Bu-t | 5-OH | — | |
| 1-92 | NHCO$_2$Bu-t | 5-SH | — | |
| 1-93 | NHCO$_2$Bu-t | 4-CH$_2$Cl=Cl$_2$ | — | |
| 1-94 | NHCO$_2$Bu-t | 4-etynyl | — | |
| 1-95 | NHCO$_2$Bu-t | 4-propargyl | — | |
| 1-96 | NHCO$_2$Bu-t | 4-(3-iodo-2-propynyl) | — | |
| 1-97 | NHCO$_2$Bu-t | 4-Ph | — | |
| 1-98 | NHCO$_2$Bu-t | 4-C$_6$H$_4$OMe-4 | — | |
| 1-99 | NHCO$_2$Bu-t | 4-(2-pyridyl) | — | |
| 1-100 | NHCO$_2$Bu-t | 4-(4-CH$_3$-2-oxazolyl) | — | |
| 1-101 | NHCO$_2$Bu-t | 4-(3-CF$_3$-5-Cl-2-pyridyl) | — | |
| 1-102 | NHCO$_2$Bu-t | 4-pyrrolidino | — | |
| 1-103 | NHCO$_2$Bu-t | 4-COMe | — | |
| 1-104 | NHCO$_2$Bu-t | 4-CONHMe | — | |
| 1-105 | NHCO$_2$Bu-t | 4-CONMe$_2$ | — | |
| 1-106 | NHCO$_2$Bu-t | 4-COPr-c | — | |
| 1-107 | NHCO$_2$Bu-t | 4-COPh | — | |
| 1-108 | NHCO$_2$Bu-t | 4-COCH$_2$CH=CH$_2$ | — | |
| 1-109 | NHCO$_2$Bu-t | 4-CO(propargyl) | — | |
| 1-110 | NHCO$_2$Bu-t | 4-CO$_2$Me | — | |
| 1-111 | NHCO$_2$Bu-t | 4-CO$_2$Ph | — | |
| 1-112 | NHCO$_2$Bu-t | 4-CO$_2$CH$_2$CH=CH$_2$ | — | |
| 1-113 | NHCO$_2$Bu-t | 4-CO$_2$(propargyl) | — | |
| 1-114 | NHCO$_2$Bu-t | 4-Me | 2-Cl | |
| 1-115 | NHCO$_2$Bu-t | 4-Me | 3-Cl | |
| 1-116 | NHCO$_2$Bu-t | 4-Me | 4-Cl | |
| 1-117 | NHCO$_2$Bu-t | 4-Me | 2,4-Cl$_2$ | |
| 1-118 | NHCO$_2$Bu-t | 4-Me | 3,5-Cl$_2$ | |
| 1-119 | NHCO$_2$Bu-t | 4-Me | 3,4,5-Cl$_3$ | |
| 1-120 | NHCO$_2$Bu-t | 4-Me | 2-Me | |
| 1-121 | NHCO$_2$Bu-t | 3,4-diMe | | |
| 1-122 | NHCO$_2$Bu-t | 3,5-diMe | | |
| 1-123 | NHCO$_2$Bu-t | 4,5-diMe | | |
| 1-124 | NHCO$_2$Bu-t | 3,4,5-triMe | | |
| 1-125 | NHCO$_2$Bu-t | 3-Cl-4-Me | | |
| 1-126 | NHCO$_2$Bu-t | 5-Cl-4-Me | | |
| 1-127 | NHCO$_2$Bu-t | 3,5-diCl-4-Me | | |
| 1-128 | NHCO$_2$Bu-t | 3,5-diCl | | |
| 1-129 | NHCO$_2$Bu-t | 3,4-diCl | | |
| 1-130 | NHCO$_2$Bu-t | 3,4-diF | | |
| 1-131 | NHCO$_2$Bu-n | 4-NH$_2$ | | |
| 1-132 | NHCO$_2$Bu-n | 4-NHCO$_2$Bu-t | | |
| 1-133 | NHCO$_2$CH$_2$CF$_3$ | 4-Me | | |
| 1-134 | NHCO$_2$C$_2$F$_5$ | 4-Me | | |
| 1-135 | NHCO$_2$CH$_2$CH$_2$F | 4-Me | | |
| 1-136 | NHCO$_2$C(CH$_3$)$_2$CF$_3$ | 4-Me | | |
| 1-137 | NHCO$_2$CH$_2$CH$_2$CF$_3$ | 4-Me | | |
| 1-138 | NHCO$_2$CH$_2$C$_2$F$_5$ | 4-Me | | |
| 1-139 | NHCO$_2$CH$_2$CH=CH$_2$ | 4-Me | | |

TABLE 1-continued

| No | Z | $R_{n2}$ | $(X)_{n1}$ | mp °C. |
|---|---|---|---|---|
| 1-140 | NHCO$_2$CH$_2$CH=CMe$_2$ | 4-Me | | — |
| 1-141 | NHCO$_2$C(CH$_3$)$_2$CH=CH$_2$ | 4-Me | | — |
| 1-142 | NHCO$_2$C(CH$_3$)$_2$CH=CHCH$_3$ | 4-Me | | — |
| 1-143 | NHCO$_2$CH$_2$CH=CHCl | 4-Me | | — |
| 1-144 | NHCO$_2$CH$_2$CH=CHCF$_3$ | 4-Me | | — |
| 1-145 | NHCO$_2$CH$_2$Cl=Cl$_2$ | 4-Me | | — |
| 1-146 | NHCO$_2$(1,1-dimethyl-2-propynyl) | 4-Me | | — |
| 1-147 | NHCO$_2$(2-butynyl) | 4-Me | | — |
| 1-148 | NHCO$_2$(1,1-dimethyl-2-butynyl) | 4-Me | | — |
| 1-149 | NHCO$_2$(1,1-dimethyl-2-pentynyl) | 4-Me | | — |
| 1-150 | NHCO$_2$(1-propynyl) | 4-Me | | — |
| 1-151 | NHCO$_2$(1,1-dimethyl-3-Iodo-2-pentynyl) | 4-Me | | — |
| 1-152 | NHCO$_2$(4,4,4-trifluoro-2-butynyl) | 4-Me | | — |
| 1-153 | NHCO$_2$Pr-c | 4-Me | | — |
| 1-154 | NHCO$_2$Hex-c | 4-Me | | — |
| 1-155 | NHCO$_2$CH$_2$CH$_2$NHCO$_2$Bu-t | 4-Me | | — |
| 1-156 | NHCO$_2$CH$_2$CH$_2$NHCO$_2$Et | 4-Me | | — |
| 1-157 | NHCO$_2$CH$_2$CH$_2$CH$_2$NHCOCH$_3$ | 4-Me | | — |
| 1-158 | NHCO$_2$CH$_2$CH$_2$CH$_2$NHMe$_2$ | 4-Me | | — |
| 1-159 | NHCO$_2$CH$_2$CH$_2$CH$_2$N(Me)COCH$_3$ | 4-Me | | — |
| 1-160 | NHCO$_2$CH$_2$CH$_2$CH$_2$NHCOPh | 4-Me | | — |
| 1-161 | NHCO$_2$CH$_2$CH$_2$CH$_2$N(Me)COPh | 4-Me | | — |
| 1-162 | NHCO$_2$CH$_2$CH$_2$NHPh | 4-Me | | — |
| 1-163 | NHCO$_2$(CH$_2$)$_4$NH$_2$ | 4-Me | | — |
| 1-164 | NHCO$_2$CH$_2$NHCH$_2$Ph | 4-Me | | — |
| 1-165 | NHCO$_2$CH$_2$N(CH$_2$Ph)(CO$_2$Bu-t) | 4-Me | | — |
| 1-166 | NHCO$_2$CH$_2$C$_3$H$_5$-c | 4-Me | | — |
| 1-167 | NHCO$_2$CH(CH$_3$)C$_3$H$_5$-c | 4-Me | | — |
| 1-168 | NHCO$_2$CH$_2$C$_6$H$_{11}$-c | 4-Me | | — |
| 1-169 | NHCO$_2$CH$_2$Ph | 4-Me | | — |
| 1-170 | NHCO$_2$CH(CH$_3$)CH$_2$Ph | 4-Me | | — |
| 1-171 | NHCO$_2$CH(CH$_3$)Ph | 4-Me | | — |
| 1-172 | NHCO$_2$C(CH$_3$)$_2$Ph | 4-Me | | — |
| 1-173 | NHCO$_2$CH$_2$C$_6$H$_4$CF$_3$-4 | 4-Me | | — |
| 1-174 | NHCO$_2$CH$_2$C$_6$H$_4$CN-4 | 4-Me | | — |
| 1-175 | NHCO$_2$CH$_2$C$_6$H$_4$CN-3 | 4-Me | | — |
| 1-176 | NHCO$_2$CH$_2$C$_6$H$_4$Cl-4 | 4-Me | | — |
| 1-177 | NHCO$_2$CH$_2$C$_6$H$_4$Cl-3 | 4-Me | | — |
| 1-178 | NHCO$_2$CH$_2$C$_6$H$_4$OMe-3 | 4-Me | | — |
| 1-179 | NHCO$_2$CH$_2$C$_6$H$_4$OMe-2 | 4-Me | | — |
| 1-180 | NHCO$_2$CH$_2$C$_6$H$_4$Me-4 | 4-Me | | — |
| 1-181 | NHCO$_2$CH$_2$C$_6$H$_4$Me-3 | 4-Me | | — |
| 1-182 | NHCO$_2$CH$_2$C$_6$H$_4$Me-2 | 4-Me | | — |
| 1-183 | NHCO$_2$CH$_2$C$_6$H$_4$SO$_2$Me-4 | 4-Me | | — |
| 1-184 | NHCO$_2$CH$_2$C$_6$H$_4$SO$_2$Me-3 | 4-Me | | — |
| 1-185 | NHCO$_2$CH$_2$C$_6$H$_4$Ph-4 | 4-Me | | — |
| 1-186 | NHCO$_2$CH$_2$C$_6$H$_4$Ph-3 | 4-Me | | — |
| 1-187 | NHCO$_2$CH$_2$Py-2 | 4-Me | | — |
| 1-188 | NHCO$_2$CH$_2$(6-Me-2-Py) | 4-Me | | — |
| 1-189 | NHCO$_2$C(CH$_3$)$_2$Py-4 | 4-Me | | — |
| 1-190 | NHCO$_2$CH$_2$(2-thiazolyl) | 4-Me | | — |
| 1-191 | NHCO$_2$CH$_2$(2-benzthiazolyl) | 4-Me | | — |
| 1-192 | NHCO$_2$CH$_2$CH$_2$OMe | 4-Me | | — |
| 1-193 | NHCO$_2$CH$_2$CH$_2$OEt | 4-Me | | — |
| 1-194 | NHCO$_2$CH$_2$CH$_2$OPr-i | 4-Me | | — |
| 1-195 | NHCO$_2$CH$_2$CH$_2$OBu-i | 4-Me | | — |
| 1-196 | NHCO$_2$CH$_2$CH$_2$OCH$_2$OMe | 4-Me | | — |
| 1-197 | NHCO$_2$CH$_2$CH$_2$OEt | 4-i-Pr | | — |
| 1-198 | NHCO$_2$CH$_2$CH$_2$OC$_6$H$_4$Cl-4 | 4-Me | | — |
| 1-199 | NHCOCH$_2$OPh | 4-Me | | — |
| 1-200 | NHCOCH$_2$OC$_6$H$_4$F-3 | 4-Me | | — |
| 1-201 | NHCOCH$_2$OC$_6$H$_4$OCF$_3$-3 | 4-Me | | — |
| 1-202 | NHCO$_2$CH$_2$CH$_2$OCH$_2$Ph | 4-Me | | — |
| 1-203 | NHCO$_2$CH$_2$CH$_2$OCH$_2$CH$_2$Ph | 4-Me | | — |
| 1-204 | NHCO$_2$(1,1-dimethyl-3-phenyl-2-pentynyl) | 4-Me | | — |
| 1-205 | NHCO$_2$(CH$_2$)$_4$SMe | 4-Me | | — |
| 1-206 | NHCO$_2$(CH$_2$)$_4$SCF$_3$ | 4-Me | | — |
| 1-207 | NHCO$_2$(CH$_2$)$_4$SPh | 4-Me | | — |
| 1-208 | NHCO$_2$(CH$_2$)$_4$SOMe | 4-Me | | — |
| 1-209 | NHCO$_2$(CH$_2$)$_4$SOCF$_3$ | 4-Me | | — |
| 1-210 | NHCO$_2$(CH$_2$)$_4$SOPh | 4-Me | | — |
| 1-211 | NHCO$_2$(CH$_2$)$_4$SO$_2$Me | 4-Me | | — |
| 1-212 | NHCO$_2$(CH$_2$)$_4$SO$_2$CF$_3$ | 4-Me | | — |
| 1-213 | NHCO$_2$(CH$_2$)$_4$SO$_2$Ph | 4-Me | | — |
| 1-214 | NHCO$_2$Ph | 4-Me | | — |
| 1-215 | NHCO$_2$C$_6$H$_4$OMe-4 | 4-Me | | — |
| 1-216 | NHCONHMe | 4-Me | | — |
| 1-217 | NHCONHC$_2$H$_5$ | 4-Me | | — |
| 1-218 | NHCONHPr-n | 4-Me | | — |
| 1-219 | NHCONHBu-t | 4-Me | | — |
| 1-220 | NHCONHBu-s | 4-Me | | — |
| 1-221 | NHCONH(Hex-n) | 4-Me | | — |
| 1-222 | H | 4-Cl | | — |
| 1-223 | NH$_2$ | 4-Cl | | — |
| 1-224 | NHCHO | 4-Cl | | — |
| 1-225 | NHCOCH$_2$CF$_3$ | 4-Cl | | — |
| 1-226 | NHCO$_2$F$_5$ | 4-Cl | | — |
| 1-227 | NHCOCH$_2$F | 4-Cl | | — |
| 1-228 | NHCOC(CH$_3$)$_2$CF$_3$ | 4-Cl | | — |
| 1-229 | NHCOCH$_2$CH$_2$CF$_3$ | 4-Cl | | — |
| 1-230 | NHCOCH$_2$C$_2$F$_5$ | 4-Cl | | — |
| 1-231 | NHCOCH$_2$CH=CH$_2$ | 4-Cl | | — |
| 1-232 | NHCOCH$_2$CH=CMe$_2$ | 4-Cl | | — |
| 1-233 | NHCOC(CH$_3$)$_2$CH=CH$_2$ | 4-Cl | | — |
| 1-234 | NHCOC(CH$_3$)$_2$CH=CHCH$_3$ | 4-Cl | | — |
| 1-235 | NHCOCH$_2$CH=CHCl | 4-Cl | | — |
| 1-236 | NHCOCH$_2$CH=CHCF$_3$ | 4-Cl | | — |
| 1-237 | NHCOCH$_2$Cl=Cl$_2$ | 4-Cl | | — |
| 1-238 | NHCO(1,1-dimethyl-2-propynyl) | 4-Cl | | — |
| 1-239 | NHCO(2-butynyl) | 4-Cl | | — |
| 1-240 | NHCO(1,1-dimethyl-2-butynyl) | 4-Cl | | — |
| 1-241 | NHCO(1,1-dimethyl-2-pentynyl) | 4-Cl | | — |
| 1-242 | NHCO(1-propynyl) | 4-Cl | | — |
| 1-243 | NHCO(1,1-dimethyl-3-Iodo-2-pentynyl) | 4-Cl | | — |
| 1-244 | NHCO(4,4,4-trifluoro-2-butynyl) | 4-Cl | | — |
| 1-245 | NHCOPr-c | 4-Cl | | — |
| 1-246 | NHCOHex-c | 4-Cl | | — |
| 1-247 | NHCO(CH$_2$)$_4$CO$_2$H | 4-Cl | | — |
| 1-248 | NHCOCH$_2$CH$_2$NHCO$_2$Bu-t | 4-Cl | | — |
| 1-249 | NHCOCH$_2$CH$_2$NHCO$_2$Et | 4-Cl | | — |
| 1-250 | NHCOCH$_2$CH$_2$CH$_2$NHCOCH$_3$ | 4-Cl | | — |

TABLE 1-continued

| No | Z | $R_{n2}$ | $(X)_{n1}$ | mp °C. |
|---|---|---|---|---|
| 1-251 | NHCOCH$_2$CH$_2$CH$_2$NHMe | 4-Cl | — | |
| 1-252 | NHCOCH$_2$CH$_2$N(Me)COCH$_3$ | 4-Cl | — | |
| 1-253 | NHCOCH$_2$CH$_2$NHCOPh | 4-Cl | — | |
| 1-254 | NHCOCH$_2$CH$_2$N(Me)COPh | 4-Cl | — | |
| 1-255 | NHCOCH$_2$CH$_2$NHPh | 4-Cl | — | |
| 1-256 | NHCO(CH$_2$)$_4$NH$_2$ | 4-Cl | — | |
| 1-257 | NHCOCH$_2$NHCH$_2$Ph | 4-Cl | — | |
| 1-258 | NHCOCH$_2$N(CH$_2$Ph)(CO$_2$Bu-t) | 4-Cl | — | |
| 1-259 | NHCOCH$_2$OC$_6$H$_4$Cl-4 | 4-Cl | — | |
| 1-260 | NHCOCH$_2$OPh | 4-Cl | — | |
| 1-261 | NHCOCH$_2$OC$_6$H$_4$F-3 | 4-Cl | — | |
| 1-262 | NHCOCH$_2$OC$_6$H$_4$OCF$_3$-3 | 4-Cl | — | |
| 1-263 | NHCO(CH$_2$)$_4$SMe | 4-Cl | — | |
| 1-264 | NHCOCH$_2$OEt | 4-Cl | — | |
| 1-265 | NHCOCH$_2$CH$_2$OPr-i | 4-Cl | — | |
| 1-266 | NHCOCH$_2$CH$_2$OBu-i | 4-Cl | — | |
| 1-267 | NHCOCH$_2$CH$_2$OCH$_2$CH$_2$OMe | 4-Cl | — | |
| 1-268 | NHCO$_2$CH$_3$ | 4-Cl | — | |
| 1-269 | NHCO$_2$C$_2$H$_5$ | 4-Cl | — | |
| 1-270 | NHCO$_2$Pr-n | 4-Cl | — | |
| 1-271 | NHCO$_2$Pr-i | 4-Cl | — | |
| 1-272 | NHCO$_2$Bu-n | 4-Cl | — | |
| 1-273 | NHCO$_2$Bu-i | 4-Cl | — | |
| 1-274 | NHCO$_2$Bu-s | 4-Cl | — | |
| 1-275 | NHCO$_2$Bu-t | 4-Cl | — | |
| 1-276 | NHCO$_2$Bu-t | 5-Br | — | 58-61 |
| 1-277 | NHCO$_2$Bu-t | 5-Cl | — | 38-41 |
| 1-278 | NHCO$_2$Bu-t | 4-Br | — | |
| 1-279 | NHCO$_2$Bu-t | 4-Cl | 2-Cl | |
| 1-280 | NHCO$_2$Bu-t | 4-Cl | 3-Cl | |
| 1-281 | NHCO$_2$Bu-t | 4-Cl | 4-Cl | |
| 1-282 | NHCO$_2$Bu-t | 4-Cl | 2,4-Cl$_2$ | |
| 1-283 | NHCO$_2$Bu-t | 4-Cl | 3,5-Cl$_2$ | |
| 1-284 | NHCO$_2$Bu-t | 4-Cl | 3,4,5-Cl$_3$ | |
| 1-285 | NHCO$_2$Bu-t | 4-Cl | 2-Me | |
| 1-286 | NHCO$_2$CH$_2$CF$_3$ | 4-Cl | — | |
| 1-287 | NHCO$_2$C$_2$F$_5$ | 4-Cl | — | |
| 1-288 | NHCO$_2$CH$_2$CH$_2$F | 4-Cl | — | |
| 1-289 | NHCO$_2$C(CH$_3$)$_2$CF$_3$ | 4-Cl | — | |
| 1-290 | NHCO$_2$CH$_2$CH$_2$CF$_3$ | 4-Cl | — | |
| 1-291 | NHCO$_2$CH$_2$C$_2$F$_5$ | 4-Cl | — | |
| 1-292 | NHCO$_2$CH$_2$CH=CH$_2$ | 4-Cl | — | |
| 1-293 | NHCO$_2$CH$_2$CH=CMe$_2$ | 4-Cl | — | |
| 1-294 | NHCO$_2$C(CH$_3$)$_2$CH=CH$_2$ | 4-Cl | — | |
| 1-295 | NHCO$_2$CH(CH$_3$)CH=CHCH$_3$ | 4-Cl | — | |
| 1-296 | NHCO$_2$CH$_2$CH=CHCl | 4-Cl | — | |
| 1-297 | NHCO$_2$CH$_2$CH=CHCF$_3$ | 4-Cl | — | |
| 1-298 | NHCO$_2$CH$_2$Cl=Cl$_2$ | 4-Cl | — | |
| 1-299 | NHCO$_2$(1,1-dimethyl-2-propynyl) | 4-Cl | — | |
| 1-300 | NHCO$_2$(2-butynyl) | 4-Cl | — | |
| 1-301 | NHCO$_2$(1,1-dimethyl-2-butynyl) | 4-Cl | — | |
| 1-302 | NHCO$_2$(1,1-dimethyl-2-pentynyl) | 4-Cl | — | |
| 1-303 | NHCO$_2$(1-propynyl) | 4-Cl | — | |
| 1-304 | NHCO$_2$(1,1-dimethyl-3-Iodo-2-pentynyl) | 4-Cl | — | |
| 1-305 | NHCO$_2$(4,4,4-trifluoro-2-butynyl) | 4-Cl | — | |
| 1-306 | NHCO$_2$Pr-c | 4-Cl | — | |
| 1-307 | NHCO$_2$Hex-c | 4-Cl | — | |
| 1-308 | NHCO$_2$CH$_2$CH$_2$NHCO$_2$Bu-t | 4-Cl | — | |
| 1-309 | NHCO$_2$CH$_2$CH$_2$NHCO$_2$Et | 4-Cl | — | |
| 1-310 | NHCO$_2$CH$_2$CH$_2$CH$_2$NHCOCH$_3$ | 4-Cl | — | |
| 1-311 | NHCO$_2$CH$_2$CH$_2$CH$_2$NMe$_2$ | 4-Cl | — | |
| 1-312 | NHCO$_2$CH$_2$CH$_2$N(Me)COCH$_3$ | 4-Cl | — | |
| 1-313 | NHCO$_2$CH$_2$CH$_2$NHCOPh | 4-Cl | — | |
| 1-314 | NHCO$_2$CH$_2$CH$_2$N(Me)COPh | 4-Cl | — | |
| 1-315 | NHCO$_2$CH$_2$CH$_2$NHPh | 4-Cl | — | |
| 1-316 | NHCO$_2$(CH$_2$)$_4$NH$_2$ | 4-Cl | — | |
| 1-317 | NHCO$_2$CH$_2$NHCH$_2$Ph | 4-Cl | — | |
| 1-318 | NHCO$_2$CH$_2$N(CH$_2$Ph)(CO$_2$Bu-t) | 4-Cl | — | |
| 1-319 | NHCO$_2$CH$_2$C$_3$H$_5$-c | 4-Cl | — | |
| 1-320 | NHCO$_2$CH(CH$_3$)C$_3$H$_5$-c | 4-Cl | — | |
| 1-321 | NHCO$_2$CH$_2$C$_6$H$_{11}$-c | 4-Cl | — | |
| 1-322 | NHCO$_2$CH$_2$Ph | 4-Cl | — | |
| 1-323 | NHCO$_2$CH$_2$Ph | 5-Cl | — | 109-110 |
| 1-324 | NHCO$_2$CH(CH$_3$)CH$_2$Ph | 4-Cl | — | |
| 1-325 | NHCO$_2$CH(CH$_3$)Ph | 4-Cl | — | |
| 1-326 | NHCO$_2$C(CH$_3$)$_2$Ph | 4-Cl | — | |
| 1-327 | NHCO$_2$CH$_2$C$_6$H$_4$CF$_3$-4 | 4-Cl | — | |
| 1-328 | NHCO$_2$CH$_2$C$_6$H$_4$CN-4 | 4-Cl | — | |
| 1-329 | NHCO$_2$CH$_2$C$_6$H$_4$CN-3 | 4-Cl | — | |
| 1-330 | NHCO$_2$CH$_2$C$_6$H$_4$Cl-4 | 4-Cl | — | |
| 1-331 | NHCO$_2$CH$_2$C$_6$H$_4$Cl-3 | 4-Cl | — | |
| 1-332 | NHCO$_2$CH$_2$C$_6$H$_4$OMe-3 | 4-Cl | — | |
| 1-333 | NHCO$_2$CH$_2$C$_6$H$_4$OMe-2 | 4-Cl | — | |
| 1-334 | NHCO$_2$CH$_2$C$_6$H$_4$Me-4 | 4-Cl | — | |
| 1-335 | NHCO$_2$CH$_2$C$_6$H$_4$Me-3 | 4-Cl | — | |
| 1-336 | NHCO$_2$CH$_2$C$_6$H$_4$Me-2 | 4-Cl | — | |
| 1-337 | NHCO$_2$CH$_2$C$_6$H$_4$SO$_2$Me-4 | 4-Cl | — | |
| 1-338 | NHCO$_2$CH$_2$C$_6$H$_4$SO$_2$Me-3 | 4-Cl | — | |
| 1-339 | NHCO$_2$CH$_2$C$_6$H$_4$Ph-4 | 4-Cl | — | |
| 1-340 | NHCO$_2$CH$_2$C$_6$H$_4$Ph-3 | 4-Cl | — | |
| 1-341 | NHCO$_2$CH$_2$Py-2 | 4-Cl | — | |
| 1-342 | NHCO$_2$CH$_2$(6-Me-2-Py) | 4-Cl | — | |
| 1-343 | NHCO$_2$C(CH$_3$)$_2$Py-4 | 4-Cl | — | |
| 1-344 | NHCO$_2$CH$_2$(2-thiazolyl) | 4-Cl | — | |
| 1-345 | NHCO$_2$CH$_2$(2-benzthiazolyl) | 4-Cl | — | |
| 1-346 | NHCO$_2$CH$_2$CH$_2$OMe | 4-Cl | — | |
| 1-347 | NHCO$_2$CH$_2$CH$_2$OEt | 4-Cl | — | |
| 1-348 | NHCO$_2$CH$_2$CH$_2$OPr-i | 4-Cl | — | |
| 1-349 | NHCO$_2$CH$_2$CH$_2$OBu-i | 4-Cl | — | |
| 1-350 | NHCO$_2$CH$_2$CH$_2$OCH$_2$CH$_2$OMe | 4-Cl | — | |
| 1-351 | NHCO$_2$CH$_2$CH$_2$OC$_6$H$_4$Cl-4 | 4-Cl | — | |
| 1-352 | NHCOCH$_2$OPh | 4-Cl | — | |
| 1-353 | NHCOCH$_2$OC$_6$H$_4$F-3 | 4-Cl | — | |
| 1-354 | NHCOCH$_2$OC$_6$H$_4$OCF$_3$-3 | 4-Cl | — | |
| 1-355 | NHCO$_2$CH$_2$CH$_2$OCH$_2$Ph | 4-Cl | — | |
| 1-356 | NHCO$_2$(1,1-dimethyl-3-phenyl-2-pentynyl) | 4-Cl | — | |
| 1-357 | NHCO$_2$CH$_2$CH$_2$OCH$_2$CH$_2$Ph | 4-Cl | — | |
| 1-358 | NHCO$_2$(1,1-dimethyl-3-phenyl-2-pentynyl) | 4-Cl | — | |
| 1-359 | NHCO$_2$(CH$_2$)$_4$SMe | 4-Cl | — | |
| 1-360 | NHCO$_2$(CH$_2$)$_4$SCF$_3$ | 4-Cl | — | |
| 1-361 | NHCO$_2$(CH$_2$)$_4$SPh | 4-Cl | — | |
| 1-362 | NHCO$_2$(CH$_2$)$_4$SOMe | 4-Cl | — | |
| 1-363 | NHCO$_2$(CH$_2$)$_4$SOCF$_3$ | 4-Cl | — | |

TABLE 1-continued

| No | Z | R$_{n2}$ | (X)$_{n1}$ | mp °C. |
|---|---|---|---|---|
| 1-364 | NHCO$_2$(CH$_2$)$_4$SOPh | 4-Cl | — | |
| 1-365 | NHCO$_2$(CH$_2$)$_4$SO$_2$Me | 4-Cl | — | |
| 1-366 | NHCO$_2$(CH$_2$)$_4$SO$_2$CF$_3$ | 4-Cl | — | |
| 1-367 | NHCO$_2$(CH$_2$)$_4$SOCF$_3$ | 4-Cl | — | |
| 1-368 | NHCO$_2$Ph | 4-Cl | — | |
| 1-369 | NHCO$_2$C$_6$H$_4$OMe-4 | 4-Cl | — | |
| 1-370 | NHCONHMe | 4-Cl | — | |
| 1-371 | NHCONHC$_2$H$_5$ | 4-Cl | — | |
| 1-372 | NHCONHPr-n | 4-Cl | — | |
| 1-373 | NHCONHBu-t | 4-Cl | — | |
| 1-374 | NHCONHBu-s | 4-Cl | — | |
| 1-375 | NHCONH(Hex-n) | 4-Cl | — | |
| 1-376 | NHCOCH$_2$CF$_3$ | — | — | |
| 1-377 | NHCOC$_2$F$_5$ | — | — | |
| 1-378 | NHCOCH$_2$CH$_2$F | — | — | |
| 1-379 | NHCOC(CH$_3$)$_2$CF$_3$ | — | — | |
| 1-380 | NHCOCH$_2$CH$_2$CF$_3$ | — | — | 107-109 |
| 1-381 | NHCOCH$_2$C$_2$F$_5$ | — | — | |
| 1-382 | NHCOCH$_2$CH=CH$_2$ | — | — | |
| 1-383 | NHCOCH$_2$CH=CMe$_2$ | — | — | |
| 1-384 | NHCOC(CH$_3$)$_2$CH=CH$_2$ | — | — | |
| 1-385 | NHCOC(CH$_3$)$_2$CH=CHCH$_3$ | — | — | |
| 1-386 | NHCOCH$_2$CH=CHCl | — | — | |
| 1-387 | NHCOCH$_2$CH=CHCF$_3$ | — | — | |
| 1-388 | NHCOCH$_2$Cl=Cl$_2$ | — | — | |
| 1-389 | NHCO(1,1-dimethyl-2-propynyl) | — | — | |
| 1-390 | NHCO(2-butynyl) | — | — | |
| 1-391 | NHCO(1,1-dimethyl-2-butynyl) | — | — | |
| 1-392 | NHCO(1,1-dimethyl-2-pentynyl) | — | — | |
| 1-393 | NHCO(1-propynyl) | — | — | 193-194 |
| 1-394 | NHCO(1,1-dimethyl-3-Iodo-2-pentynyl) | — | — | |
| 1-395 | NHCO(4,4-trifluoro-2-butynyl) | — | — | |
| 1-396 | NHCO(CH$_2$)$_4$CO$_2$H | — | — | 127-129 |
| 1-397 | NHCOCH$_2$CH$_2$NHMe$_2$ | — | — | |
| 1-398 | NHCO(CH$_2$)$_4$NH$_2$ | — | — | |
| 1-399 | NHCOCH$_2$NHCH$_2$Ph | — | — | |
| 1-400 | NHCOCH$_2$N(CH$_2$Ph)(CO$_2$Bu-t) | — | — | |
| 1-401 | NHCOCH$_2$NMe$_2$ | — | — | |
| 1-402 | NHCOCH$_2$NHEt | — | — | |
| 1-403 | NHCOCH$_2$NHPr-n | — | — | |
| 1-404 | NHCOCH$_2$CH$_2$OC$_6$H$_4$Cl-4 | — | — | |
| 1-405 | NHCOCH$_2$OPh | — | — | |
| 1-406 | NHCOCH$_2$OC$_6$H$_4$F-3 | — | — | 108-112 |
| 1-407 | NHCOCH$_2$OC$_6$H$_4$OCF$_3$-3 | — | — | 128-129 |
| 1-408 | NHCOCH$_2$OC$_6$H$_4$CN-2 | — | — | 198-200 |
| 1-409 | NHCOCH$_2$OC$_6$H$_4$F-4 | — | — | 86-87 |
| 1-410 | NHCOCH$_2$OC$_6$H$_3$(3,4-methylenedioxy) | — | — | 110-114 |
| 1-411 | NHCOCH$_2$OC$_6$H$_4$(CONH$_2$)-2 | — | — | |
| 1-412 | NHCOCH$_2$OC$_6$H$_3$(3,4-(OCH$_3$)$_2$) | — | — | |
| 1-413 | NHCOCH$_2$O(6-CF$_3$-pyrimidin-4-yl) | — | — | |
| 1-414 | NHCOCH$_2$O(3-Py) | — | — | oil |
| 1-415 | NHCO$_2$CH$_2$CF$_3$ | — | — | |
| 1-416 | NHCO$_2$C$_2$F$_5$ | — | — | |
| 1-417 | NHCO$_2$CH$_2$CH$_2$F | — | — | |
| 1-418 | NHCO$_2$C(CH$_3$)$_2$CF$_3$ | — | — | |
| 1-419 | NHCO$_2$CH$_2$CF$_3$ | — | — | |
| 1-420 | NHCO$_2$CH$_2$C$_2$F$_5$ | — | — | |
| 1-421 | NHCO$_2$CH$_2$CH=CH$_2$ | — | — | |
| 1-422 | NHCO$_2$CH$_2$CH=CMe$_2$ | — | — | |
| 1-423 | NHCO$_2$C(CH$_3$)$_2$CH=CH$_2$ | — | — | |
| 1-424 | NHCO$_2$C(CH$_3$)$_2$CH=CHCH$_3$ | — | — | |
| 1-425 | NHCO$_2$CH$_2$CH=CHCl | — | — | |
| 1-426 | NHCO$_2$CH$_2$CH=CHCF$_3$ | — | — | |
| 1-427 | NHCO$_2$CH$_2$Cl=Cl$_2$ | — | — | |
| 1-428 | NHCO$_2$(1,1-dimethyl-2-propynyl) | — | — | |
| 1-429 | NHCO$_2$(2-butynyl) | — | — | 37-39 |
| 1-430 | NHCO$_2$(1,1-dimethyl-2-butynyl) | — | — | |
| 1-431 | NHCO$_2$(1,1-dimethyl-2-pentynyl) | — | — | |
| 1-432 | NHCO$_2$(1-propynyl) | — | — | |
| 1-433 | NHCO$_2$(1,1-dimethyl-3-Iodo-2-pentynyl) | — | — | |
| 1-434 | NHCO$_2$(4,4-trifluoro-2-butynyl) | — | — | |
| 1-435 | NHCO$_2$(1,1-dimethyl-3-phenyl-2-pentynyl) | — | — | |
| 1-436 | NHCO$_2$CH$_2$CH$_2$NHCO$_2$Bu-t | — | — | 115-117 |
| 1-437 | NHCO$_2$CH$_2$CH$_2$NHCO$_2$Et | — | — | |
| 1-438 | NHCO$_2$CH$_2$N(CH$_2$Ph)(CO$_2$Bu-t) | — | — | |
| 1-439 | NHCO$_2$CH$_2$NCH$_2$Ph | — | — | |
| 1-440 | NHCO$_2$CH$_2$CH$_2$NCH$_2$Ph | — | — | |
| 1-441 | NHCO$_2$CH$_2$CH$_2$NCH$_2$C$_6$H$_4$Cl-4 | — | — | |
| 1-442 | NHCO$_2$CH$_2$CH$_2$NHMe | — | — | |
| 1-443 | NHCO$_2$CH$_2$C(CH$_3$)$_2$N(CH$_3$)$_2$ | — | — | |
| 1-444 | NHCO$_2$CH(CH$_3$)CH$_2$N(CH$_3$)$_2$ | — | — | |
| 1-445 | NHCO$_2$CH$_2$C$_3$H$_5$-c | — | — | |
| 1-446 | NHCO$_2$CH(CH$_3$)C$_3$H$_5$-c | — | — | |
| 1-447 | NHCO$_2$CH$_2$C$_6$H$_{11}$-c | — | — | 44-47 |
| 1-448 | NHCO$_2$CH(CH$_3$)CH$_2$Ph | — | — | |
| 1-449 | NHCO$_2$CH(CH$_3$)Ph | — | — | |
| 1-450 | NHCO$_2$C(CH$_3$)$_2$Ph | — | — | |
| 1-451 | NHCO$_2$CH$_2$C$_6$H$_4$CF$_3$-4 | — | — | |
| 1-452 | NHCO$_2$CH$_2$C$_6$H$_4$CN-4 | — | — | 55-59 |
| 1-453 | NHCO$_2$CH$_2$C$_6$H$_4$CN-3 | — | — | 45-48 |
| 1-454 | NHCO$_2$CH$_2$C$_6$H$_4$Cl-4 | — | — | 47-49 |
| 1-455 | NHCO$_2$CH$_2$C$_6$H$_4$Cl-3 | — | — | 39-44 |
| 1-456 | NHCO$_2$CH$_2$C$_6$H$_4$OMe-3 | — | — | |
| 1-457 | NHCO$_2$CH$_2$C$_6$H$_4$OMe-2 | — | — | |
| 1-458 | NHCO$_2$CH$_2$C$_6$H$_4$Me-4 | — | — | 40-45 |
| 1-459 | NHCO$_2$CH$_2$C$_6$H$_4$Me-3 | — | — | 46-49 |
| 1-460 | NHCO$_2$CH$_2$C$_6$H$_4$Me-2 | — | — | 57-60 |
| 1-461 | NHCO$_2$CH$_2$C$_6$H$_4$SO$_2$Me-4 | — | — | 66-70 |
| 1-462 | NHCO$_2$CH$_2$C$_6$H$_4$SO$_2$Me-3 | — | — | 45-50 |
| 1-463 | NHCO$_2$CH$_2$C$_6$H$_4$Ph-4 | — | — | 60-64 |
| 1-464 | NHCO$_2$CH$_2$C$_6$H$_4$Ph-3 | — | — | 59-63 |
| 1-465 | NHCO$_2$CH$_2$C$_6$H$_4$OCH$_3$-4 | — | — | |

TABLE 1-continued

| No | Z | R$_{n2}$ | (X)$_{n1}$ | mp °C. |
|---|---|---|---|---|
| 1-466 | NHCO$_2$CH$_2$C$_6$H$_3$(3,4-methylenedioxy) | — | — | |
| 1-467 | NHCO$_2$CH$_2$Py-2 | — | — | |
| 1-468 | NHCO$_2$CH$_2$(6-Me-2-Py) | — | — | 94-96 |
| 1-469 | NHCO$_2$C(CH$_3$)$_2$Py-4 | — | — | 168-169 |
| 1-470 | NHCO$_2$CH$_2$(2-thiazolyl) | — | — | |
| 1-471 | NHCO$_2$CH$_2$(2-benzthiazolyl) | — | — | |
| 1-472 | NHCO$_2$CH$_2$(3-Py) | — | — | 140-141 |
| 1-473 | NHCO$_2$CH$_2$(4-Py) | — | — | 52-55 |
| 1-474 | NHCO$_2$CH(CH$_3$)(4-Py) | — | — | |
| 1-475 | NHCO$_2$CH$_2$CH$_2$OMe | — | — | 81-82 |
| 1-476 | NHCO$_2$CH$_2$CH$_2$OEt | — | — | 89-91 |
| 1-477 | NHCO$_2$CH$_2$CH$_2$OPr-i | — | — | |
| 1-478 | NHCO$_2$CH$_2$CH$_2$OBu-i | — | — | 93-94 |
| 1-479 | NHCO$_2$CH$_2$CH$_2$OCH$_2$CH$_2$OMe | — | — | 115-117 |
| 1-480 | NHCO$_2$C(CH$_3$)$_2$CH$_2$OCH$_3$ | — | — | |
| 1-481 | NHCO$_2$CH(CH$_3$)CH$_2$OCH$_3$ | — | — | |
| 1-482 | NHCO$_2$CH$_2$CH$_2$CH$_2$OC$_6$H$_4$Cl-4 | — | — | |
| 1-483 | NHCO$_2$CH$_2$OPh | — | — | |
| 1-484 | NHCO$_2$CH$_2$OC$_6$H$_4$F-3 | — | — | |
| 1-485 | NHCO$_2$CH$_2$OC$_6$H$_4$OCF$_3$-3 | — | — | |
| 1-486 | NHCO$_2$CH$_2$CH$_2$OCH$_2$Ph | — | — | |
| 1-487 | NHCO$_2$CH$_2$CH$_2$OCH$_2$CH$_2$Ph | — | — | |
| 1-488 | NHCO$_2$(CH$_2$)$_4$SMe | — | — | |
| 1-489 | NHCO$_2$(CH$_2$)$_4$SCF$_3$ | — | — | |
| 1-490 | NHCO$_2$(CH$_2$)$_4$SPh | — | — | |
| 1-491 | NHCO$_2$(CH$_2$)$_4$SOMe | — | — | |
| 1-492 | NHCO$_2$(CH$_2$)$_4$SOCF$_3$ | — | — | |
| 1-493 | NHCO$_2$(CH$_2$)$_4$SOPh | — | — | |
| 1-494 | NHCO$_2$(CH$_2$)$_4$SO$_2$Me | — | — | 123-124 |
| 1-495 | NHCO$_2$(CH$_2$)$_4$SO$_2$CF$_3$ | — | — | |
| 1-496 | NHCO$_2$(CH$_2$)$_4$SO$_2$Ph | — | — | |
| 1-497 | NHCO$_2$Ph | — | — | 129-131 |
| 1-498 | NHCO$_2$C$_6$H$_4$OMe-4 | — | — | 179-181 |
| 1-499 | NHCOCH$_2$CH$_2$CH$_2$COCH$_3$ | — | — | |

TABLE 2

| No | Z$^{11}$ | R$^{11}$ | (X)$_{n1}$ | mp °C. |
|---|---|---|---|---|
| 2-1 | H | Me | — | |
| 2-2 | NH$_2$ | Me | — | |
| 2-3 | NH$_2$ | Bu-t | — | |
| 2-4 | NH$_2$ | OC$_2$H$_5$ | — | |
| 2-5 | NH$_2$ | OCH$_3$ | — | |
| 2-6 | NH$_2$ | C$_2$H$_5$ | — | |
| 2-7 | NHCHO | Me | — | |
| 2-8 | NHCOCH$_3$ | Me | — | |
| 2-9 | NHCOC$_2$H$_5$ | Me | — | |
| 2-10 | NHCOPr-n | Me | — | |
| 2-11 | NHCOPr-i | Me | — | |
| 2-12 | NHCOBu-n | Me | — | |
| 2-13 | NHCOBu-i | Me | — | |
| 2-14 | NHCOBu-s | Me | — | |
| 2-15 | NHCOBu-t | Me | — | |
| 2-16 | NHCOBu-t | OMe | — | |
| 2-17 | NHCOCH$_2$CF$_3$ | Me | — | |
| 2-18 | NHCOC$_2$F$_5$ | Me | — | |
| 2-19 | NHCOCH$_2$CH$_2$F | Me | — | |

TABLE 2-continued

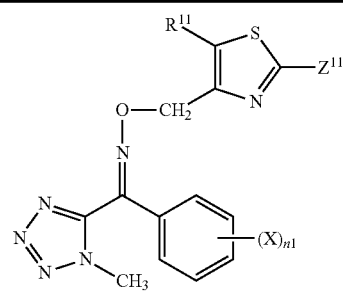

| No | $Z^{11}$ | $R^{11}$ | $(X)_{n1}$ | mp °C. |
|---|---|---|---|---|
| 2-20 | NHCOC(CH$_3$)$_2$CF$_3$ | Me | — | |
| 2-21 | NHCOCH$_2$CH$_2$CF$_3$ | Me | — | |
| 2-22 | NHCOCH$_2$C$_2$F$_5$ | Me | — | |
| 2-23 | NHCOCH$_2$CH=CH$_2$ | Me | — | |
| 2-24 | NHCOCH$_2$CH=CMe$_2$ | Me | — | |
| 2-25 | NHCOC(CH$_3$)$_2$CH=CH$_2$ | Me | — | |
| 2-26 | NHCOC(CH$_3$)$_2$CH=CHCH$_3$ | Me | — | |
| 2-27 | NHCOCH$_2$CH=CHCl | Me | — | |
| 2-28 | NHCOCH$_2$CH=CHCF$_3$ | Me | — | |
| 2-29 | NHCOCH$_2$Cl=Cl$_2$ | Me | — | |
| 2-30 | NHCO(1,1-dimethyl-2-propynyl) | Me | — | |
| 2-31 | NHCO(2-butynyl) | Me | — | |
| 2-32 | NHCO(1,1-dimethyl-2-butynyl) | Me | — | |
| 2-33 | NHCO(1,1-dimethyl-2-pentynyl) | Me | — | |
| 2-34 | NHCO(1-propynyl) | Me | — | |
| 2-35 | NHCO(1,1-dimethyl-3-Iodo-2-pentynyl) | Me | — | |
| 2-36 | NHCO(4,4,4-trifluoro-2-butynyl) | Me | — | |
| 2-37 | NHCOPr-c | Me | — | |
| 2-38 | NHCOHex-c | Me | — | |
| 2-39 | NHCO(CH$_2$)$_4$CO$_2$H | Me | — | |
| 2-40 | NHCOCH$_2$CH$_2$NHCO$_2$Bu-t | Me | — | |
| 2-41 | NHCOCH$_2$CH$_2$NHCO$_2$Et | Me | — | |
| 2-42 | NHCOCH$_2$CH$_2$CH$_2$NHCOCH$_3$ | Me | — | |
| 2-43 | NHCOCH$_2$CH$_2$CH$_2$NHMe$_2$ | Me | — | |
| 2-44 | NHCOCH$_2$CH$_2$N(Me)COCH$_3$ | Me | — | |
| 2-45 | NHCOCH$_2$CH$_2$NHCOPh | Me | — | |
| 2-46 | NHCOCH$_2$CH$_2$N(Me)COPh | Me | — | |
| 2-47 | NHCOCH$_2$CH$_2$NHPh | Me | — | |
| 2-48 | NHCO(CH$_2$)$_4$NH$_2$ | Me | — | |
| 2-49 | NHCOCH$_2$NHCH$_2$Ph | Me | — | |
| 2-50 | NHCOCH$_2$N(CH$_2$Ph)(CO$_2$Bu-t) | Me | — | |
| 2-51 | NHCOCH$_2$CH$_2$OCH$_4$Cl-4 | Me | — | |
| 2-52 | NHCOCH$_2$OPh | Me | — | |
| 2-53 | NHCOCH$_2$OC$_6$H$_4$F-3 | Me | — | |
| 2-54 | NHCOCH$_2$OC$_6$H$_4$OCF$_3$-3 | Me | — | |
| 2-55 | NHCO(CH$_2$)$_4$SMe | Me | — | |
| 2-56 | NHCOCH$_2$CH$_2$OEt | Me | — | |
| 2-57 | NHCOCH$_2$CH$_2$OPr-i | Me | — | |
| 2-58 | NHCOCH$_2$CH$_2$OBu-i | Me | — | |
| 2-59 | NHCOCH$_2$CH$_2$OCH$_2$CH$_2$OMe | Me | — | |
| 2-60 | NHCO$_2$CH$_3$ | Me | — | |
| 2-61 | NHCO$_2$C$_2$H$_5$ | Me | — | |
| 2-62 | NHCO$_2$Pr-n | Me | — | |
| 2-63 | NHCO$_2$Pr-i | Me | — | |
| 2-64 | NHCO$_2$Bu-n | Me | — | |
| 2-65 | NHCO$_2$Bu-i | Me | — | |
| 2-66 | NHCO$_2$Bu-s | Me | — | |
| 2-67 | NHCO$_2$Bu-t | i-Pr | — | |
| 2-68 | NHCO$_2$Bu-t | Me | — | |
| 2-69 | NHCO$_2$Bu-t | t-Bu | — | |
| 2-70 | NHCO$_2$Bu-t | Et | — | |
| 2-71 | NHCO$_2$Bu-t | CH=CH2 | — | |
| 2-72 | NHCO$_2$Bu-t | OMe | — | |
| 2-73 | NHCO$_2$Bu-t | OEt | — | |
| 2-74 | NHCO$_2$Bu-t | OCH$_2$CH$_2$OEt | — | |
| 2-75 | NHCO$_2$Bu-t | OPr-i | — | |
| 2-76 | NHCO$_2$Bu-t | OBu-n | — | |

TABLE 2-continued

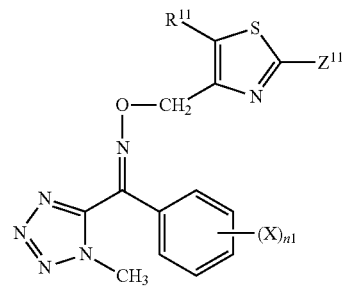

| No | $Z^{11}$ | $R^{11}$ | $(X)_{n1}$ | mp °C. |
|---|---|---|---|---|
| 2-77 | $NHCO_2Bu$-t | SMe | — | |
| 2-78 | $NHCO_2Bu$-t | SOMe | — | |
| 2-79 | $NHCO_2Bu$-t | $SO_2Me$ | — | |
| 2-80 | $NHCO_2Bu$-t | $NMe_2$ | — | |
| 2-81 | $NHCO_2Bu$-t | $N(Me)(CO_2Bu$-t$)$ | — | |
| 2-82 | $NHCO_2Bu$-t | CN | — | |
| 2-83 | $NHCO_2Bu$-t | morphorino | — | |
| 2-84 | $NHCO_2Bu$-t | Ph | — | |
| 2-85 | $NHCO_2Bu$-t | $CO_2C_2H_5$ | — | |
| 2-86 | $NHCO_2Bu$-t | $CONHCH_3$ | — | |
| 2-87 | $NHCO_2Bu$-t | $CF_3$ | — | |
| 2-88 | $NHCO_2Bu$-t | OH | — | |
| 2-89 | $NHCO_2Bu$-t | SH | — | |
| 2-90 | $NHCO_2Bu$-t | $CH_2Cl=Cl_2$ | — | |
| 2-91 | $NHCO_2Bu$-t | etynyl | — | |
| 2-92 | $NHCO_2Bu$-t | propargyl | — | |
| 2-93 | $NHCO_2Bu$-t | (3-iodo-2-propynyl) | — | |
| 2-94 | $NHCO_2Bu$-t | Ph | — | |
| 2-95 | $NHCO_2Bu$-t | $C_6H_4OMe$-4 | — | |
| 2-96 | $NHCO_2Bu$-t | 2-pyridyl | — | |
| 2-97 | $NHCO_2Bu$-t | 4-$CF_3$-2-oxazolyl | — | |
| 2-98 | $NHCO_2Bu$-t | 3-$CF_3$-5-Cl-2-pyridyl | — | |
| 2-99 | $NHCO_2Bu$-t | pyrrolidino | — | |
| 2-100 | $NHCO_2Bu$-t | COMe | — | |
| 2-101 | $NHCO_2Bu$-t | CONHMe | — | |
| 2-102 | $NHCO_2Bu$-t | $CONMe_2$ | — | |
| 2-103 | $NHCO_2Bu$-t | COPr-c | — | |
| 2-104 | $NHCO_2Bu$-t | COPh | — | |
| 2-105 | $NHCO_2Bu$-t | $COCH_2CH=CH_2$ | — | |
| 2-106 | $NHCO_2Bu$-t | CO(propargyl) | — | |
| 2-107 | $NHCO_2Bu$-t | $CO_2Me$ | — | |
| 2-108 | $NHCO_2Bu$-t | $CO_2Ph$ | — | |
| 2-109 | $NHCO_2Bu$-t | $CO_2CH_2CH=CH_2$ | — | |
| 2-110 | $NHCO_2Bu$-t | $CO_2$(propargyl) | — | |
| 2-111 | $NHCO_2Bu$-t | Me | 2-Cl | |
| 2-112 | $NHCO_2Bu$-t | Me | 3-Cl | |
| 2-113 | $NHCO_2Bu$-t | Me | 4-Cl | |
| 2-114 | $NHCO_2Bu$-t | Me | 2,4-$Cl_2$ | |
| 2-115 | $NHCO_2Bu$-t | Me | 3,5-$Cl_2$ | |
| 2-116 | $NHCO_2Bu$-t | Me | 3,4,5-$Cl_3$ | |
| 2-117 | $NHCO_2Bu$-t | Me | 2-Me | |
| 2-118 | $NHCO_2Bu$-n | $NH_2$ | — | |
| 2-119 | $NHCO_2Bu$-n | $NHCO_2Bu$-t | — | |
| 2-120 | $NHCO_2CH_2CF_3$ | Me | — | |
| 2-121 | $NHCO_2C_2F_5$ | Me | — | |
| 2-122 | $NHCO_2CH_2CH_2F$ | Me | — | |
| 2-123 | $NHCO_2C(CH_3)_2CF_3$ | Me | — | |
| 2-124 | $NHCO_2CH_2CH_2CF_3$ | Me | — | |
| 2-125 | $NHCO_2CH_2C_2F_5$ | Me | — | |
| 2-126 | $NHCO_2CH_2CH=CH_2$ | Me | — | |
| 2-127 | $NHCO_2CH_2CH=CMe_2$ | Me | — | |
| 2-128 | $NHCO_2C(CH_3)_2CH=CH_2$ | Me | — | |
| 2-129 | $NHCO_2C(CH_3)_2CH=CHCH_3$ | Me | — | |
| 2-130 | $NHCO_2CH_2CH=CHCl$ | Me | — | |
| 2-131 | $NHCO_2CH_2CH=CHCF_3$ | Me | — | |
| 2-132 | $NHCO_2CH_2Cl=Cl_2$ | Me | — | |
| 2-133 | $NHCO_2$(1,1-dimethyl-2-propynyl) | Me | — | |

TABLE 2-continued

| No | $Z^{11}$ | $R^{11}$ | $(X)_{n1}$ | mp °C. |
|---|---|---|---|---|
| 2-134 | $NHCO_2$(2-butynyl) | Me | — | |
| 2-135 | $NHCO_2$(1,1-dimethyl-2-butynyl) | Me | — | |
| 2-136 | $NHCO_2$(1,1-dimethyl-2-pentynyl) | Me | — | |
| 2-137 | $NHCO_2$(1-propynyl) | Me | — | |
| 2-138 | $NHCO_2$(1,1-dimethyl-3-Iodo-2-pentynyl) | Me | — | |
| 2-139 | $NHCO_2$(4,4,4-trifluoro-2-butynyl) | Me | — | |
| 2-140 | $NHCO_2$Pr-c | Me | — | |
| 2-141 | $NHCO_2$Hex-c | Me | — | |
| 2-142 | $NHCO_2CH_2CH_2NHCO_2$Bu-t | Me | — | |
| 2-143 | $NHCO_2CH_2CH_2NHCO_2$Et | Me | — | |
| 2-144 | $NHCO_2CH_2CH_2CH_2NHCOCH_3$ | Me | — | |
| 2-145 | $NHCO_2CH_2CH_2CH_2NHMe_2$ | Me | — | |
| 2-146 | $NHCO_2CH_2CH(Me)COCH_3$ | Me | — | |
| 2-147 | $NHCO_2CH_2CH_2NHCOPh$ | Me | — | |
| 2-148 | $NHCO_2CH_2CH_2N(Me)COPh$ | Me | — | |
| 2-149 | $NHCO_2CH_2CH_2NHPh$ | Me | — | |
| 2-150 | $NHCO_2(CH_2)_4NH_2$ | Me | — | |
| 2-151 | $NHCO_2CH_2NHCH_2Ph$ | Me | — | |
| 2-152 | $NHCO_2CH_2N(CH_2Ph)(CO_2Bu-t)$ | Me | — | |
| 2-153 | $NHCO_2CH_2C_3H_5$-c | Me | — | |
| 2-154 | $NHCO_2CH(CH_3)C_3H_5$-c | Me | — | |
| 2-155 | $NHCO_2CH_2C_6H_{11}$-c | Me | — | |
| 2-156 | $NHCO_2CH_2Ph$ | Me | — | |
| 2-157 | $NHCO_2CH(CH_3)CH_2Ph$ | Me | — | |
| 2-158 | $NHCO_2CH(CH_3)Ph$ | Me | — | |
| 2-159 | $NHCO_2C(CH_3)_2Ph$ | Me | — | |
| 2-160 | $NHCO_2CH_2C_6H_4CF_3$-4 | Me | — | |
| 2-161 | $NHCO_2CH_2C_6H_4CN$-4 | Me | — | |
| 2-162 | $NHCO_2CH_2C_6H_4CN$-3 | Me | — | |
| 2-163 | $NHCO_2CH_2C_6H_4Cl$-4 | Me | — | |
| 2-164 | $NHCO_2CH_2C_6H_4Cl$-3 | Me | — | |
| 2-165 | $NHCO_2CH_2C_6H_4OMe$-3 | Me | — | |
| 2-166 | $NHCO_2CH_2C_6H_4OMe$-2 | Me | — | |
| 2-167 | $NHCO_2CH_2C_6H_4Me$-4 | Me | — | |
| 2-168 | $NHCO_2CH_2C_6H_4Me$-3 | Me | — | |
| 2-169 | $NHCO_2CH_2C_6H_4Me$-2 | Me | — | |
| 2-170 | $NHCO_2CH_2C_6H_4SO_2Me$-4 | Me | — | |
| 2-171 | $NHCO_2CH_2C_6H_4SO_2Me$-3 | Me | — | |
| 2-172 | $NHCO_2CH_2C_6H_4Ph$-4 | Me | — | |
| 2-173 | $NHCO_2CH_2C_6H_4Ph$-3 | Me | — | |
| 2-174 | $NHCO_2CH_2Py$-2 | Me | — | |
| 2-175 | $NHCO_2CH_2$(6-Me-2-Py) | Me | — | |
| 2-176 | $NHCO_2C(CH_3)_2Py$-4 | Me | — | |
| 2-177 | $NHCO_2CH_2$(2-thiazolyl) | Me | — | |
| 2-178 | $NHCO_2CH_2$(2-benzthiazolyl) | Me | — | |
| 2-179 | $NHCO_2CH_2CH_2OMe$ | Me | — | |
| 2-180 | $NHCO_2CH_2CH_2OEt$ | Me | — | |
| 2-181 | $NHCO_2CH_2CH_2OPr$-i | Me | — | |
| 2-182 | $NHCO_2CH_2CH_2OBu$-i | Me | — | |
| 2-183 | $NHCO_2CH_2CH_2OCH_2CH_2OMe$ | Me | — | |
| 2-184 | $NHCO_2CH_2CH_2OEt$ | i-Pr | — | |
| 2-185 | $NHCO_2CH_2CH_2OC_6H_4Cl$-4 | Me | — | |
| 2-186 | $NHCOCH_2OPh$ | Me | — | |
| 2-187 | $NHCOCH_2OC_6H_4F$-3 | Me | — | |
| 2-188 | $NHCOCH_2OC_6H_4OCF_3$-3 | Me | — | |
| 2-189 | $NHCO_2CH_2CH_2OCH_2Ph$ | Me | — | |

TABLE 2-continued

| No | $Z^{11}$ | $R^{11}$ | $(X)_{n1}$ | mp °C. |
|---|---|---|---|---|
| 2-190 | NHCO$_2$CH$_2$CH$_2$OCH$_2$CH$_2$Ph | Me | — | |
| 2-191 | NHCO$_2$(1,1-dimethyl-3-phenyl-2-pentynyl) | Me | — | |
| 2-192 | NHCO$_2$(CH$_2$)$_4$SMe | Me | — | |
| 2-193 | NHCO$_2$(CH$_2$)$_4$SCF$_3$ | Me | — | |
| 2-194 | NHCO$_2$(CH$_2$)$_4$SPh | Me | — | |
| 2-195 | NHCO$_2$(CH$_2$)$_4$SOMe | Me | — | |
| 2-196 | NHCO$_2$(CH$_2$)$_4$SOCF$_3$ | Me | — | |
| 2-197 | NHCO$_2$(CH$_2$)$_4$SOPh | Me | — | |
| 2-198 | NHCO$_2$(CH$_2$)$_4$SO$_2$Me | Me | — | |
| 2-199 | NHCO$_2$(CH$_2$)$_4$SO$_2$CF$_3$ | Me | — | |
| 2-200 | NHCO$_2$(CH$_2$)$_4$SO$_2$Ph | Me | — | |
| 2-201 | NHCO$_2$Ph | Me | — | |
| 2-202 | NHCO$_2$C$_6$H$_4$OMe-4 | Me | — | |
| 2-203 | NHCONHMe | Me | — | |
| 2-204 | NHCONHC$_2$H$_5$ | Me | — | |
| 2-205 | NHCONHPr-n | Me | — | |
| 2-206 | NHCONHBu-t | Me | — | |
| 2-207 | NHCONHBu-s | Me | — | |
| 2-208 | NHCONH(Hex-n) | Me | — | |
| 2-209 | H | Cl | — | |
| 2-210 | NH$_2$ | Cl | — | |
| 2-211 | NHCHO | Cl | — | |
| 2-212 | NHCOCH$_2$CF$_3$ | Cl | — | |
| 2-213 | NHCOC$_2$F$_5$ | Cl | — | |
| 2-214 | NHCOCH$_2$CH$_2$F | Cl | — | |
| 2-215 | NHCOC(CH$_3$)$_2$CF$_3$ | Cl | — | |
| 2-216 | NHCOCH$_2$CH$_2$CF$_3$ | Cl | — | |
| 2-217 | NHCOCH$_2$C$_2$F$_5$ | Cl | — | |
| 2-218 | NHCOCH$_2$CH=CH$_2$ | Cl | — | |
| 2-219 | NHCOCH$_2$CH=CMe$_2$ | Cl | — | |
| 2-220 | NHCOC(CH$_3$)$_2$CH=CH$_2$ | Cl | — | |
| 2-221 | NHCOC(CH$_3$)$_2$CH=CHCH$_3$ | Cl | — | |
| 2-222 | NHCOCH$_2$CH=CHCl | Cl | — | |
| 2-223 | NHCOCH$_2$CH=CHCF$_3$ | Cl | — | |
| 2-224 | NHCOCH$_2$Cl=Cl$_2$ | Cl | — | |
| 2-225 | NHCO(1,1-dimethyl-2-propynyl) | Cl | — | |
| 2-226 | NHCO(2-butynyl) | Cl | — | |
| 2-227 | NHCO(1,1-dimethyl-2-butynyl) | Cl | — | |
| 2-228 | NHCO(1,1-dimethyl-2-pentynyl) | Cl | — | |
| 2-229 | NHCO(1-propynyl) | Cl | — | |
| 2-230 | NHCO(1,1-dimethyl-3-Iodo-2-pentynyl) | Cl | — | |
| 2-231 | NHCO(4,4,4-trifluoro-2-butynyl) | Cl | — | |
| 2-232 | NHCOPr-c | Cl | — | |
| 2-233 | NHCOHex-c | Cl | — | |
| 2-234 | NHCO(CH$_2$)$_4$CO$_2$H | Cl | — | |
| 2-235 | NHCOCH$_2$CH$_2$NHCO$_2$Bu-t | Cl | — | |
| 2-236 | NHCOCH$_2$CH$_2$NHCO$_2$Et | Cl | — | |
| 2-237 | NHCOCH$_2$CH$_2$CH$_2$NHCOCH$_3$ | Cl | — | |
| 2-238 | NHCOCH$_2$CH$_2$CH$_2$NHMe$_2$ | Cl | — | |
| 2-239 | NHCOCH$_2$CH$_2$N(Me)COCH$_3$ | Cl | — | |
| 2-240 | NHCOCH$_2$CH$_2$NHCOPh | Cl | — | |
| 2-241 | NHCOCH$_2$CH$_2$N(Me)COPh | Cl | — | |
| 2-242 | NHCOCH$_2$CH$_2$NHPh | Cl | — | |
| 2-243 | NHCO(CH$_2$)$_4$NH$_2$ | Cl | — | |
| 2-244 | NHCOCH$_2$NHCH$_2$Ph | Cl | — | |
| 2-245 | NHCOCH$_2$N(CH$_2$Ph)(CO$_2$Bu-t) | Cl | — | |

TABLE 2-continued

| No | $Z^{11}$ | $R^{11}$ | $(X)_{n1}$ | mp °C. |
|---|---|---|---|---|
| 2-246 | NHCOCH$_2$CH$_2$OC$_6$H$_4$Cl-4 | Cl | — | |
| 2-247 | NHCOCH$_2$OPh | Cl | — | |
| 2-248 | NHCOCH$_2$OC$_6$H$_4$F-3 | Cl | — | |
| 2-249 | NHCOCH$_2$OC$_6$H$_4$OCF$_3$-3 | Cl | — | |
| 2-250 | NHCO(CH$_2$)$_4$SMe | Cl | — | |
| 2-251 | NHCOCH$_2$CH$_2$OEt | Cl | — | |
| 2-252 | NHCOCH$_2$CH$_2$OPr-i | Cl | — | |
| 2-253 | NHCOCH$_2$CH$_2$OBu-i | Cl | — | |
| 2-254 | NHCOCH$_2$CH$_2$OCH$_2$CH$_2$OMe | Cl | — | |
| 2-255 | NHCO$_2$CH$_3$ | Cl | — | |
| 2-256 | NHCO$_2$C$_2$H$_5$ | Cl | — | |
| 2-257 | NHCO$_2$Pr-n | Cl | — | |
| 2-258 | NHCO$_2$Pr-i | Cl | — | |
| 2-259 | NHCO$_2$Bu-n | Cl | — | |
| 2-260 | NHCO$_2$Bu-i | Cl | — | |
| 2-261 | NHCO$_2$Bu-s | Cl | — | |
| 2-262 | NHCO$_2$Bu-t | Cl | — | |
| 2-263 | NHCO$_2$Bu-t | Br | — | 91-93 |
| 2-264 | NHCO$_2$Bu-t | Cl | 2-Cl | |
| 2-265 | NHCO$_2$Bu-t | Cl | 3-Cl | |
| 2-266 | NHCO$_2$Bu-t | Cl | 4-Cl | |
| 2-267 | NHCO$_2$Bu-t | Cl | 2,4-Cl$_2$ | |
| 2-268 | NHCO$_2$Bu-t | Cl | 3,5-Cl$_2$ | |
| 2-269 | NHCO$_2$Bu-t | Cl | 3,4,5-Cl$_3$ | |
| 2-270 | NHCO$_2$Bu-t | Cl | 2-Me | |
| 2-271 | NHCO$_2$CH$_2$CF$_3$ | Cl | — | |
| 2-272 | NHCO$_2$C$_2$F$_5$ | Cl | — | |
| 2-273 | NHCO$_2$CH$_2$CH$_2$F | Cl | — | |
| 2-274 | NHCO$_2$C(CH$_3$)$_2$CF$_3$ | Cl | — | |
| 2-275 | NHCO$_2$CH$_2$CH$_2$CF$_3$ | Cl | — | |
| 2-276 | NHCO$_2$CH$_2$C$_2$F$_5$ | Cl | — | |
| 2-277 | NHCO$_2$CH$_2$CH=CH$_2$ | Cl | — | |
| 2-278 | NHCO$_2$CH$_2$CH=CMe$_2$ | Cl | — | |
| 2-279 | NHCO$_2$C(CH$_3$)$_2$CH=CH$_2$ | Cl | — | |
| 2-280 | NHCO$_2$C(CH$_3$)$_2$CH=CHCH$_3$ | Cl | — | |
| 2-281 | NHCO$_2$CH$_2$CH=CHCl | Cl | — | |
| 2-282 | NHCO$_2$CH$_2$CH=CHCF$_3$ | Cl | — | |
| 2-283 | NHCO$_2$CH$_2$CI=CI$_2$ | Cl | — | |
| 2-284 | NHCO$_2$(1,1-dimethyl-2-propynyl) | Cl | — | |
| 2-285 | NHCO$_2$(2-butynyl) | Cl | — | |
| 2-286 | NHCO$_2$(1,1-dimethyl-2-butynyl) | Cl | — | |
| 2-287 | NHCO$_2$(1,1-dimethyl-2-pentynyl) | Cl | — | |
| 2-288 | NHCO$_2$(1-propynyl) | Cl | — | |
| 2-289 | NHCO$_2$(1,1-dimethyl-3-Iodo-2-pentynyl) | Cl | — | |
| 2-290 | NHCO$_2$(4,4,4-trifluoro-2-butynyl) | Cl | — | |
| 2-291 | NHCO$_2$Pr-c | Cl | — | |
| 2-292 | NHCO$_2$Hex-c | Cl | — | |
| 2-293 | NHCO$_2$CH$_2$CH$_2$NHCO$_2$Bu-t | Cl | — | |
| 2-294 | NHCO$_2$CH$_2$CH$_2$NHCO$_2$Et | Cl | — | |
| 2-295 | NHCO$_2$CH$_2$CH$_2$CH$_2$NHCOCH$_3$ | Cl | — | |
| 2-296 | NHCO$_2$CH$_2$CH$_2$CH$_2$NMe$_2$ | Cl | — | |
| 2-297 | NHCO$_2$CH$_2$CH$_2$N(Me)COCH$_3$ | Cl | — | |
| 2-298 | NHCO$_2$CH$_2$CH$_2$NHCOPh | Cl | — | |
| 2-299 | NHCO$_2$CH$_2$CH$_2$N(Me)COPh | Cl | — | |
| 2-300 | NHCO$_2$CH$_2$CH$_2$NHPh | Cl | — | |
| 2-301 | NHCO$_2$(CH$_2$)$_4$NH$_2$ | Cl | — | |
| 2-302 | NHCO$_2$CH$_2$NHCH$_2$Ph | Cl | — | |

TABLE 2-continued

| No | $Z^{11}$ | $R^{11}$ | $(X)_{n1}$ | mp °C. |
|---|---|---|---|---|
| 2-303 | NHCO$_2$CH$_2$N(CH$_2$Ph)(CO$_2$Bu-t) | Cl | — | |
| 2-304 | NHCO$_2$CH$_2$C$_3$H$_5$-c | Cl | — | |
| 2-305 | NHCO$_2$CH(CH$_3$)C$_3$H$_5$-c | Cl | — | |
| 2-306 | NHCO$_2$CH$_2$C$_6$H$_{11}$-c | Cl | — | |
| 2-307 | NHCO$_2$CH$_2$Ph | Cl | — | |
| 2-308 | NHCO$_2$CH(CH$_3$)CH$_2$Ph | Cl | — | |
| 2-309 | NHCO$_2$CH(CH$_3$)Ph | Cl | — | |
| 2-310 | NHCO$_2$C(CH$_3$)$_2$Ph | Cl | — | |
| 2-311 | NHCO$_2$CH$_2$C$_6$H$_4$CF$_3$-4 | Cl | — | |
| 2-312 | NHCO$_2$CH$_2$C$_6$H$_4$CN-4 | Cl | — | |
| 2-313 | NHCO$_2$CH$_2$C$_6$H$_4$CN-3 | Cl | — | |
| 2-314 | NHCO$_2$CH$_2$C$_6$H$_4$Cl-4 | Cl | — | |
| 2-315 | NHCO$_2$CH$_2$C$_6$H$_4$Cl-3 | Cl | — | |
| 2-316 | NHCO$_2$CH$_2$C$_6$H$_4$OMe-3 | Cl | — | |
| 2-317 | NHCO$_2$CH$_2$C$_6$H$_4$OMe-2 | Cl | — | |
| 2-318 | NHCO$_2$CH$_2$C$_6$H$_4$Me-4 | Cl | — | |
| 2-319 | NHCO$_2$CH$_2$C$_6$H$_4$Me-3 | Cl | — | |
| 2-320 | NHCO$_2$CH$_2$C$_6$H$_4$Me-2 | Cl | — | |
| 2-321 | NHCO$_2$CH$_2$C$_6$H$_4$SO$_2$Me-4 | Cl | — | |
| 2-322 | NHCO$_2$CH$_2$C$_6$H$_4$SO$_2$Me-3 | Cl | — | |
| 2-323 | NHCO$_2$CH$_2$C$_6$H$_4$Ph-4 | Cl | — | |
| 2-324 | NHCO$_2$CH$_2$C$_6$H$_4$Ph-3 | Cl | — | |
| 2-325 | NHCO$_2$CH$_2$Py-2 | Cl | — | |
| 2-326 | NHCO$_2$CH$_2$(6-Me-2-Py) | Cl | — | |
| 2-327 | NHCO$_2$C(CH$_3$)$_2$Py-4 | Cl | — | |
| 2-328 | NHCO$_2$CH$_2$(2-thiazolyl) | Cl | — | |
| 2-329 | NHCO$_2$CH$_2$(2-benzthiazolyl) | Cl | — | |
| 2-330 | NHCO$_2$CH$_2$CH$_2$OMe | Cl | — | |
| 2-331 | NHCO$_2$CH$_2$CH$_2$OEt | Cl | — | |
| 2-332 | NHCO$_2$CH$_2$CH$_2$OPr-i | Cl | — | |
| 2-333 | NHCO$_2$CH$_2$CH$_2$OBu-i | Cl | — | |
| 2-334 | NHCO$_2$CH$_2$CH$_2$OCH$_2$OMe | Cl | — | |
| 2-335 | NHCO$_2$CH$_2$CH$_2$OC$_6$H$_4$Cl-4 | Cl | — | |
| 2-336 | NHCOCH$_2$OPh | Cl | — | |
| 2-337 | NHCOCH$_2$OC$_6$H$_4$F-3 | Cl | — | |
| 2-338 | NHCOCH$_2$OC$_6$H$_4$OCF$_3$-3 | Cl | — | |
| 2-339 | NHCO$_2$CH$_2$CH$_2$OCH$_2$Ph | Cl | — | |
| 2-340 | NHCO$_2$(1,1-dimethyl-3-phenyl-2-pentynyl) | Cl | — | |
| 2-341 | NHCO$_2$CH$_2$CH$_2$OCH$_2$CH$_2$Ph | Cl | — | |
| 2-342 | NHCO$_2$(1,1-dimethyl-3-phenyl-2-pentynyl) | Cl | — | |
| 2-343 | NHCO$_2$(CH$_2$)$_4$SMe | Cl | — | |
| 2-344 | NHCO$_2$(CH$_2$)$_4$SCF$_3$ | Cl | — | |
| 2-345 | NHCO$_2$(CH$_2$)$_4$SPh | Cl | — | |
| 2-346 | NHCO$_2$(CH$_2$)$_4$SOMe | Cl | — | |
| 2-347 | NHCO$_2$(CH$_2$)$_4$SOCF$_3$ | Cl | — | |
| 2-348 | NHCO$_2$(CH$_2$)$_4$SOPh | Cl | — | |
| 2-349 | NHCO$_2$(CH$_2$)$_4$SO$_2$Me | Cl | — | |
| 2-350 | NHCO$_2$(CH$_2$)$_4$SO$_2$CF$_3$ | Cl | — | |
| 2-351 | NHCO$_2$(CH$_2$)$_4$SO$_2$Ph | Cl | — | |
| 2-352 | NHCO$_2$Ph | Cl | — | |
| 2-353 | NHCO$_2$C$_6$H$_4$OMe-4 | Cl | — | |
| 2-354 | NHCONHMe | Cl | — | |
| 2-355 | NHCONHC$_2$H$_5$ | Cl | — | |
| 2-356 | NHCONHPr-n | Cl | — | |
| 2-357 | NHCONHBu-t | Cl | — | |
| 2-358 | NHCONHBu-s | Cl | — | |
| 2-359 | NHCONH(Hex-n) | Cl | — | |
| 2-360 | NHCOCH$_2$CF$_3$ | — | — | |
| 2-361 | NHCOC$_2$F$_5$ | — | — | |
| 2-362 | NHCOCH$_2$CH$_2$F | — | — | |

TABLE 2-continued

| No | $Z^{11}$ | $R^{11}$ | $(X)_{n1}$ | mp °C. |
|---|---|---|---|---|
| 2-363 | NHCOC(CH$_3$)$_2$CF$_3$ | — | — | |
| 2-364 | NHCOCH$_2$CH$_2$CF$_3$ | — | — | |
| 2-365 | NHCOCH$_2$C$_2$F$_5$ | — | — | |
| 2-366 | NHCOCH$_2$CH=CH$_2$ | — | — | |
| 2-367 | NHCOCH$_2$CH=CMe$_2$ | — | — | |
| 2-368 | NHCOC(CH$_3$)$_2$CH=CH$_2$ | — | — | |
| 2-369 | NHCOC(CH$_3$)$_2$CH=CHCH$_3$ | — | — | |
| 2-370 | NHCOCH$_2$CH=CHCl | — | — | |
| 2-371 | NHCOCH$_2$CH=CHCF$_3$ | — | — | |
| 2-372 | NHCOCH$_2$Cl=Cl$_2$ | — | — | |
| 2-373 | NHCO(1,1-dimethyl-2-propynyl) | — | — | |
| 2-374 | NHCO(2-butynyl) | — | — | |
| 2-375 | NHCO(1,1-dimethyl-2-butynyl) | — | — | |
| 2-376 | NHCO(1,1-dimethyl-2-pentynyl) | — | — | |
| 2-377 | NHCO(1-propynyl) | — | — | |
| 2-378 | NHCO(1,1-dimethyl-3-Iodo-2-pentynyl) | — | — | |
| 2-379 | NHCO(4,4,4-trifluoro-2-butynyl) | — | — | |
| 2-380 | NHCO(CH$_2$)$_4$CO$_2$H | — | — | |
| 2-381 | NHCOCH$_2$CH$_2$CH$_2$NHMe$_2$ | — | — | |
| 2-382 | NHCO(CH$_2$)$_4$NH$_2$ | — | — | |
| 2-383 | NHCOCH$_2$NHCH$_2$Ph | — | — | |
| 2-384 | NHCOCH$_2$N(CH$_2$Ph)(CO$_2$Bu-t) | — | — | |
| 2-385 | NHCOCH$_2$CH$_2$NMe$_2$ | — | — | |
| 2-386 | NHCOCH$_2$CH$_2$NHEt | — | — | |
| 2-387 | NHCOCH$_2$CH$_2$NHPr-n | — | — | |
| 2-388 | NHCOCH$_2$CH$_2$OC$_6$H$_4$Cl-4 | — | — | |
| 2-389 | NHCOCH$_2$OPh | — | — | 95-97 |
| 2-390 | NHCOCH$_2$OC$_6$H$_4$F-3 | — | — | |
| 2-391 | NHCOCH$_2$OC$_6$H$_4$OCF$_3$-3 | — | — | 112-113 |
| 2-392 | NHCOCH2OC$_6$H$_4$CN-2 | — | — | 159-162 |
| 2-393 | NHCOCH2OC$_6$H$_4$F-4 | — | — | |
| 2-394 | NHCOCH$_2$OC$_6$H$_3$(3,4-methylenedioxy) | — | — | 67-72 |
| 2-395 | NHCOCH$_2$OC$_6$H$_4$(CONH$_2$)-2 | — | — | |
| 2-396 | NHCOCH$_2$OC$_6$H$_3$(3,4-(OCH$_3$)$_2$) | — | — | 140-141 |
| 2-397 | NHCOCH$_2$O(6-CF$_3$-pyrimidin-4-yl) | — | — | 108-111 (dec.) |
| 2-398 | NHCOCH$_2$O(3-Py) | — | — | |
| 2-399 | NHCOCH$_2$CH$_2$CH$_2$COCH$_3$ | — | — | |
| 2-400 | NHCO$_2$CH$_2$CF$_3$ | — | — | |
| 2-401 | NHCO$_2$C$_2$F$_5$ | — | — | |
| 2-402 | NHCO$_2$CH$_2$CH$_2$F | — | — | |
| 2-403 | NHCO$_2$C(CH$_3$)$_2$CF$_3$ | — | — | |
| 2-404 | NHCO$_2$CH$_2$CH$_2$CF$_3$ | — | — | |
| 2-405 | NHCO$_2$CH$_2$C$_2$F$_5$ | — | — | |
| 2-406 | NHCO$_2$CH$_2$CH=CH$_2$ | — | — | |
| 2-407 | NHCO$_2$CH$_2$CH=CMe$_2$ | — | — | |
| 2-408 | NHCO$_2$C(CH$_3$)$_2$CH=CH$_2$ | — | — | |
| 2-409 | NHCO$_2$C(CH$_3$)$_2$CH=CHCH$_3$ | — | — | |
| 2-410 | NHCO$_2$CH$_2$CH=CHCl | — | — | |
| 2-411 | NHCO$_2$CH$_2$CH=CHCF$_3$ | — | — | |
| 2-412 | NHCO$_2$CH$_2$Cl=Cl$_2$ | — | — | |
| 2-413 | NHCO$_2$(1,1-dimethyl-2-propynyl) | — | — | |
| 2-414 | NHCO$_2$(2-butynyl) | — | — | |
| 2-415 | NHCO$_2$(1,1-dimethyl-2-butynyl) | — | — | |

TABLE 2-continued

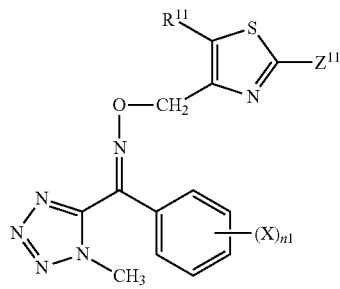

| No | $Z^{11}$ | $R^{11}$ | $(X)_{n1}$ | mp °C. |
|---|---|---|---|---|
| 2-416 | $NHCO_2$(1,1-dimethyl-2-pentynyl) | — | — | |
| 2-417 | $NHCO_2$(1-propynyl) | — | — | |
| 2-418 | $NHCO_2$(1,1-dimethyl-3-Iodo-2-pentynyl) | — | — | |
| 2-419 | $NHCO_2$(4,4,4-trifluoro-2-butynyl) | — | — | |
| 2-420 | $NHCO_2$(1,1-dimethyl-3-phenyl-2-pentynyl) | — | — | |
| 2-421 | $NHCO_2CH_2CH_2NHCO_2Bu$-t | — | — | |
| 2-422 | $NHCO_2CH_2CH_2NHCO_2Et$ | — | — | |
| 2-423 | $NHCO_2CH_2N(CH_2Ph)(CO_2Bu$-t) | — | — | |
| 2-424 | $NHCO_2CH_2NCH_2Ph$ | — | — | |
| 2-425 | $NHCO_2CH_2CH_2NCH_2Ph$ | — | — | |
| 2-426 | $NHCO_2CH_2CH_2NCH_2C_6H_4Cl$-4 | — | — | |
| 2-427 | $NHCO_2CH_2CH_2NHMe$ | — | — | |
| 2-428 | $NHCO_2CH_2C(CH_3)_2N(CH_3)_2$ | — | — | |
| 2-429 | $NHCO_2CH(CH_3)CH_2N(CH_3)_2$ | — | — | |
| 2-430 | $NHCO_2CH_2C_3H_5$-c | — | — | |
| 2-431 | $NHCO_2CH(CH_3)C_3H_5$-c | — | — | |
| 2-432 | $NHCO_2CH_2C_6H_{11}$-c | — | — | |
| 2-433 | $NHCO_2CH(CH_3)CH_2Ph$ | — | — | |
| 2-434 | $NHCO_2CH(CH_3)Ph$ | — | — | |
| 2-435 | $NHCO_2C(CH_3)_2Ph$ | — | — | |
| 2-436 | $NHCO_2CH_2C_6H_4CF_3$-4 | — | — | |
| 2-437 | $NHCO_2CH_2C_6H_4CN$-4 | — | — | |
| 2-438 | $NHCO_2CH_2C_6H_4CN$-3 | — | — | |
| 2-439 | $NHCO_2CH_2C_6H_4Cl$-4 | — | — | |
| 2-440 | $NHCO_2CH_2C_6H_4Cl$-3 | — | — | |
| 2-441 | $NHCO_2CH_2C_6H_4OMe$-3 | — | — | |
| 2-442 | $NHCO_2CH_2C_6H_4OMe$-2 | — | — | |
| 2-443 | $NHCO_2CH_2C_6H_4Me$-4 | — | — | |
| 2-444 | $NHCO_2CH_2C_6H_4Me$-3 | — | — | |
| 2-445 | $NHCO_2CH_2C_6H_4Me$-2 | — | — | |
| 2-446 | $NHCO_2CH_2C_6H_4SO_2Me$-4 | — | — | |
| 2-447 | $NHCO_2CH_2C_6H_4SO_2Me$-3 | — | — | |
| 2-448 | $NHCO_2CH_2C_6H_4Ph$-4 | — | — | |
| 2-449 | $NHCO_2CH_2C_6H_4Ph$-3 | — | — | |
| 2-450 | $NHCO_2CH_2C_6H_4OCH_3$-4 | — | — | |
| 2-451 | $NHCO_2CH_2C_6H_3$(3,4-methylenedioxy) | — | — | |
| 2-452 | $NHCO_2CH_2Py$-2 | — | — | |
| 2-453 | $NHCO_2CH_2$(6-Me-2-Py) | — | — | |
| 2-454 | $NHCO_2C(CH_3)_2Py$-4 | — | — | |
| 2-455 | $NHCO_2CH_2$(2-thiazolyl) | — | — | |
| 2-456 | $NHCO_2CH_2$(2-benzthiazolyl) | — | — | |
| 2-457 | $NHCO_2CH_2$(3-Py) | — | — | |
| 2-458 | $NHCO_2CH_2$(4-Py) | — | — | |
| 2-459 | $NHCO_2CH(CH_3)$(4-Py) | — | — | |
| 2-460 | $NHCO_2CH_2CH_2OMe$ | — | — | |
| 2-461 | $NHCO_2CH_2CH_2OEt$ | — | — | |
| 2-462 | $NHCO_2CH_2CH_2OPr$-i | — | — | |
| 2-463 | $NHCO_2CH_2CH_2OBu$-i | — | — | |
| 2-464 | $NHCO_2CH_2CH_2OCH_2OMe$ | — | — | |
| 2-465 | $NHCO_2C(CH_3)_2CH_2OCH_3$ | — | — | |
| 2-466 | $NHCO_2CH(CH_3)CH_2OCH_3$ | — | — | |
| 2-467 | $NHCO_2CH_2CH_2OC_6H_4Cl$-4 | — | — | |
| 2-468 | $NHCO_2CH_2OPh$ | — | — | |
| 2-469 | $NHCO_2CH_2OC_6H_4F$-3 | — | — | |
| 2-470 | $NHCO_2CH_2OC_6H_4OCF_3$-3 | — | — | |
| 2-471 | $NHCO_2CH_2CH_2OCH_2Ph$ | — | — | |
| 2-472 | $NHCO_2CH_2CH_2OCH_2CH_2Ph$ | — | — | |

TABLE 2-continued

| No | Z¹¹ | R¹¹ | (X)ₙ₁ | mp °C. |
|---|---|---|---|---|
| 2-473 | NHCO₂(CH₂)₄SMe | — | — | |
| 2-474 | NHCO₂(CH₂)₄SCF₃ | — | — | |
| 2-475 | NHCO₂(CH₂)₄SPh | — | — | |
| 2-476 | NHCO₂(CH₂)₄SOMe | — | — | |
| 2-477 | NHCO₂(CH₂)₄SOCF₃ | — | — | |
| 2-478 | NHCO₂(CH₂)₄SOPh | — | — | |
| 2-479 | NHCO₂(CH₂)₄SO₂Me | — | — | |
| 2-480 | NHCO₂(CH₂)₄SO₂CF₃ | — | — | |
| 2-481 | NHCO₂(CH₂)₄SO₂Ph | — | — | |
| 2-482 | NHCO₂Ph | — | — | |
| 2-483 | NHCO₂C₆H₄OMe-4 | — | — | |

TABLE 3

| No | Z | Rₙ₂ | (X)ₙ₁ | mp °C. |
|---|---|---|---|---|
| 3-1 | H | 4-Me | — | |
| 3-2 | NH₂ | 4-Me | — | |
| 3-3 | NH₂ | 4-Bu-t | — | |
| 3-4 | NH₂ | 4-OC₂H₅ | — | |
| 3-5 | NH₂ | 5-CH₃ | — | |
| 3-6 | NH₂ | 4-OCH₃ | — | |
| 3-7 | NH₂ | 4-C₂H₅ | — | |
| 3-8 | NHCHO | 4-Me | — | |
| 3-9 | NHCOCH₃ | 4-Me | — | |
| 3-10 | NHCOC₂H₅ | 4-Me | — | |
| 3-11 | NHCOPr-n | 4-Me | — | |
| 3-12 | NHCOPr-i | 4-Me | — | |
| 3-13 | NHCOBu-n | 4-Me | — | |
| 3-14 | NHCOBu-i | 4-Me | — | |
| 3-15 | NHCOBu-s | 4-Me | — | |
| 3-16 | NHCOBu-t | 4-Me | — | |
| 3-17 | NHCOBu-t | 4-OMe | — | |
| 3-18 | NHCOCH₂CF₃ | 4-Me | — | |
| 3-19 | NHCOC₂F₅ | 4-Me | — | |
| 3-20 | NHCOCH₂CH₂F | 4-Me | — | |
| 3-21 | NHCOC(CH₃)₂CF₃ | 4-Me | — | |
| 3-22 | NHCOCH₂CH₂CF₃ | 4-Me | — | |
| 3-23 | NHCOCH₂C₂F₅ | 4-Me | — | |
| 3-24 | NHCOCH₂CH=CH₂ | 4-Me | — | |
| 3-25 | NHCOCH₂CH=CMe₂ | 4-Me | — | |
| 3-26 | NHCOC(CH₃)₂CH=CH₂ | 4-Me | — | |
| 3-27 | NHCOC(CH₃)₂CH=CHCH₃ | 4-Me | — | |
| 3-28 | NHCOCH₂CH=CHCl | 4-Me | — | |

TABLE 3-continued

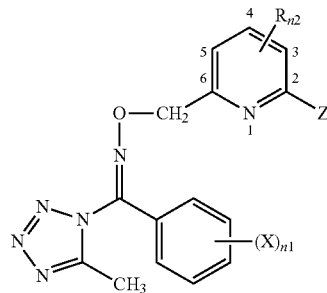

| No | Z | $R_{n2}$ | $(X)_{n1}$ | mp °C. |
|---|---|---|---|---|
| 3-29 | NHCOCH$_2$CH=CHCF$_3$ | 4-Me | — | |
| 3-30 | NHCOCH$_2$Cl=Cl$_2$ | 4-Me | — | |
| 3-31 | NHCO(1,1-dimethyl-2-propynyl) | 4-Me | — | |
| 3-32 | NHCO(2-butynyl) | 4-Me | — | |
| 3-33 | NHCO(1,1-dimethyl-2-butynyl) | 4-Me | — | |
| 3-34 | NHCO(1,1-dimethyl-2-pentynyl) | 4-Me | — | |
| 3-35 | NHCO(1-propynyl) | 4-Me | — | |
| 3-36 | NHCO(1,1-dimethyl-3-Iodo-2-pentynyl) | 4-Me | — | |
| 3-37 | NHCO(4,4,4-trifluoro-2-butynyl) | 4-Me | — | |
| 3-38 | NHCOPr-c | 4-Me | — | |
| 3-39 | NHCOHex-c | 4-Me | — | |
| 3-40 | NHCO(CH$_2$)$_4$CO$_2$H | 4-Me | — | |
| 3-41 | NHCOCH$_2$CH$_2$NHCO$_2$Bu-t | 4-Me | — | |
| 3-42 | NHCOCH$_2$CH$_2$NHCO$_2$Et | 4-Me | — | |
| 3-43 | NHCOCH$_2$CH$_2$CH$_2$NHCOCH$_3$ | 4-Me | — | |
| 3-44 | NHCOCH$_2$CH$_2$CH$_2$NHMe$_2$ | 4-Me | — | |
| 3-45 | NHCOCH$_2$CH$_2$N(Me)COCH$_3$ | 4-Me | — | |
| 3-46 | NHCOCH$_2$CH$_2$NHCOPh | 4-Me | — | |
| 3-47 | NHCOCH$_2$CH$_2$N(Me)COPh | 4-Me | — | |
| 3-48 | NHCOCH$_2$CH$_2$NHPh | 4-Me | — | |
| 3-49 | NHCO(CH$_2$)$_4$NH$_2$ | 4-Me | — | |
| 3-50 | NHCOCH$_2$NHCH$_2$Ph | 4-Me | — | |
| 3-51 | NHCOCH$_2$N(CH$_2$Ph)(CO$_2$Bu-t) | 4-Me | — | |
| 3-52 | NHCOCH$_2$CH$_2$OC$_6$H$_4$Cl-4 | 4-Me | — | |
| 3-53 | NHCOCH$_2$OPh | 4-Me | — | |
| 3-54 | NHCOCH$_2$OC$_6$H$_4$F-3 | 4-Me | — | |
| 3-55 | NHCOCH$_2$OC$_6$H$_4$OCF$_3$-3 | 4-Me | — | |
| 3-56 | NHCO(CH$_2$)$_4$SMe | 4-Me | — | |
| 3-57 | NHCOCH$_2$CH$_2$OEt | 4-Me | — | |
| 3-58 | NHCOCH$_2$CH$_2$OPr-i | 4-Me | — | |
| 3-59 | NHCOCH$_2$CH$_2$OBu-i | 4-Me | — | |
| 3-60 | NHCOCH$_2$CH$_2$OCH$_2$OMe | 4-Me | — | |
| 3-61 | NHCO$_2$CH$_3$ | 4-Me | — | |
| 3-62 | NHCO$_2$C$_2$H$_5$ | 4-Me | — | |
| 3-63 | NHCO$_2$Pr-n | 4-Me | — | |
| 3-64 | NHCO$_2$Pr-i | 4-Me | — | |
| 3-65 | NHCO$_2$Bu-n | 4-Me | — | |
| 3-66 | NHCO$_2$Bu-i | 4-Me | — | |
| 3-67 | NHCO$_2$Bu-s | 4-Me | — | |
| 3-68 | NHCO$_2$Bu-t | 4-i-Pr | — | |
| 3-69 | NHCO$_2$Bu-t | 5-Me | — | |
| 3-70 | NHCO$_2$Bu-t | 4-t-Bu | — | |
| 3-71 | NHCO$_2$Bu-t | 4-Me | — | |
| 3-72 | NHCO$_2$Bu-t | 4-Et | — | |
| 3-73 | NHCO$_2$Bu-t | 4-CH=CH2 | — | |
| 3-74 | NHCO$_2$Bu-t | 4-OMe | — | |
| 3-75 | NHCO$_2$Bu-t | 4-OEt | — | |
| 3-76 | NHCO$_2$Bu-t | 4-OCH$_2$CH$_2$OEt | — | |
| 3-77 | NHCO$_2$Bu-t | 4-OPr-i | — | |
| 3-78 | NHCO$_2$Bu-t | 4-OBu-n | — | |
| 3-79 | NHCO$_2$Bu-t | 4-SMe | — | |
| 3-80 | NHCO$_2$Bu-t | 4-SOMe | — | |
| 3-81 | NHCO$_2$Bu-t | 4-SO$_2$Me | — | |
| 3-82 | NHCO$_2$Bu-t | 4-NMe$_2$ | — | |
| 3-83 | NHCO$_2$Bu-t | 4-N(Me)(CO$_2$Bu-t) | — | |
| 3-84 | NHCO$_2$Bu-t | 5-CN | — | |
| 3-85 | NHCO$_2$Bu-t | 4-CN | — | |

TABLE 3-continued

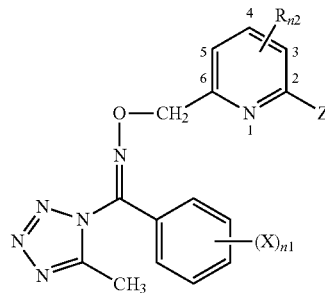

| No | Z | $R_{n2}$ | $(X)_{n1}$ | mp °C. |
|---|---|---|---|---|
| 3-86 | NHCO$_2$Bu-t | 4-morphorino | — | |
| 3-87 | NHCO$_2$Bu-t | 5-Ph | — | |
| 3-88 | NHCO$_2$Bu-t | 5-CO$_2$C$_2$H$_5$ | — | |
| 3-89 | NHCO$_2$Bu-t | 5-CONHCH$_3$ | — | |
| 3-90 | NHCO$_2$Bu-t | CF$_3$ | — | |
| 3-91 | NHCO$_2$Bu-t | 5-OH | — | |
| 3-92 | NHCO$_2$Bu-t | 5-SH | — | |
| 3-93 | NHCO$_2$Bu-t | 4-CH$_2$Cl=Cl$_2$ | — | |
| 3-94 | NHCO$_2$Bu-t | 4-etynyl | — | |
| 3-95 | NHCO$_2$Bu-t | 4-propargyl | — | |
| 3-96 | NHCO$_2$Bu-t | 4-(3-iodo-2-propynyl) | — | |
| 3-97 | NHCO$_2$Bu-t | 4-Ph | — | |
| 3-98 | NHCO$_2$Bu-t | 4-C$_6$H$_4$OMe-4 | — | |
| 3-99 | NHCO$_2$Bu-t | 4-(2-pyridyl) | — | |
| 3-100 | NHCO$_2$Bu-t | 4-(4-CF$_3$-2-oxazolyl) | — | |
| 3-101 | NHCO$_2$Bu-t | 4-(3-CF$_3$-5-Cl-2-pyridyl) | — | |
| 3-102 | NHCO$_2$Bu-t | 4-pyrrolidino | — | |
| 3-103 | NHCO$_2$Bu-t | 4-COMe | — | |
| 3-104 | NHCO$_2$Bu-t | 4-CONHMe | — | |
| 3-105 | NHCO$_2$Bu-t | 4-CONMe$_2$ | — | |
| 3-106 | NHCO$_2$Bu-t | 4-COPr-c | — | |
| 3-107 | NHCO$_2$Bu-t | 4-COPh | — | |
| 3-108 | NHCO$_2$Bu-t | 4-COCH$_2$CH=CH$_2$ | — | |
| 3-109 | NHCO$_2$Bu-t | 4-CO(propargyl) | — | |
| 3-110 | NHCO$_2$Bu-t | 4-CO$_2$Me | — | |
| 3-111 | NHCO$_2$Bu-t | 4-CO$_2$Ph | — | |
| 3-112 | NHCO$_2$Bu-t | 4-CO$_2$CH$_2$CH=CH$_2$ | — | |
| 3-113 | NHCO$_2$Bu-t | 4-CO$_2$(propargyl) | — | |
| 3-114 | NHCO$_2$Bu-t | 4-Me | 2-Cl | |
| 3-115 | NHCO$_2$Bu-t | 4-Me | 3-Cl | |
| 3-116 | NHCO$_2$Bu-t | 4-Me | 4-Cl | |
| 3-117 | NHCO$_2$Bu-t | 4-Me | 2,4-Cl$_2$ | |
| 3-118 | NHCO$_2$Bu-t | 4-Me | 3,5-Cl$_2$ | |
| 3-119 | NHCO$_2$Bu-t | 4-Me | 3,4,5-Cl$_3$ | |
| 3-120 | NHCO$_2$Bu-t | 4-Me | 2-Me | |
| 3-121 | NHCO$_2$Bu-t | 3,4-diMe | — | |
| 3-122 | NHCO$_2$Bu-t | 3,5-diMe | — | |
| 3-123 | NHCO$_2$Bu-t | 4,5-diMe | — | |
| 3-124 | NHCO$_2$Bu-t | 3,4,5-triMe | — | |
| 3-125 | NHCO$_2$Bu-t | 3-Cl-4-Me | — | |
| 3-126 | NHCO$_2$Bu-t | 5-Cl-4-Me | — | |
| 3-127 | NHCO$_2$Bu-t | 3,5-diCl-4-Me | — | |
| 3-128 | NHCO$_2$Bu-t | 3,5-diCl | — | |
| 3-129 | NHCO$_2$Bu-t | 3,4-diCl | — | |
| 3-130 | NHCO$_2$Bu-t | 3,4-diF | — | |
| 3-131 | NHCO$_2$Bu-n | 4-NH$_2$ | — | |
| 3-132 | NHCO$_2$Bu-n | 4-NHCO$_2$Bu-t | — | |
| 3-133 | NHCO$_2$CH$_2$CF$_3$ | 4-Me | — | |
| 3-134 | NHCO$_2$C$_2$F$_5$ | 4-Me | — | |
| 3-135 | NHCO$_2$CH$_2$CH$_2$F | 4-Me | — | |
| 3-136 | NHCO$_2$C(CH$_3$)$_2$CF$_3$ | 4-Me | — | |
| 3-137 | NHCO$_2$CH$_2$CH$_2$CF$_3$ | 4-Me | — | |
| 3-138 | NHCO$_2$CH$_2$C$_2$F$_5$ | 4-Me | — | |
| 3-139 | NHCO$_2$CH$_2$CH=CH$_2$ | 4-Me | — | |
| 3-140 | NHCO$_2$CH$_2$CH=CMe$_2$ | 4-Me | — | |
| 3-141 | NHCO$_2$C(CH$_3$)$_2$CH=CH$_2$ | 4-Me | — | |
| 3-142 | NHCO$_2$C(CH$_3$)$_2$CH=CHCH$_3$ | 4-Me | — | |
| 3-143 | NHCO$_2$CH$_2$CH=CHCl | 4-Me | — | |

TABLE 3-continued

[Structure: pyridine with substituents at positions 2 (Z), 4 ($R_{n2}$), and 6 connected via O-CH2-N=C to a tetrazole (with CH3) and phenyl ring with $(X)_{n1}$]

| No | Z | $R_{n2}$ | $(X)_{n1}$ | mp °C. |
|---|---|---|---|---|
| 3-144 | NHCO$_2$CH$_2$CH=CHCF$_3$ | 4-Me | — | |
| 3-145 | NHCO$_2$CH$_2$Cl=Cl$_2$ | 4-Me | — | |
| 3-146 | NHCO$_2$(1,1-dimethyl-2-propynyl) | 4-Me | — | |
| 3-147 | NHCO$_2$(2-butynyl) | 4-Me | — | |
| 3-148 | NHCO$_2$(1,1-dimethyl-2-butynyl) | 4-Me | — | |
| 3-149 | NHCO$_2$(1,1-dimethyl-2-pentynyl) | 4-Me | — | |
| 3-150 | NHCO$_2$(1-propynyl) | 4-Me | — | |
| 3-151 | NHCO$_2$(1,1-dimethyl-3-Iodo-2-pentynyl) | 4-Me | — | |
| 3-152 | NHCO$_2$(4,4,4-trifluoro-2-butynyl) | 4-Me | — | |
| 3-153 | NHCO$_2$Pr-c | 4-Me | — | |
| 3-154 | NHCO$_2$Hex-c | 4-Me | — | |
| 3-155 | NHCO$_2$CH$_2$CH$_2$NHCO$_2$Bu-t | 4-Me | — | |
| 3-156 | NHCO$_2$CH$_2$CH$_2$NHCO$_2$Et | 4-Me | — | |
| 3-157 | NHCO$_2$CH$_2$CH$_2$CH$_2$NHCOCH$_3$ | 4-Me | — | |
| 3-158 | NHCO$_2$CH$_2$CH$_2$CH$_2$NHMe$_2$ | 4-Me | — | |
| 3-159 | NHCO$_2$CH$_2$CH$_2$N(Me)COCH$_3$ | 4-Me | — | |
| 3-160 | NHCO$_2$CH$_2$CH$_2$NHCOPh | 4-Me | — | |
| 3-161 | NHCO$_2$CH$_2$CH$_2$N(Me)COPh | 4-Me | — | |
| 3-162 | NHCO$_2$CH$_2$CH$_2$NHPh | 4-Me | — | |
| 3-163 | NHCO$_2$(CH$_2$)$_4$NH$_2$ | 4-Me | — | |
| 3-164 | NHCO$_2$CH$_2$NHCH$_2$Ph | 4-Me | — | |
| 3-165 | NHCO$_2$CH$_2$N(CH$_2$Ph)(CO$_2$Bu-t) | 4-Me | — | |
| 3-166 | NHCO$_2$CH$_2$C$_3$H$_5$-c | 4-Me | — | |
| 3-167 | NHCO$_2$CH(CH$_3$)C$_3$H$_5$-c | 4-Me | — | |
| 3-168 | NHCO$_2$CH$_2$C$_6$H$_{11}$-c | 4-Me | — | |
| 3-169 | NHCO$_2$CH$_2$Ph | 4-Me | — | |
| 3-170 | NHCO$_2$CH(CH$_3$)CH$_2$Ph | 4-Me | — | |
| 3-171 | NHCO$_2$CH(CH$_3$)Ph | 4-Me | — | |
| 3-172 | NHCO$_2$C(CH$_3$)$_2$Ph | 4-Me | — | |
| 3-173 | NHCO$_2$CH$_2$C$_6$H$_4$CF$_3$-4 | 4-Me | — | |
| 3-174 | NHCO$_2$CH$_2$C$_6$H$_4$CN-4 | 4-Me | — | |
| 3-175 | NHCO$_2$CH$_2$C$_6$H$_4$CN-3 | 4-Me | — | |
| 3-176 | NHCO$_2$CH$_2$C$_6$H$_4$Cl-4 | 4-Me | — | |
| 3-177 | NHCO$_2$CH$_2$C$_6$H$_4$Cl-3 | 4-Me | — | |
| 3-178 | NHCO$_2$CH$_2$C$_6$H$_4$OMe-3 | 4-Me | — | |
| 3-179 | NHCO$_2$CH$_2$C$_6$H$_4$OMe-2 | 4-Me | — | |
| 3-180 | NHCO$_2$CH$_2$C$_6$H$_4$Me-4 | 4-Me | — | |
| 3-181 | NHCO$_2$CH$_2$C$_6$H$_4$Me-3 | 4-Me | — | |
| 3-182 | NHCO$_2$CH$_2$C$_6$H$_4$Me-2 | 4-Me | — | |
| 3-183 | NHCO$_2$CH$_2$C$_6$H$_4$SO$_2$Me-4 | 4-Me | — | |
| 3-184 | NHCO$_2$CH$_2$C$_6$H$_4$SO$_2$Me-3 | 4-Me | — | |
| 3-185 | NHCO$_2$CH$_2$C$_6$H$_4$Ph-4 | 4-Me | — | |
| 3-186 | NHCO$_2$CH$_2$C$_6$H$_4$Ph-3 | 4-Me | — | |
| 3-187 | NHCO$_2$CH$_2$Py-2 | 4-Me | — | |
| 3-188 | NHCO$_2$CH$_2$(6-Me-2-Py) | 4-Me | — | |
| 3-189 | NHCO$_2$C(CH$_3$)$_2$Py-4 | 4-Me | — | |
| 3-190 | NHCO$_2$CH$_2$(2-thiazolyl) | 4-Me | — | |
| 3-191 | NHCO$_2$CH$_2$(2-benzthiazolyl) | 4-Me | — | |
| 3-192 | NHCO$_2$CH$_2$CH$_2$OMe | 4-Me | — | |
| 3-193 | NHCO$_2$CH$_2$CH$_2$OEt | 4-Me | — | |
| 3-194 | NHCO$_2$CH$_2$CH$_2$OPr-i | 4-Me | — | |
| 3-195 | NHCO$_2$CH$_2$CH$_2$OBu-i | 4-Me | — | |
| 3-196 | NHCO$_2$CH$_2$CH$_2$OCH$_2$CH$_2$OMe | 4-Me | — | |
| 3-197 | NHCO$_2$CH$_2$CH$_2$OEt | 4-i-Pr | — | |
| 3-198 | NHCO$_2$CH$_2$CH$_2$OC$_6$H$_4$Cl-4 | 4-Me | — | |
| 3-199 | NHCOCH$_2$OPh | 4-Me | — | |
| 3-200 | NHCOCH$_2$OC$_6$H$_4$F-3 | 4-Me | — | |

TABLE 3-continued

| No | Z | $R_{n2}$ | $(X)_{n1}$ | mp °C. |
|---|---|---|---|---|
| 3-201 | NHCOCH$_2$OC$_6$H$_4$OCF$_3$-3 | 4-Me | — | |
| 3-202 | NHCO$_2$CH$_2$CH$_2$OCH$_2$Ph | 4-Me | — | |
| 3-203 | NHCO$_2$CH$_2$CH$_2$OCH$_2$CH$_2$Ph | 4-Me | — | |
| 3-204 | NHCO$_2$(1,1-dimethyl-3-phenyl-2-pentynyl) | 4-Me | — | |
| 3-205 | NHCO$_2$(CH$_2$)$_4$SMe | 4-Me | — | |
| 3-206 | NHCO$_2$(CH$_2$)$_4$SCF$_3$ | 4-Me | — | |
| 3-207 | NHCO$_2$(CH$_2$)$_4$SPh | 4-Me | — | |
| 3-208 | NHCO$_2$(CH$_2$)$_4$SOMe | 4-Me | — | |
| 3-209 | NHCO$_2$(CH$_2$)$_4$SOCF$_3$ | 4-Me | — | |
| 3-210 | NHCO$_2$(CH$_2$)$_4$SOPh | 4-Me | — | |
| 3-211 | NHCO$_2$(CH$_2$)$_4$SO$_2$Me | 4-Me | — | |
| 3-212 | NHCO$_2$(CH$_2$)$_4$SO$_2$CF$_3$ | 4-Me | — | |
| 3-213 | NHCO$_2$(CH$_2$)$_4$SO$_2$Ph | 4-Me | — | |
| 3-214 | NHCO$_2$Ph | 4-Me | — | |
| 3-215 | NHCO$_2$C$_6$H$_4$OMe-4 | 4-Me | — | |
| 3-216 | NHCONHMe | 4-Me | — | |
| 3-217 | NHCONHC$_2$H$_5$ | 4-Me | — | |
| 3-218 | NHCONHPr-n | 4-Me | — | |
| 3-219 | NHCONHBu-t | 4-Me | — | |
| 3-220 | NHCONHBu-s | 4-Me | — | |
| 3-221 | NHCONH(Hex-n) | 4-Me | — | |
| 3-222 | H | 4-Cl | — | |
| 3-223 | NH$_2$ | 4-Cl | — | |
| 3-224 | NHCHO | 4-Cl | — | |
| 3-225 | NHCOCH$_2$CF$_3$ | 4-Cl | — | |
| 3-226 | NHCOC$_2$F$_5$ | 4-Cl | — | |
| 3-227 | NHCOCH$_2$CH$_2$F | 4-Cl | — | |
| 3-228 | NHCOC(CH$_3$)$_2$CF$_3$ | 4-Cl | — | |
| 3-229 | NHCOCH$_2$CH$_2$CF$_3$ | 4-Cl | — | |
| 3-230 | NHCOCH$_2$C$_2$F$_5$ | 4-Cl | — | |
| 3-231 | NHCOCH$_2$CH=CH$_2$ | 4-Cl | — | |
| 3-232 | NHCOCH$_2$CH=CMe$_2$ | 4-Cl | — | |
| 3-233 | NHCOC(CH$_3$)$_2$CH=CH$_2$ | 4-Cl | — | |
| 3-234 | NHCOC(CH$_3$)$_2$CH=CHCH$_3$ | 4-Cl | — | |
| 3-235 | NHCOCH$_2$CH=CHCl | 4-Cl | — | |
| 3-236 | NHCOCH$_2$CH=CHCF$_3$ | 4-Cl | — | |
| 3-237 | NHCOCH$_2$Cl=Cl$_2$ | 4-Cl | — | |
| 3-238 | NHCO(1,1-dimethyl-2-propynyl) | 4-Cl | — | |
| 3-239 | NHCO(2-butynyl) | 4-Cl | — | |
| 3-240 | NHCO(1,1-dimethyl-2-butynyl) | 4-Cl | — | |
| 3-241 | NHCO(1,1-dimethyl-2-pentynyl) | 4-Cl | — | |
| 3-242 | NHCO(1-propynyl) | 4-Cl | — | |
| 3-243 | NHCO(1,1-dimethyl-3-Iodo-2-pentynyl) | 4-Cl | — | |
| 3-244 | NHCO(4,4,4-trifluoro-2-butynyl) | 4-Cl | — | |
| 3-245 | NHCOPr-c | 4-Cl | — | |
| 3-246 | NHCOHex-c | 4-Cl | — | |
| 3-247 | NHCO(CH$_2$)$_4$CO$_2$H | 4-Cl | — | |
| 3-248 | NHCOCH$_2$CH$_2$NHCO$_2$Bu-t | 4-Cl | — | |
| 3-249 | NHCOCH$_2$CH$_2$NHCO$_2$Et | 4-Cl | — | |
| 3-250 | NHCOCH$_2$CH$_2$CH$_2$NHCOCH$_3$ | 4-Cl | — | |
| 3-251 | NHCOCH$_2$CH$_2$NHMe$_2$ | 4-Cl | — | |
| 3-252 | NHCOCH$_2$CH$_2$N(Me)COCH$_3$ | 4-Cl | — | |
| 3-253 | NHCOCH$_2$CH$_2$NHCOPh | 4-Cl | — | |
| 3-254 | NHCOCH$_2$CH$_2$N(Me)COPh | 4-Cl | — | |
| 3-255 | NHCOCH$_2$CH$_2$NHPh | 4-Cl | — | |
| 3-256 | NHCO(CH$_2$)$_4$NH$_2$ | 4-Cl | — | |

TABLE 3-continued

[Structure diagram showing a pyridine ring with positions labeled 1-6, N at position 1, Z at position 2, R_{n2} at position 4, connected via CH_2-O-N= to a carbon bearing a tetrazole (with CH_3 substituent) and a phenyl ring with (X)_{n1} substituents]

| No | Z | R_{n2} | (X)_{n1} | mp °C. |
|---|---|---|---|---|
| 3-257 | NHCOCH_2NHCH_2Ph | 4-Cl | — | |
| 3-258 | NHCOCH_2N(CH_2Ph)(CO_2Bu-t) | 4-Cl | — | |
| 3-259 | NHCOCH_2CH_2OC_6H_4Cl-4 | 4-Cl | — | |
| 3-260 | NHCOCH_2OPh | 4-Cl | — | |
| 3-261 | NHCOCH_2OC_6H_4F-3 | 4-Cl | — | |
| 3-262 | NHCOCH_2OC_6H_4OCF_3-3 | 4-Cl | — | |
| 3-263 | NHCO(CH_2)_4SMe | 4-Cl | — | |
| 3-264 | NHCOCH_2CH_2OEt | 4-Cl | — | |
| 3-265 | NHCOCH_2CH_2OPr-i | 4-Cl | — | |
| 3-266 | NHCOCH_2CH_2OBu-i | 4-Cl | — | |
| 3-267 | NHCOCH_2CH_2OCH_2CH_2OMe | 4-Cl | — | |
| 3-268 | NHCO_2CH_3 | 4-Cl | — | |
| 3-269 | NHCO_2C_2H_5 | 4-Cl | — | |
| 3-270 | NHCO_2Pr-n | 4-Cl | — | |
| 3-271 | NHCO_2Pr-i | 4-Cl | — | |
| 3-272 | NHCO_2Bu-n | 4-Cl | — | |
| 3-273 | NHCO_2Bu-i | 4-Cl | — | |
| 3-274 | NHCO_2Bu-s | 4-Cl | — | |
| 3-275 | NHCO_2Bu-t | 4-Cl | — | |
| 3-276 | NHCO_2Bu-t | 5-Br | — | |
| 3-277 | NHCO_2Bu-t | 5-Cl | — | |
| 3-278 | NHCO_2Bu-t | 4-Br | — | |
| 3-279 | NHCO_2Bu-t | 4-Cl | 2-Cl | |
| 3-280 | NHCO_2Bu-t | 4-Cl | 3-Cl | |
| 3-281 | NHCO_2Bu-t | 4-Cl | 4-Cl | |
| 3-282 | NHCO_2Bu-t | 4-Cl | 2,4-Cl_2 | |
| 3-283 | NHCO_2Bu-t | 4-Cl | 3,5-Cl_2 | |
| 3-284 | NHCO_2Bu-t | 4-Cl | 3,4,5-Cl_3 | |
| 3-285 | NHCO_2Bu-t | 4-Cl | 2-Me | |
| 3-286 | NHCO_2CH_2CF_3 | 4-Cl | — | |
| 3-287 | NHCO_2C_2F_5 | 4-Cl | — | |
| 3-288 | NHCO_2CH_2CH_2F | 4-Cl | — | |
| 3-289 | NHCO_2C(CH_3)_2CF_3 | 4-Cl | — | |
| 3-290 | NHCO_2CH_2CH_2CF_3 | 4-Cl | — | |
| 3-291 | NHCO_2CH_2C_2F_5 | 4-Cl | — | |
| 3-292 | NHCO_2CH_2CH=CH_2 | 4-Cl | — | |
| 3-293 | NHCO_2CH_2CH=CMe_2 | 4-Cl | — | |
| 3-294 | NHCO_2C(CH_3)_2CH=CH_2 | 4-Cl | — | |
| 3-295 | NHCO_2C(CH_3)_2CH=CHCH_3 | 4-Cl | — | |
| 3-296 | NHCO_2CH_2CH=CHCl | 4-Cl | — | |
| 3-297 | NHCO_2CH_2CH=CHCF_3 | 4-Cl | — | |
| 3-298 | NHCO_2CH_2Cl=Cl_2 | 4-Cl | — | |
| 3-299 | NHCO_2(1,1-dimethyl-2-propynyl) | 4-Cl | — | |
| 3-300 | NHCO_2(2-butynyl) | 4-Cl | — | |
| 3-301 | NHCO_2(1,1-dimethyl-2-butynyl) | 4-Cl | — | |
| 3-302 | NHCO_2(1,1-dimethyl-2-pentynyl) | 4-Cl | — | |
| 3-303 | NHCO_2(1-propynyl) | 4-Cl | — | |
| 3-304 | NHCO_2(1,1-dimethyl-3-Iodo-2-pentynyl) | 4-Cl | — | |
| 3-305 | NHCO_2(4,4,4-trifluoro-2-butynyl) | 4-Cl | — | |
| 3-306 | NHCO_2Pr-c | 4-Cl | — | |
| 3-307 | NHCO_2Hex-c | 4-Cl | — | |
| 3-308 | NHCO_2CH_2CH_2NHCO_2Bu-t | 4-Cl | — | |
| 3-309 | NHCO_2CH_2CH_2NHCO_2Et | 4-Cl | — | |
| 3-310 | NHCO_2CH_2CH_2CH_2NHCOCH_3 | 4-Cl | — | |
| 3-311 | NHCO_2CH_2CH_2CH_2NMe_2 | 4-Cl | — | |
| 3-312 | NHCO_2CH_2CH_2N(Me)COCH_3 | 4-Cl | — | |

TABLE 3-continued

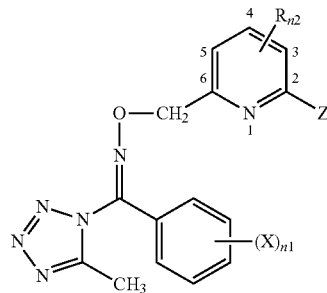

| No | Z | $R_{n2}$ | $(X)_{n1}$ | mp °C. |
|---|---|---|---|---|
| 3-313 | NHCO$_2$CH$_2$CH$_2$NHCOPh | 4-Cl | — | |
| 3-314 | NHCO$_2$CH$_2$CH$_2$N(Me)COPh | 4-Cl | — | |
| 3-315 | NHCO$_2$CH$_2$CH$_2$NHPh | 4-Cl | — | |
| 3-316 | NHCO$_2$(CH$_2$)$_4$NH$_2$ | 4-Cl | — | |
| 3-317 | NHCO$_2$CH$_2$NHCH$_2$Ph | 4-Cl | — | |
| 3-318 | NHCO$_2$CH$_2$N(CH$_2$Ph)(CO$_2$Bu-t) | 4-Cl | — | |
| 3-319 | NHCO$_2$CH$_2$C$_3$H$_5$-c | 4-Cl | — | |
| 3-320 | NHCO$_2$CH(CH$_3$)C$_3$H$_5$-c | 4-Cl | — | |
| 3-321 | NHCO$_2$CH$_2$C$_6$H$_{11}$-c | 4-Cl | — | |
| 3-322 | NHCO$_2$CH$_2$Ph | 4-Cl | — | |
| 3-323 | NHCO$_2$CH$_2$Ph | 5-Cl | — | |
| 3-324 | NHCO$_2$CH(CH$_3$)CH$_2$Ph | 4-Cl | — | |
| 3-325 | NHCO$_2$CH(CH$_3$)Ph | 4-Cl | — | |
| 3-326 | NHCO$_2$C(CH$_3$)$_2$Ph | 4-Cl | — | |
| 3-327 | NHCO$_2$CH$_2$C$_6$H$_4$CF$_3$-4 | 4-Cl | — | |
| 3-328 | NHCO$_2$CH$_2$C$_6$H$_4$CN-4 | 4-Cl | — | |
| 3-329 | NHCO$_2$CH$_2$C$_6$H$_4$CN-3 | 4-Cl | — | |
| 3-330 | NHCO$_2$CH$_2$C$_6$H$_4$Cl-4 | 4-Cl | — | |
| 3-331 | NHCO$_2$CH$_2$C$_6$H$_4$Cl-3 | 4-Cl | — | |
| 3-332 | NHCO$_2$CH$_2$C$_6$H$_4$OMe-3 | 4-Cl | — | |
| 3-333 | NHCO$_2$CH$_2$C$_6$H$_4$OMe-2 | 4-Cl | — | |
| 3-334 | NHCO$_2$CH$_2$C$_6$H$_4$Me-4 | 4-Cl | — | |
| 3-335 | NHCO$_2$CH$_2$C$_6$H$_4$Me-3 | 4-Cl | — | |
| 3-336 | NHCO$_2$CH$_2$C$_6$H$_4$Me-2 | 4-Cl | — | |
| 3-337 | NHCO$_2$CH$_2$C$_6$H$_4$SO$_2$Me-4 | 4-Cl | — | |
| 3-338 | NHCO$_2$CH$_2$C$_6$H$_4$SO$_2$Me-3 | 4-Cl | — | |
| 3-339 | NHCO$_2$CH$_2$C$_6$H$_4$Ph-4 | 4-Cl | — | |
| 3-340 | NHCO$_2$CH$_2$C$_6$H$_4$Ph-3 | 4-Cl | — | |
| 3-341 | NHCO$_2$CH$_2$Py-2 | 4-Cl | — | |
| 3-342 | NHCO$_2$CH$_2$(6-Me-2-Py) | 4-Cl | — | |
| 3-343 | NHCO$_2$C(CH$_3$)$_2$Py-4 | 4-Cl | — | |
| 3-344 | NHCO$_2$CH$_2$(2-thiazolyl) | 4-Cl | — | |
| 3-345 | NHCO$_2$CH$_2$(2-benzthiazolyl) | 4-Cl | — | |
| 3-346 | NHCO$_2$CH$_2$CH$_2$OMe | 4-Cl | — | |
| 3-347 | NHCO$_2$CH$_2$CH$_2$OEt | 4-Cl | — | |
| 3-348 | NHCO$_2$CH$_2$CH$_2$OPr-i | 4-Cl | — | |
| 3-349 | NHCO$_2$CH$_2$CH$_2$OBu-i | 4-Cl | — | |
| 3-350 | NHCO$_2$CH$_2$CH$_2$OCH$_2$OMe | 4-Cl | — | |
| 3-351 | NHCO$_2$CH$_2$CH$_2$OC$_6$H$_4$Cl-4 | 4-Cl | — | |
| 3-352 | NHCOCH$_2$OPh | 4-Cl | — | |
| 3-353 | NHCOCH$_2$OC$_6$H$_4$F-3 | 4-Cl | — | |
| 3-354 | NHCOCH$_2$OC$_6$H$_4$OCF$_3$-3 | 4-Cl | — | |
| 3-355 | NHCO$_2$CH$_2$CH$_2$OCH$_2$Ph | 4-Cl | — | |
| 3-356 | NHCO$_2$(1,1-dimethyl-3-phenyl-2-pentynyl) | 4-Cl | — | |
| 3-357 | NHCO$_2$CH$_2$CH$_2$OCH$_2$CH$_2$Ph | 4-Cl | — | |
| 3-358 | NHCO$_2$(1,1-dimethyl-3-phenyl-2-pentynyl) | 4-Cl | — | |
| 3-359 | NHCO$_2$(CH$_2$)$_4$SMe | 4-Cl | — | |
| 3-360 | NHCO$_2$(CH$_2$)$_4$SCF$_3$ | 4-Cl | — | |
| 3-361 | NHCO$_2$(CH$_2$)$_4$SPh | 4-Cl | — | |
| 3-362 | NHCO$_2$(CH$_2$)$_4$SOMe | 4-Cl | — | |
| 3-363 | NHCO$_2$(CH$_2$)$_4$SOCF$_3$ | 4-Cl | — | |
| 3-364 | NHCO$_2$(CH$_2$)$_4$SOPh | 4-Cl | — | |
| 3-365 | NHCO$_2$(CH$_2$)$_4$SO$_2$Me | 4-Cl | — | |
| 3-366 | NHCO$_2$(CH$_2$)$_4$SO$_2$CF$_3$ | 4-Cl | — | |
| 3-367 | NHCO$_2$(CH$_2$)$_4$SO$_2$Ph | 4-Cl | — | |
| 3-368 | NHCO$_2$Ph | 4-Cl | — | |
| 3-369 | NHCO$_2$C$_6$H$_4$OMe-4 | 4-Cl | — | |
| 3-370 | NHCONHMe | 4-Cl | — | |
| 3-371 | NHCONHC$_2$H$_5$ | 4-Cl | — | |
| 3-372 | NHCONHPr-n | 4-Cl | — | |

TABLE 3-continued

| No | Z | R$_{n2}$ | (X)$_{n1}$ | mp °C. |
|---|---|---|---|---|
| 3-373 | NHCONHBu-t | 4-Cl | — | |
| 3-374 | NHCONHBu-s | 4-Cl | — | |
| 3-375 | NHCONH(Hex-n) | 4-Cl | — | |
| 3-376 | NHCOCH$_2$CF$_3$ | — | — | |
| 3-377 | NHCOC$_2$F$_5$ | — | — | |
| 3-378 | NHCOCH$_2$CH$_2$F | — | — | |
| 3-379 | NHCOC(CH$_3$)$_2$CF$_3$ | — | — | |
| 3-380 | NHCOCH$_2$CH$_2$CF$_3$ | — | — | |
| 3-381 | NHCOCH$_2$C$_2$F$_5$ | — | — | |
| 3-382 | NHCOCH$_2$CH=CH$_2$ | — | — | |
| 3-383 | NHCOCH$_2$CH=CMe$_2$ | — | — | |
| 3-384 | NHCOC(CH$_3$)$_2$CH=CH$_2$ | — | — | |
| 3-385 | NHCOC(CH$_3$)$_2$CH=CHCH$_3$ | — | — | |
| 3-386 | NHCOCH$_2$CH=CHCl | — | — | |
| 3-387 | NHCOCH$_2$CH=CHCF$_3$ | — | — | |
| 3-388 | NHCOCH$_2$Cl=Cl$_2$ | — | — | |
| 3-389 | NHCO(1,1-dimethyl-2-propynyl) | — | — | |
| 3-390 | NHCO(2-butynyl) | — | — | |
| 3-391 | NHCO(1,1-dimethyl-2-butynyl) | — | — | |
| 3-392 | NHCO(1,1-dimethyl-2-pentynyl) | — | — | |
| 3-393 | NHCO(1-propynyl) | — | — | |
| 3-394 | NHCO(1,1-dimethyl-3-Iodo-2-pentynyl) | — | — | |
| 3-395 | NHCO(4,4,4-trifluoro-2-butynyl) | — | — | |
| 3-396 | NHCO(CH$_2$)$_4$CO$_2$H | — | — | |
| 3-397 | NHCOCH$_2$CH$_2$NHMe$_2$ | — | — | |
| 3-398 | NHCO(CH$_2$)$_4$NH$_2$ | — | — | |
| 3-399 | NHCOCH$_2$NHCH$_2$Ph | — | — | |
| 3-400 | NHCOCH$_2$N(CH$_2$Ph)(CO$_2$Bu-t) | — | — | |
| 3-401 | NHCOCH$_2$CH$_2$NMe$_2$ | — | — | |
| 3-402 | NHCOCH$_2$CH$_2$NHEt | — | — | |
| 3-403 | NHCOCH$_2$CH$_2$NHPr-n | — | — | |
| 3-404 | NHCOCH$_2$CH$_2$OC$_6$H$_4$Cl-4 | — | — | |
| 3-405 | NHCOCH$_2$OPh | — | — | |
| 3-406 | NHCOCH$_2$OC$_6$H$_4$F-3 | — | — | |
| 3-407 | NHCOCH$_2$OC$_6$H$_4$OCF$_3$-3 | — | — | |
| 3-408 | NHCOCH$_2$OC$_6$H$_4$CN-2 | — | — | |
| 3-409 | NHCOCH$_2$OC$_6$H$_4$F-4 | — | — | |
| 3-410 | NHCOCH$_2$OC$_6$H$_3$(3,4-methylenedioxy) | — | — | |
| 3-411 | NHCOCH$_2$OC$_6$H$_4$(CONH$_2$)-2 | — | — | |
| 3-412 | NHCOCH$_2$OC$_6$H$_3$(3,4-(OCH$_3$)$_2$) | — | — | |
| 3-413 | NHCOCH$_2$O(6-CF$_3$-pyrimidin-4-yl) | — | — | |
| 3-414 | NHCOCH$_2$O(3-Py) | — | — | |
| 3-415 | NHCO$_2$CH$_2$CF$_3$ | — | — | |
| 3-416 | NHCO$_2$C$_2$F$_5$ | — | — | |
| 3-417 | NHCO$_2$CH$_2$CH$_2$F | — | — | |
| 3-418 | NHCO$_2$C(CH$_3$)$_2$CF$_3$ | — | — | |
| 3-419 | NHCO$_2$CH$_2$CH$_2$CF$_3$ | — | — | |
| 3-420 | NHCO$_2$CH$_2$C$_2$F$_5$ | — | — | |
| 3-421 | NHCO$_2$CH$_2$CH=CH$_2$ | — | — | |
| 3-422 | NHCO$_2$CH$_2$CH=CMe$_2$ | — | — | |
| 3-423 | NHCO$_2$C(CH$_3$)$_2$CH=CH$_2$ | — | — | |
| 3-424 | NHCO$_2$C(CH$_3$)$_2$CH=CHCH$_3$ | — | — | |
| 3-425 | NHCO$_2$CH$_2$CH=CHCl | — | — | |
| 3-426 | NHCO$_2$CH$_2$CH=CHCF$_3$ | — | — | |
| 3-427 | NHCO$_2$CH$_2$Cl=Cl$_2$ | — | — | |

TABLE 3-continued

| No | Z | $R_{n2}$ | $(X)_{n1}$ | mp °C. |
|---|---|---|---|---|
| 3-428 | $NHCO_2$(1,1-dimethyl-2-propynyl) | — | — | |
| 3-429 | $NHCO_2$(2-butynyl) | — | — | |
| 3-430 | $NHCO_2$(1,1-dimethyl-2-butynyl) | — | — | |
| 3-431 | $NHCO_2$(1,1-dimethyl-2-pentynyl) | — | — | |
| 3-432 | $NHCO_2$(1-propynyl) | — | — | |
| 3-433 | $NHCO_2$(1,1-dimethyl-3-Iodo-2-pentynyl) | — | — | |
| 3-434 | $NHCO_2$(4,4,4-trifluoro-2-butynyl) | — | — | |
| 3-435 | $NHCO_2$(1,1-dimethyl-3-phenyl-2-pentynyl) | — | — | |
| 3-436 | $NHCO_2CH_2CH_2NHCO_2Bu$-t | — | — | |
| 3-437 | $NHCO_2CH_2CH_2NHCO_2Et$ | — | — | |
| 3-438 | $NHCO_2CH_2N(CH_2Ph)(CO_2Bu$-t$)$ | — | — | |
| 3-439 | $NHCO_2CH_2NCH_2Ph$ | — | — | |
| 3-440 | $NHCO_2CH_2CH_2NCH_2Ph$ | — | — | |
| 3-441 | $NHCO_2CH_2CH_2NCH_2C_6H_4Cl$-4 | — | — | |
| 3-442 | $NHCO_2CH_2CH_2NHMe$ | — | — | |
| 3-443 | $NHCO_2CH_2C(CH_3)_2N(CH_3)_2$ | — | — | |
| 3-444 | $NHCO_2CH(CH_3)CH_2N(CH_3)_2$ | — | — | |
| 3-445 | $NHCO_2CH_2C_3H_5$-c | — | — | |
| 3-446 | $NHCO_2CH(CH_3)C_3H_5$-c | — | — | |
| 3-447 | $NHCO_2CH_2C_6H_{11}$-c | — | — | |
| 3-448 | $NHCO_2CH(CH_3)CH_2Ph$ | — | — | |
| 3-449 | $NHCO_2CH(CH_3)Ph$ | — | — | |
| 3-450 | $NHCO_2C(CH_3)_2Ph$ | — | — | |
| 3-451 | $NHCO_2CH_2C_6H_4CF_3$-4 | — | — | |
| 3-452 | $NHCO_2CH_2C_6H_4CN$-4 | — | — | |
| 3-453 | $NHCO_2CH_2C_6H_4CN$-3 | — | — | |
| 3-454 | $NHCO_2CH_2C_6H_4Cl$-4 | — | — | |
| 3-455 | $NHCO_2CH_2C_6H_4Cl$-3 | — | — | |
| 3-456 | $NHCO_2CH_2C_6H_4OMe$-3 | — | — | |
| 3-457 | $NHCO_2CH_2C_6H_4OMe$-2 | — | — | |
| 3-458 | $NHCO_2CH_2C_6H_4Me$-4 | — | — | |
| 3-459 | $NHCO_2CH_2C_6H_4Me$-3 | — | — | |
| 3-460 | $NHCO_2CH_2C_6H_4Me$-2 | — | — | |
| 3-461 | $NHCO_2CH_2C_6H_4SO_2Me$-4 | — | — | |
| 3-462 | $NHCO_2CH_2C_6H_4SO_2Me$-3 | — | — | |
| 3-463 | $NHCO_2CH_2C_6H_4Ph$-4 | — | — | |
| 3-464 | $NHCO_2CH_2C_6H_4Ph$-3 | — | — | |
| 3-465 | $NHCO_2CH_2C_6H_4OCH_3$-4 | — | — | |
| 3-466 | $NHCO_2CH_2C_6H_3$(3,4-methylenedioxy) | — | — | |
| 3-467 | $NHCO_2CH_2Py$-2 | — | — | |
| 3-468 | $NHCO_2CH_2$(6-Me-2-Py) | — | — | |
| 3-469 | $NHCO_2C(CH_3)_2Py$-4 | — | — | |
| 3-470 | $NHCO_2CH_2$(2-thiazolyl) | — | — | |
| 3-471 | $NHCO_2CH_2$(2-benzthiazolyl) | — | — | |
| 3-472 | $NHCO_2CH_2$(3-Py) | — | — | |
| 3-473 | $NHCO_2CH_2$(4-Py) | — | — | |
| 3-474 | $NHCO_2CH(CH_3)$(4-Py) | — | — | |
| 3-475 | $NHCO_2CH_2CH_2OMe$ | — | — | |
| 3-476 | $NHCO_2CH_2CH_2OEt$ | — | — | |
| 3-477 | $NHCO_2CH_2CH_2OPr$-i | — | — | |
| 3-478 | $NHCO_2CH_2CH_2OBu$-i | — | — | |
| 3-479 | $NHCO_2CH_2CH_2OCH_2OMe$ | — | — | |
| 3-480 | $NHCO_2C(CH_3)_2CH_2OCH_3$ | — | — | |
| 3-481 | $NHCO_2CH(CH_3)CH_2OCH_3$ | — | — | |
| 3-482 | $NHCO_2CH_2CH_2OC_6H_4Cl$-4 | — | — | |

TABLE 3-continued

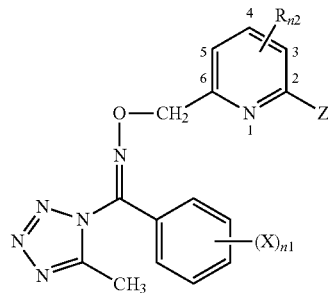

| No | Z | R$_{n2}$ | (X)$_{n1}$ | mp °C. |
|---|---|---|---|---|
| 3-483 | NHCO$_2$CH$_2$OPh | — | — | |
| 3-484 | NHCO$_2$CH$_2$OC$_6$H$_4$F-3 | — | — | |
| 3-485 | NHCO$_2$CH$_2$OC$_6$H$_4$OCF$_3$-3 | — | — | |
| 3-486 | NHCO$_2$CH$_2$CH$_2$OCH$_2$Ph | — | — | |
| 3-487 | NHCO$_2$CH$_2$CH$_2$OCH$_2$CH$_2$Ph | — | — | |
| 3-488 | NHCO$_2$(CH$_2$)$_4$SMe | — | — | |
| 3-489 | NHCO$_2$(CH$_2$)$_4$SCF$_3$ | — | — | |
| 3-490 | NHCO$_2$(CH$_2$)$_4$SPh | — | — | |
| 3-491 | NHCO$_2$(CH$_2$)$_4$SOMe | — | — | |
| 3-492 | NHCO$_2$(CH$_2$)$_4$SOCF$_3$ | — | — | |
| 3-493 | NHCO$_2$(CH$_2$)$_4$SOPh | — | — | |
| 3-494 | NHCO$_2$(CH$_2$)$_4$SO$_2$Me | — | — | |
| 3-495 | NHCO$_2$(CH$_2$)$_4$SO$_2$CF$_3$ | — | — | |
| 3-496 | NHCO$_2$(CH$_2$)$_4$SO$_2$Ph | — | — | |
| 3-497 | NHCO$_2$Ph | — | — | |
| 3-498 | NHCO$_2$C$_6$H$_4$OMe-4 | — | — | |
| 3-499 | NHCOCH$_2$CH$_2$CH$_2$COCH$_3$ | — | — | |

TABLE 4

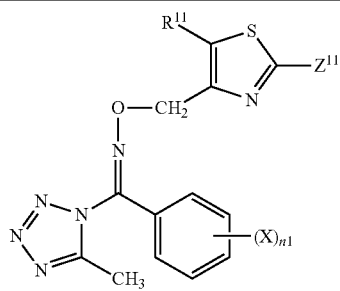

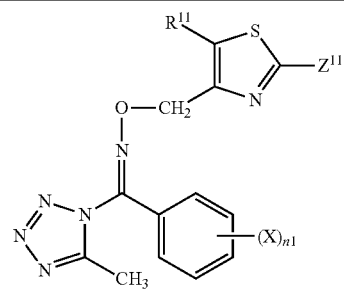

| No | Z$^{11}$ | R$^{11}$ | (X)$_{n1}$ | mp °C. | No | Z$^{11}$ | R$^{11}$ | (X)$_{n1}$ | mp °C. |
|---|---|---|---|---|---|---|---|---|---|
| 4-1 | H | Me | — | | 4-23 | NHCOCH$_2$CH=CH$_2$ | Me | — | |
| 4-2 | NH$_2$ | Me | — | | 4-24 | NHCOCH$_2$CH=CMe$_2$ | Me | — | |
| 4-3 | NH$_2$ | Bu-t | — | | 4-25 | NHCOC(CH$_3$)$_2$CH=CH$_2$ | Me | — | |
| 4-4 | NH$_2$ | OC$_2$H$_5$ | — | | 4-26 | NHCOC(CH$_3$)$_2$CH=CHCH$_3$ | Me | — | |
| 4-5 | NH$_2$ | OCH$_3$ | — | | 4-27 | NHCOCH$_2$CH=CHCl | Me | — | |
| 4-6 | NH$_2$ | C$_2$H$_5$ | — | | 4-28 | NHCOCH$_2$CH=CHCF$_3$ | Me | — | |
| 4-7 | NHCHO | Me | — | | 4-29 | NHCOCH$_2$Cl=Cl$_2$ | Me | — | |
| 4-8 | NHCOCH$_3$ | Me | — | | 4-30 | NHCO(1,1-dimethyl-2-propynyl) | Me | — | |
| 4-9 | NHCOC$_2$H$_5$ | Me | — | | | | | | |
| 4-10 | NHCOPr-n | Me | — | | 4-31 | NHCO(2-butynyl) | Me | — | |
| 4-11 | NHCOPr-i | Me | — | | 4-32 | NHCO(1,1-dimethyl-2-butynyl) | Me | — | |
| 4-12 | NHCOBu-n | Me | — | | | | | | |
| 4-13 | NHCOBu-i | Me | — | | 4-33 | NHCO(1,1-dimethyl-2-pentynyl) | Me | — | |
| 4-14 | NHCOBu-s | Me | — | | | | | | |
| 4-15 | NHCOBu-t | Me | — | | 4-34 | NHCO(1-propynyl) | Me | — | |
| 4-16 | NHCOBu-t | OMe | — | | 4-35 | NHCO(1,1-dimethyl-3-Iodo-2-pentynyl) | Me | — | |
| 4-17 | NHCOCH$_2$CF$_3$ | Me | — | | | | | | |
| 4-18 | NHCOC$_2$F$_5$ | Me | — | | 4-36 | NHCO(4,4,4-trifluoro-2-butynyl) | Me | — | |
| 4-19 | NHCOCH$_2$CH$_2$F | Me | — | | | | | | |
| 4-20 | NHCOC(CH$_3$)$_2$CF$_3$ | Me | — | | 4-37 | NHCOPr-c | Me | — | |
| 4-21 | NHCOCH$_2$CH$_2$CF$_3$ | Me | — | | 4-38 | NHCOHex-c | Me | — | |
| 4-22 | NHCOCH$_2$C$_2$F$_5$ | Me | — | | 4-39 | NHCO(CH$_2$)$_4$CO$_2$H | Me | — | |

TABLE 4-continued

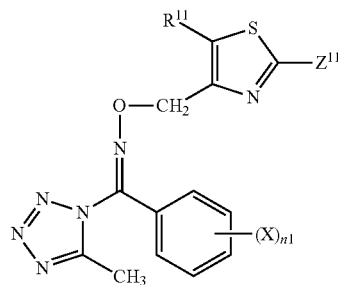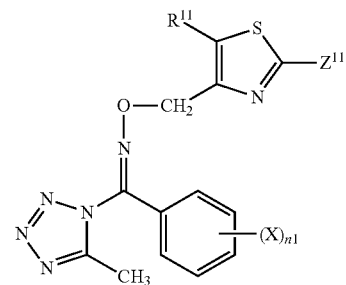

| No | $Z^{11}$ | $R^{11}$ | $(X)_{n1}$ | mp °C. |
|---|---|---|---|---|
| 4-40 | NHCOCH$_2$CH$_2$NHCO$_2$Bu-t | Me | — | |
| 4-41 | NHCOCH$_2$CH$_2$NHCO$_2$Et | Me | — | |
| 4-42 | NHCOCH$_2$CH$_2$CH$_2$NHCOCH$_3$ | Me | — | |
| 4-43 | NHCOCH$_2$CH$_2$CH$_2$NHMe$_2$ | Me | — | |
| 4-44 | NHCOCH$_2$CH$_2$N(Me)COCH$_3$ | Me | — | |
| 4-45 | NHCOCH$_2$CH$_2$NHCOPh | Me | — | |
| 4-46 | NHCOCH$_2$CH$_2$N(Me)COPh | Me | — | |
| 4-47 | NHCOCH$_2$CH$_2$NHPh | Me | — | |
| 4-48 | NHCO(CH$_2$)$_4$NH$_2$ | Me | — | |
| 4-49 | NHCOCH$_2$NHCH$_2$Ph | Me | — | |
| 4-50 | NHCOCH$_2$N(CH$_2$Ph)(CO$_2$Bu-t) | Me | — | |
| 4-51 | NHCOCH$_2$CH$_2$OC$_6$H$_4$Cl-4 | Me | — | |
| 4-52 | NHCOCH$_2$OPh | Me | — | |
| 4-53 | NHCOCH$_2$OC$_6$H$_4$F-3 | Me | — | |
| 4-54 | NHCOCH$_2$OC$_6$H$_4$OCF$_3$-3 | Me | — | |
| 4-55 | NHCO(CH$_2$)$_4$SMe | Me | — | |
| 4-56 | NHCOCH$_2$CH$_2$OEt | Me | — | |
| 4-57 | NHCOCH$_2$CH$_2$OPr-i | Me | — | |
| 4-58 | NHCOCH$_2$CH$_2$OBu-i | Me | — | |
| 4-59 | NHCOCH$_2$CH$_2$OCH$_2$CH$_2$OMe | Me | — | |
| 4-60 | NHCO$_2$CH$_3$ | Me | — | |
| 4-61 | NHCO$_2$C$_2$H$_5$ | Me | — | |
| 4-62 | NHCO$_2$Pr-n | Me | — | |
| 4-63 | NHCO$_2$Pr-i | Me | — | |
| 4-64 | NHCO$_2$Bu-n | Me | — | |
| 4-65 | NHCO$_2$Bu-i | Me | — | |
| 4-66 | NHCO$_2$Bu-s | Me | — | |
| 4-67 | NHCO$_2$Bu-t | i-Pr | — | |
| 4-68 | NHCO$_2$Bu-t | Me | — | |
| 4-69 | NHCO$_2$Bu-t | t-Bu | — | |
| 4-70 | NHCO$_2$Bu-t | Et | — | |
| 4-71 | NHCO$_2$Bu-t | CH=CH$_2$ | — | |
| 4-72 | NHCO$_2$Bu-t | OMe | — | |
| 4-73 | NHCO$_2$Bu-t | OEt | — | |
| 4-74 | NHCO$_2$Bu-t | OCH$_2$CH$_2$OEt | — | |
| 4-75 | NHCO$_2$Bu-t | OPr-i | — | |
| 4-76 | NHCO$_2$Bu-t | OBu-n | — | |
| 4-77 | NHCO$_2$Bu-t | SMe | — | |
| 4-78 | NHCO$_2$Bu-t | SOMe | — | |
| 4-79 | NHCO$_2$Bu-t | SO$_2$Me | — | |
| 4-80 | NHCO$_2$Bu-t | NMe$_2$ | — | |
| 4-81 | NHCO$_2$Bu-t | N(Me)(CO$_2$Bu-t) | — | |
| 4-82 | NHCO$_2$Bu-t | CN | — | |
| 4-83 | NHCO$_2$Bu-t | morphorino | — | |
| 4-84 | NHCO$_2$Bu-t | Ph | — | |
| 4-85 | NHCO$_2$Bu-t | CO$_2$C$_2$H$_5$ | — | |
| 4-86 | NHCO$_2$Bu-t | CONHCH$_3$ | — | |
| 4-87 | NHCO$_2$Bu-t | CF$_3$ | — | |
| 4-88 | NHCO$_2$Bu-t | OH | — | |
| 4-89 | NHCO$_2$Bu-t | SH | — | |
| 4-90 | NHCO$_2$Bu-t | CH$_2$Cl=Cl$_2$ | — | |
| 4-91 | NHCO$_2$Bu-t | etynyl | — | |
| 4-92 | NHCO$_2$Bu-t | propargyl | — | |
| 4-93 | NHCO$_2$Bu-t | (3-iodo-2-propynyl) | — | |
| 4-94 | NHCO$_2$Bu-t | Ph | — | |
| 4-95 | NHCO$_2$Bu-t | C$_6$H$_4$OMe-4 | — | |
| 4-96 | NHCO$_2$Bu-t | 2-pyridyl | — | |
| 4-97 | NHCO$_2$Bu-t | 4-CF$_3$-2-oxazolyl | — | |
| 4-98 | NHCO$_2$Bu-t | 3-CF$_3$-5-Cl-2-pyridyl | — | |
| 4-99 | NHCO$_2$Bu-t | pyrrolidino | — | |
| 4-100 | NHCO$_2$Bu-t | COMe | — | |
| 4-101 | NHCO$_2$Bu-t | CONHMe | — | |
| 4-102 | NHCO$_2$Bu-t | CONMe$_2$ | — | |
| 4-103 | NHCO$_2$Bu-t | COPr-c | — | |
| 4-104 | NHCO$_2$Bu-t | COPh | — | |
| 4-105 | NHCO$_2$Bu-t | COCH$_2$CH=CH$_2$ | — | |
| 4-106 | NHCO$_2$Bu-t | CO(propargyl) | — | |
| 4-107 | NHCO$_2$Bu-t | CO$_2$Me | — | |
| 4-108 | NHCO$_2$Bu-t | CO$_2$Ph | — | |
| 4-109 | NHCO$_2$Bu-t | CO$_2$CH$_2$CH=CH$_2$ | — | |
| 4-110 | NHCO$_2$Bu-t | CO$_2$(propargyl) | — | |
| 4-111 | NHCO$_2$Bu-t | Me | 2-Cl | |
| 4-112 | NHCO$_2$Bu-t | Me | 3-Cl | |
| 4-113 | NHCO$_2$Bu-t | Me | 4-Cl | |
| 4-114 | NHCO$_2$Bu-t | Me | 2,4-Cl$_2$ | |
| 4-115 | NHCO$_2$Bu-t | Me | 3,5-Cl$_2$ | |
| 4-116 | NHCO$_2$Bu-t | Me | 3,4,5-Cl$_3$ | |
| 4-117 | NHCO$_2$Bu-t | Me | 2-Me | |
| 4-118 | NHCO$_2$Bu-n | NH$_2$ | — | |
| 4-119 | NHCO$_2$Bu-n | NHCO$_2$Bu-t | — | |
| 4-120 | NHCO$_2$CH$_2$CF$_3$ | Me | — | |
| 4-121 | NHCO$_2$C$_2$F$_5$ | Me | — | |
| 4-122 | NHCO$_2$CH$_2$CH$_2$F | Me | — | |
| 4-123 | NHCO$_2$C(CH$_3$)$_2$CF$_3$ | Me | — | |
| 4-124 | NHCO$_2$CH$_2$CH$_2$CF$_3$ | Me | — | |
| 4-125 | NHCO$_2$CH$_2$C$_2$F$_5$ | Me | — | |
| 4-126 | NHCO$_2$CH$_2$CH=CH$_2$ | Me | — | |
| 4-127 | NHCO$_2$CH$_2$CH=CMe$_2$ | Me | — | |
| 4-128 | NHCO$_2$C(CH$_3$)$_2$CH=CH$_2$ | Me | — | |
| 4-129 | NHCO$_2$C(CH$_3$)$_2$CH=CHCH$_3$ | Me | — | |
| 4-130 | NHCO$_2$CH$_2$CH=CHCl | Me | — | |
| 4-131 | NHCO$_2$CH$_2$CH=CHCF$_3$ | Me | — | |
| 4-132 | NHCO$_2$CH$_2$Cl=Cl$_2$ | Me | — | |
| 4-133 | NHCO$_2$(1,1-dimethyl-2-propynyl) | Me | — | |
| 4-134 | NHCO$_2$(2-butynyl) | Me | — | |
| 4-135 | NHCO$_2$(1,1-dimethyl-2-butynyl) | Me | — | |
| 4-136 | NHCO$_2$(1,1-dimethyl-2-pentynyl) | Me | — | |
| 4-137 | NHCO$_2$(1-propynyl) | Me | — | |
| 4-138 | NHCO$_2$(1,1-dimethyl-3-Iodo-2-pentynyl) | Me | — | |
| 4-139 | NHCO$_2$(4,4,4-trifluoro-2-butynyl) | Me | — | |
| 4-140 | NHCO$_2$Pr-c | Me | — | |
| 4-141 | NHCO$_2$Hex-c | Me | — | |
| 4-142 | NHCO$_2$CH$_2$CH$_2$NHCO$_2$Bu-t | Me | — | |
| 4-143 | NHCO$_2$CH$_2$CH$_2$NHCO$_2$Et | Me | — | |
| 4-144 | NHCO$_2$CH$_2$CH$_2$CH$_2$NHCOCH$_3$ | Me | — | |
| 4-145 | NHCO$_2$CH$_2$CH$_2$NHMe$_2$ | Me | — | |
| 4-146 | NHCO$_2$CH$_2$CH$_2$N(Me)COCH$_3$ | Me | — | |
| 4-147 | NHCO$_2$CH$_2$CH$_2$NHCOPh | Me | — | |
| 4-148 | NHCO$_2$CH$_2$CH$_2$N(Me)COPh | Me | — | |
| 4-149 | NHCO$_2$CH$_2$CH$_2$NHPh | Me | — | |
| 4-150 | NHCO$_2$(CH$_2$)$_4$NH$_2$ | Me | — | |
| 4-151 | NHCO$_2$CH$_2$NHCH$_2$Ph | Me | — | |

TABLE 4-continued

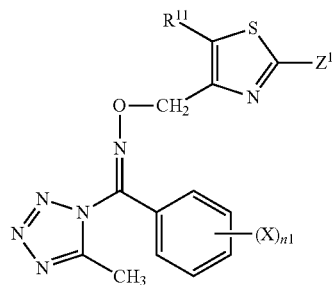

| No | $Z^{11}$ | $R^{11}$ | $(X)_{n1}$ | mp °C. |
|---|---|---|---|---|
| 4-152 | NHCO$_2$CH$_2$N(CH$_2$Ph)(CO$_2$Bu-t) | Me | — | |
| 4-153 | NHCO$_2$CH$_2$C$_3$H$_5$-c | Me | — | |
| 4-154 | NHCO$_2$CH(CH$_3$)C$_3$H$_5$-c | Me | — | |
| 4-155 | NHCO$_2$CH$_2$C$_6$H$_{11}$-c | Me | — | |
| 4-156 | NHCO$_2$CH$_2$Ph | Me | — | |
| 4-157 | NHCO$_2$CH(CH$_3$)CH$_2$Ph | Me | — | |
| 4-158 | NHCO$_2$CH(CH$_3$)Ph | Me | — | |
| 4-159 | NHCO$_2$C(CH$_3$)$_2$Ph | Me | — | |
| 4-160 | NHCO$_2$CH$_2$C$_6$H$_4$CF$_3$-4 | Me | — | |
| 4-161 | NHCO$_2$CH$_2$C$_6$H$_4$CN-4 | Me | — | |
| 4-162 | NHCO$_2$CH$_2$C$_6$H$_4$CN-3 | Me | — | |
| 4-163 | NHCO$_2$CH$_2$C$_6$H$_4$Cl-4 | Me | — | |
| 4-164 | NHCO$_2$CH$_2$C$_6$H$_4$Cl-3 | Me | — | |
| 4-165 | NHCO$_2$CH$_2$C$_6$H$_4$OMe-3 | Me | — | |
| 4-166 | NHCO$_2$CH$_2$C$_6$H$_4$OMe-2 | Me | — | |
| 4-167 | NHCO$_2$CH$_2$C$_6$H$_4$Me-4 | Me | — | |
| 4-168 | NHCO$_2$CH$_2$C$_6$H$_4$Me-3 | Me | — | |
| 4-169 | NHCO$_2$CH$_2$C$_6$H$_4$Me-2 | Me | — | |
| 4-170 | NHCO$_2$CH$_2$C$_6$H$_4$SO$_2$Me-4 | Me | — | |
| 4-171 | NHCO$_2$CH$_2$C$_6$H$_4$SO$_2$Me-3 | Me | — | |
| 4-172 | NHCO$_2$CH$_2$C$_6$H$_4$Ph-4 | Me | — | |
| 4-173 | NHCO$_2$CH$_2$C$_6$H$_4$Ph-3 | Me | — | |
| 4-174 | NHCO$_2$CH$_2$Py-2 | Me | — | |
| 4-175 | NHCO$_2$CH$_2$(6-Me-2-Py) | Me | — | |
| 4-176 | NHCO$_2$C(CH$_3$)$_2$Py-4 | Me | — | |
| 4-177 | NHCO$_2$CH$_2$(2-thiazolyl) | Me | — | |
| 4-178 | NHCO$_2$CH$_2$(2-benzthiazolyl) | Me | — | |
| 4-179 | NHCO$_2$CH$_2$CH$_2$OMe | Me | — | |
| 4-180 | NHCO$_2$CH$_2$CH$_2$OEt | Me | — | |
| 4-181 | NHCO$_2$CH$_2$CH$_2$OPr-i | Me | — | |
| 4-182 | NHCO$_2$CH$_2$CH$_2$OBu-i | Me | — | |
| 4-183 | NHCO$_2$CH$_2$CH$_2$OCH$_2$CH$_2$OMe | Me | — | |
| 4-184 | NHCO$_2$CH$_2$CH$_2$OEt | i-Pr | — | |
| 4-185 | NHCO$_2$CH$_2$CH$_2$OC$_6$H$_4$Cl-4 | Me | — | |
| 4-186 | NHCOCH$_2$OPh | Me | — | |
| 4-187 | NHCOCH$_2$OC$_6$H$_4$F-3 | Me | — | |
| 4-188 | NHCOCH$_2$OC$_6$H$_4$OCF$_3$-3 | Me | — | |
| 4-189 | NHCO$_2$CH$_2$CH$_2$OCH$_2$Ph | Me | — | |
| 4-190 | NHCO$_2$CH$_2$CH$_2$OCH$_2$CH$_2$Ph | Me | — | |
| 4-191 | NHCO$_2$(1,1-dimethyl-3-phenyl-2-pentynyl) | Me | — | |
| 4-192 | NHCO$_2$(CH$_2$)$_4$SMe | Me | — | |
| 4-193 | NHCO$_2$(CH$_2$)$_4$SCF$_3$ | Me | — | |
| 4-194 | NHCO$_2$(CH$_2$)$_4$SPh | Me | — | |
| 4-195 | NHCO$_2$(CH$_2$)$_4$SOMe | Me | — | |
| 4-196 | NHCO$_2$(CH$_2$)$_4$SOCF$_3$ | Me | — | |
| 4-197 | NHCO$_2$(CH$_2$)$_4$SOPh | Me | — | |
| 4-198 | NHCO$_2$(CH$_2$)$_4$SO$_2$Me | Me | — | |
| 4-199 | NHCO$_2$(CH$_2$)$_4$SO$_2$CF$_3$ | Me | — | |
| 4-200 | NHCO$_2$(CH$_2$)$_4$SO$_2$Ph | Me | — | |
| 4-201 | NHCO$_2$Ph | Me | — | |
| 4-202 | NHCO$_2$C$_6$H$_4$OMe-4 | Me | — | |
| 4-203 | NHCONHMe | Me | — | |
| 4-204 | NHCONHC$_2$H$_5$ | Me | — | |
| 4-205 | NHCONHPr-n | Me | — | |
| 4-206 | NHCONHBu-t | Me | — | |
| 4-207 | NHCONHBu-s | Me | — | |
| 4-208 | NHCONH(Hex-n) | Me | — | |
| 4-209 | H | Cl | — | |
| 4-210 | NH$_2$ | Cl | — | |
| 4-211 | NHCHO | Cl | — | |

TABLE 4-continued

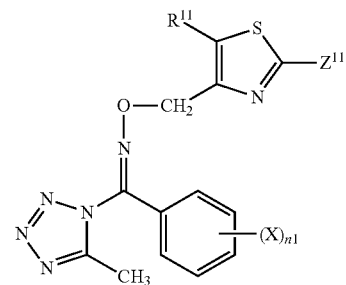

| No | $Z^{11}$ | $R^{11}$ | $(X)_{n1}$ | mp °C. |
|---|---|---|---|---|
| 4-212 | NHCOCH$_2$CF$_3$ | Cl | — | |
| 4-213 | NHCOC$_2$F$_5$ | Cl | — | |
| 4-214 | NHCOCH$_2$F | Cl | — | |
| 4-215 | NHCOC(CH$_3$)$_2$CF$_3$ | Cl | — | |
| 4-216 | NHCOCH$_2$CH$_2$CF$_3$ | Cl | — | |
| 4-217 | NHCOCH$_2$C$_2$F$_5$ | Cl | — | |
| 4-218 | NHCOCH$_2$CH=CH$_2$ | Cl | — | |
| 4-219 | NHCOCH$_2$CH=CMe$_2$ | Cl | — | |
| 4-220 | NHCOC(CH$_3$)$_2$CH=CH$_2$ | Cl | — | |
| 4-221 | NHCOC(CH$_3$)$_2$CH=CHCH$_3$ | Cl | — | |
| 4-222 | NHCOCH$_2$CH=CHCl | Cl | — | |
| 4-223 | NHCOCH$_2$CH=CHCF$_3$ | Cl | — | |
| 4-224 | NHCOCH$_2$Cl=Cl$_2$ | Cl | — | |
| 4-225 | NHCO(1,1-dimethyl-2-propynyl) | Cl | — | |
| 4-226 | NHCO(2-butynyl) | Cl | — | |
| 4-227 | NHCO(1,1-dimethyl-2-butynyl) | Cl | — | |
| 4-228 | NHCO(1,1-dimethyl-2-pentynyl) | Cl | — | |
| 4-229 | NHCO(1-propynyl) | Cl | — | |
| 4-230 | NHCO(1,1-dimethyl-3-Iodo-2-pentynyl) | Cl | — | |
| 4-231 | NHCO(4,4,4-trifluoro-2-butynyl) | Cl | — | |
| 4-232 | NHCOPr-c | Cl | — | |
| 4-233 | NHCOHex-c | Cl | — | |
| 4-234 | NHCO(CH$_2$)$_4$CO$_2$H | Cl | — | |
| 4-235 | NHCOCH$_2$CH$_2$NHCO$_2$Bu-t | Cl | — | |
| 4-236 | NHCOCH$_2$CH$_2$NHCO$_2$Et | Cl | — | |
| 4-237 | NHCOCH$_2$CH$_2$NHCOCH$_3$ | Cl | — | |
| 4-238 | NHCOCH$_2$CH$_2$NHMe$_2$ | Cl | — | |
| 4-239 | NHCOCH$_2$CH$_2$N(Me)COCH$_3$ | Cl | — | |
| 4-240 | NHCOCH$_2$NHCOPh | Cl | — | |
| 4-241 | NHCOCH$_2$CH$_2$N(Me)COPh | Cl | — | |
| 4-242 | NHCOCH$_2$CH$_2$NHPh | Cl | — | |
| 4-243 | NHCO(CH$_2$)$_4$NH$_2$ | Cl | — | |
| 4-244 | NHCOCH$_2$NHCH$_2$Ph | Cl | — | |
| 4-245 | NHCOCH$_2$N(CH$_2$Ph)(CO$_2$Bu-t) | Cl | — | |
| 4-246 | NHCOCH$_2$CH$_2$OC$_6$H$_4$Cl-4 | Cl | — | |
| 4-247 | NHCOCH$_2$OPh | Cl | — | |
| 4-248 | NHCOCH$_2$OC$_6$H$_4$F-3 | Cl | — | |
| 4-249 | NHCOCH$_2$OC$_6$H$_4$OCF$_3$-3 | Cl | — | |
| 4-250 | NHCO(CH$_2$)$_4$SMe | Cl | — | |
| 4-251 | NHCOCH$_2$CH$_2$OEt | Cl | — | |
| 4-252 | NHCOCH$_2$OPr-i | Cl | — | |
| 4-253 | NHCOCH$_2$OBu-i | Cl | — | |
| 4-254 | NHCOCH$_2$CH$_2$OCH$_2$CH$_2$OMe | Cl | — | |
| 4-255 | NHCO$_2$CH$_3$ | Cl | — | |
| 4-256 | NHCO$_2$C$_2$H$_5$ | Cl | — | |
| 4-257 | NHCO$_2$Pr-n | Cl | — | |
| 4-258 | NHCO$_2$Pr-i | Cl | — | |
| 4-259 | NHCO$_2$Bu-n | Cl | — | |
| 4-260 | NHCO$_2$Bu-i | Cl | — | |
| 4-261 | NHCO$_2$Bu-s | Cl | — | |
| 4-262 | NHCO$_2$Bu-t | Cl | — | |
| 4-263 | NHCO$_2$Bu-t | Br | — | |
| 4-264 | NHCO$_2$Bu-t | Cl | 2-Cl | |
| 4-265 | NHCO$_2$Bu-t | Cl | 3-Cl | |
| 4-266 | NHCO$_2$Bu-t | Cl | 4-Cl | |
| 4-267 | NHCO$_2$Bu-t | Cl | 2,4-Cl$_2$ | |

TABLE 4-continued

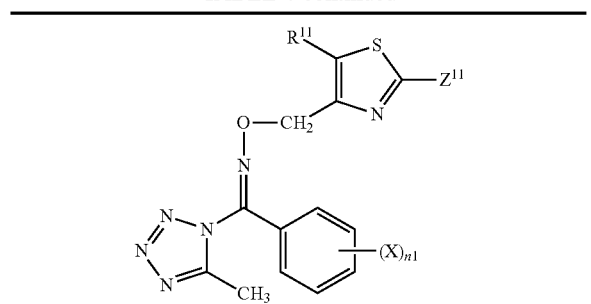

| No | $Z^{11}$ | $R^{11}$ | $(X)_{n1}$ | mp °C. |
|---|---|---|---|---|
| 4-268 | NHCO$_2$Bu-t | Cl | 3,5-Cl$_2$ | |
| 4-269 | NHCO$_2$Bu-t | Cl | 3,4,5-Cl$_3$ | |
| 4-270 | NHCO$_2$Bu-t | Cl | 2-Me | |
| 4-271 | NHCO$_2$CH$_2$CF$_3$ | Cl | — | |
| 4-272 | NHCO$_2$C$_2$F$_5$ | Cl | — | |
| 4-273 | NHCO$_2$CH$_2$CH$_2$F | Cl | — | |
| 4-274 | NHCO$_2$C(CH$_3$)$_2$CF$_3$ | Cl | — | |
| 4-275 | NHCO$_2$CH$_2$C$_2$F$_3$ | Cl | — | |
| 4-276 | NHCO$_2$CH$_2$C$_2$F$_5$ | Cl | — | |
| 4-277 | NHCO$_2$CH$_2$CH=CH$_2$ | Cl | — | |
| 4-278 | NHCO$_2$CH$_2$CH=CMe$_2$ | Cl | — | |
| 4-279 | NHCO$_2$C(CH$_3$)$_2$CH=CH$_2$ | Cl | — | |
| 4-280 | NHCO$_2$C(CH$_3$)$_2$CH=CHCH$_3$ | Cl | — | |
| 4-281 | NHCO$_2$CH$_2$CH=CHCl | Cl | — | |
| 4-282 | NHCO$_2$CH$_2$CH=CHCF$_3$ | Cl | — | |
| 4-283 | NHCO$_2$CH$_2$Cl=Cl$_2$ | Cl | — | |
| 4-284 | NHCO$_2$(1,1-dimethyl-2-propynyl) | Cl | — | |
| 4-285 | NHCO$_2$(2-butynyl) | Cl | — | |
| 4-286 | NHCO$_2$(1,1-dimethyl-2-butynyl) | Cl | — | |
| 4-287 | NHCO$_2$(1,1-dimethyl-2-pentynyl) | Cl | — | |
| 4-288 | NHCO$_2$(1-propynyl) | Cl | — | |
| 4-289 | NHCO$_2$(1,1-dimethyl-3-Iodo-2-pentynyl) | Cl | — | |
| 4-290 | NHCO$_2$(4,4,4-trifluoro-2-butynyl) | Cl | — | |
| 4-291 | NHCO$_2$Pr-c | Cl | — | |
| 4-292 | NHCO$_2$Hex-c | Cl | — | |
| 4-293 | NHCO$_2$CH$_2$CH$_2$NHCO$_2$Bu-t | Cl | — | |
| 4-294 | NHCO$_2$CH$_2$CH$_2$NHCO$_2$Et | Cl | — | |
| 4-295 | NHCO$_2$CH$_2$CH$_2$CH$_2$NHCOCH$_3$ | Cl | — | |
| 4-296 | NHCO$_2$CH$_2$CH$_2$CH$_2$NMe$_2$ | Cl | — | |
| 4-297 | NHCO$_2$CH$_2$CH$_2$N(Me)COCH$_3$ | Cl | — | |
| 4-298 | NHCO$_2$CH$_2$CH$_2$NHCOPh | Cl | — | |
| 4-299 | NHCO$_2$CH$_2$CH$_2$N(Me)COPh | Cl | — | |
| 4-300 | NHCO$_2$CH$_2$CH$_2$NHPh | Cl | — | |
| 4-301 | NHCO$_2$(CH$_2$)$_4$NH$_2$ | Cl | — | |
| 4-302 | NHCO$_2$CH$_2$NHCH$_2$Ph | Cl | — | |
| 4-303 | NHCO$_2$CH$_2$N(CH$_2$Ph)(CO$_2$Bu-t) | Cl | — | |
| 4-304 | NHCO$_2$CH$_2$C$_3$H$_5$-c | Cl | — | |
| 4-305 | NHCO$_2$CH(CH$_3$)C$_3$H$_5$-c | Cl | — | |
| 4-306 | NHCO$_2$CH$_2$C$_6$H$_{11}$-c | Cl | — | |
| 4-307 | NHCO$_2$CH$_2$Ph | Cl | — | |
| 4-308 | NHCO$_2$CH(CH$_3$)CH$_2$Ph | Cl | — | |
| 4-309 | NHCO$_2$CH(CH$_3$)Ph | Cl | — | |
| 4-310 | NHCO$_2$C(CH$_3$)$_2$Ph | Cl | — | |
| 4-311 | NHCO$_2$CH$_2$C$_6$H$_4$CF$_3$-4 | Cl | — | |
| 4-312 | NHCO$_2$CH$_2$C$_6$H$_4$CN-4 | Cl | — | |
| 4-313 | NHCO$_2$CH$_2$C$_6$H$_4$CN-3 | Cl | — | |
| 4-314 | NHCO$_2$CH$_2$C$_6$H$_4$Cl-4 | Cl | — | |
| 4-315 | NHCO$_2$CH$_2$C$_6$H$_4$Cl-3 | Cl | — | |
| 4-316 | NHCO$_2$CH$_2$C$_6$H$_4$OMe-3 | Cl | — | |
| 4-317 | NHCO$_2$CH$_2$C$_6$H$_4$OMe-2 | Cl | — | |
| 4-318 | NHCO$_2$CH$_2$C$_6$H$_4$Me-4 | Cl | — | |
| 4-319 | NHCO$_2$CH$_2$C$_6$H$_4$Me-3 | Cl | — | |
| 4-320 | NHCO$_2$CH$_2$C$_6$H$_4$Me-2 | Cl | — | |
| 4-321 | NHCO$_2$CH$_2$C$_6$H$_4$SO$_2$Me-4 | Cl | — | |
| 4-322 | NHCO$_2$CH$_2$C$_6$H$_4$SO$_2$Me-3 | Cl | — | |
| 4-323 | NHCO$_2$CH$_2$C$_6$H$_4$Ph-4 | Cl | — | |
| 4-324 | NHCO$_2$CH$_2$C$_6$H$_4$Ph-3 | Cl | — | |
| 4-325 | NHCO$_2$CH$_2$Py-2 | Cl | — | |
| 4-326 | NHCO$_2$CH$_2$(6-Me-2-Py) | Cl | — | |
| 4-327 | NHCO$_2$C(CH$_3$)$_2$Py-4 | Cl | — | |
| 4-328 | NHCO$_2$CH$_2$(2-thiazolyl) | Cl | — | |
| 4-329 | NHCO$_2$CH$_2$(2-benzthiazolyl) | Cl | — | |
| 4-330 | NHCO$_2$CH$_2$CH$_2$OMe | Cl | — | |
| 4-331 | NHCO$_2$CH$_2$CH$_2$OEt | Cl | — | |
| 4-332 | NHCO$_2$CH$_2$CH$_2$OPr-i | Cl | — | |
| 4-333 | NHCO$_2$CH$_2$CH$_2$OBu-i | Cl | — | |
| 4-334 | NHCO$_2$CH$_2$CH$_2$OCH$_2$CH$_2$OMe | Cl | — | |
| 4-335 | NHCO$_2$CH$_2$CH$_2$OC$_6$H$_4$Cl-4 | Cl | — | |
| 4-336 | NHCOCH$_2$OPh | Cl | — | |
| 4-337 | NHCOCH$_2$OC$_6$H$_4$F-3 | Cl | — | |
| 4-338 | NHCOCH$_2$OC$_6$H$_4$OCF$_3$-3 | Cl | — | |
| 4-339 | NHCOCH$_2$CH$_2$OCH$_2$Ph | Cl | — | |
| 4-340 | NHCO$_2$(1,1-dimethyl-3-phenyl-2-pentynyl) | Cl | — | |
| 4-341 | NHCO$_2$CH$_2$CH$_2$OCH$_2$Ph | Cl | — | |
| 4-342 | NHCO$_2$(1,1-dimethyl-3-phenyl-2-pentynyl) | Cl | — | |
| 4-343 | NHCO$_2$(CH$_2$)$_4$SMe | Cl | — | |
| 4-344 | NHCO$_2$(CH$_2$)$_4$SCF$_3$ | Cl | — | |
| 4-345 | NHCO$_2$(CH$_2$)$_4$SPh | Cl | — | |
| 4-346 | NHCO$_2$(CH$_2$)$_4$SOMe | Cl | — | |
| 4-347 | NHCO$_2$(CH$_2$)$_4$SOCF$_3$ | Cl | — | |
| 4-348 | NHCO$_2$(CH$_2$)$_4$SOPh | Cl | — | |
| 4-349 | NHCO$_2$(CH$_2$)$_4$SO$_2$Me | Cl | — | |
| 4-350 | NHCO$_2$(CH$_2$)$_4$SO$_2$CF$_3$ | Cl | — | |
| 4-351 | NHCO$_2$(CH$_2$)$_4$SO$_2$Ph | Cl | — | |
| 4-352 | NHCO$_2$Ph | Cl | — | |
| 4-353 | NHCO$_2$C$_6$H$_4$OMe-4 | Cl | — | |
| 4-354 | NHCONHMe | Cl | — | |
| 4-355 | NHCONHC$_2$H$_5$ | Cl | — | |
| 4-356 | NHCONHPr-n | Cl | — | |
| 4-357 | NHCONHBu-t | Cl | — | |
| 4-358 | NHCONHBu-s | Cl | — | |
| 4-359 | NHCONH(Hex-n) | Cl | — | |
| 4-360 | NHCOCH$_2$CF$_3$ | — | — | |
| 4-361 | NHCOC$_2$F$_5$ | — | — | |
| 4-362 | NHCOCH$_2$CH$_2$F | — | — | |
| 4-363 | NHCOC(CH$_3$)$_2$CF$_3$ | — | — | |
| 4-364 | NHCOCH$_2$C$_2$CF$_3$ | — | — | |
| 4-365 | NHCOCH$_2$C$_2$F$_5$ | — | — | |
| 4-366 | NHCOCH$_2$CH=CH$_2$ | — | — | |
| 4-367 | NHCOCH$_2$CH=CMe$_2$ | — | — | |
| 4-368 | NHCOC(CH$_2$)$_2$CH=CH$_2$ | — | — | |
| 4-369 | NHCOC(CH$_3$)$_2$CH=CHCH$_3$ | — | — | |
| 4-370 | NHCOCH$_2$CH=CHCl | — | — | |
| 4-371 | NHCOCH$_2$CH=CHCF$_3$ | — | — | |
| 4-372 | NHCOCH$_2$Cl=Cl$_2$ | — | — | |
| 4-373 | NHCO(1,1-dimethyl-2-propynyl) | — | — | |
| 4-374 | NHCO(2-butynyl) | — | — | |
| 4-375 | NHCO(1,1-dimethyl-2-butynyl) | — | — | |
| 4-376 | NHCO(1,1-dimethyl-2-pentynyl) | — | — | |
| 4-377 | NHCO(1-propynyl) | — | — | |
| 4-378 | NHCO(1,1-dimethyl-3-Iodo-2-pentynyl) | — | — | |

TABLE 4-continued

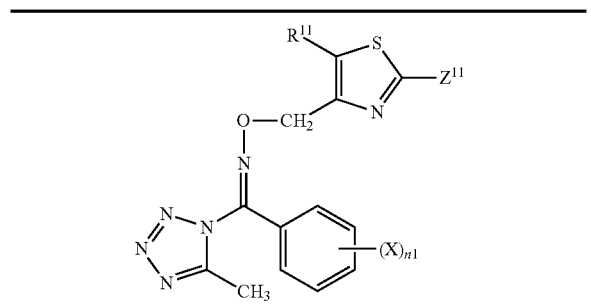

| No | $Z^{11}$ | $R^{11}$ | $(X)_{n1}$ | mp °C. |
|---|---|---|---|---|
| 4-379 | NHCO(4,4,4-trifluoro-2-butynyl) | — | — | |
| 4-380 | $NHCO(CH_2)_4CO_2H$ | — | — | |
| 4-381 | $NHCOCH_2CH_2NHMe_2$ | — | — | |
| 4-382 | $NHCO(CH_2)_4NH_2$ | — | — | |
| 4-383 | $NHCOCH_2NHCH_2Ph$ | — | — | |
| 4-384 | $NHCOCH_2N(CH_2Ph)(CO_2Bu-t)$ | — | — | |
| 4-385 | $NHCOCH_2CH_2NMe_2$ | — | — | |
| 4-386 | $NHCOCH_2CH_2NHEt$ | — | — | |
| 4-387 | $NHCOCH_2CH_2NHPr-n$ | — | — | |
| 4-388 | $NHCOCH_2CH_2OC_6H_4Cl-4$ | — | — | |
| 4-389 | $NHCOCH_2OPh$ | — | — | |
| 4-390 | $NHCOCH_2OC_6H_4F-3$ | — | — | |
| 4-391 | $NHCOCH_2OC_6H_4OCF_3-3$ | — | — | |
| 4-392 | $NHCOCH2OC_6H_4CN-2$ | — | — | |
| 4-393 | $NHCOCH2OC_6H_4F-4$ | — | — | |
| 4-394 | $NHCOCH_2OC_6H_3(3,4-methylenedioxy)$ | — | — | |
| 4-395 | $NHCOCH_2OC_6H_4(CONH_2)-2$ | — | — | |
| 4-396 | $NHCOCH_2OC_6H_3(3,4-(OCH_3)_2)$ | — | — | |
| 4-397 | $NHCOCH_2O(6-CF_3-pyrimidin-4-yl)$ | — | — | |
| 4-398 | $NHCOCH_2O(3-Py)$ | — | — | |
| 4-399 | $NHCOCH_2CH_2CH_2COCH_3$ | — | — | |
| 4-400 | $NHCO_2CH_2CF_3$ | — | — | |
| 4-401 | $NHCO_2C_2F_5$ | — | — | |
| 4-402 | $NHCO_2CH_2CH_2F$ | — | — | |
| 4-403 | $NHCO_2C(CH_3)_2CF_3$ | — | — | |
| 4-404 | $NHCO_2CH_2CH_2CF_3$ | — | — | |
| 4-405 | $NHCO_2CH_2C_2F_5$ | — | — | |
| 4-406 | $NHCO_2CH_2CH=CH_2$ | — | — | |
| 4-407 | $NHCO_2CH_2CH=CMe_2$ | — | — | |
| 4-408 | $NHCO_2C(CH_3)_2CH=CH_2$ | — | — | |
| 4-409 | $NHCO_2C(CH_3)_2CH=CHCH_3$ | — | — | |
| 4-410 | $NHCO_2CH_2CH=CHCl$ | — | — | |
| 4-411 | $NHCO_2CH_2CH=CHCF_3$ | — | — | |
| 4-412 | $NHCO_2CH_2Cl=Cl_2$ | — | — | |
| 4-413 | $NHCO_2(1,1\text{-dimethyl-2-propynyl})$ | — | — | |
| 4-414 | $NHCO_2(2\text{-butynyl})$ | — | — | |
| 4-415 | $NHCO_2(1,1\text{-dimethyl-2-butynyl})$ | — | — | |
| 4-416 | $NHCO_2(1,1\text{-dimethyl-2-pentynyl})$ | — | — | |
| 4-417 | $NHCO_2(1\text{-propynyl})$ | — | — | |
| 4-418 | $NHCO_2(1,1\text{-dimethyl-3-Iodo-2-pentynyl})$ | — | — | |
| 4-419 | $NHCO_2(4,4,4\text{-trifluoro-2-butynyl})$ | — | — | |
| 4-420 | $NHCO_2(1,1\text{-dimethyl-3-phenyl-2-pentynyl})$ | — | — | |
| 4-421 | $NHCO_2CH_2CH_2NHCO_2Bu-t$ | — | — | |
| 4-422 | $NHCO_2CH_2CH_2NHCO_2Et$ | — | — | |
| 4-423 | $NHCO_2CH_2N(CH_2Ph)(CO_2Bu-t)$ | — | — | |
| 4-424 | $NHCO_2CH_2NCH_2Ph$ | — | — | |
| 4-425 | $NHCO_2CH_2CH_2NCH_2Ph$ | — | — | |
| 4-426 | $NHCO_2CH_2CH_2NCH_2C_6H_4Cl-4$ | — | — | |
| 4-427 | $NHCO_2CH_2CH_2NHMe$ | — | — | |
| 4-428 | $NHCO_2CH_2C(CH_3)_2N(CH_3)_2$ | — | — | |
| 4-429 | $NHCO_2CH(CH_3)CH_2N(CH_3)_2$ | — | — | |
| 4-430 | $NHCO_2CH_2C_3H_5\text{-c}$ | — | — | |
| 4-431 | $NHCO_2CH(CH_3)C_3H_5\text{-c}$ | — | — | |
| 4-432 | $NHCO_2CH_2C_6H_{11}\text{-c}$ | — | — | |
| 4-433 | $NHCO_2CH(CH_3)CH_2Ph$ | — | — | |
| 4-434 | $NHCO_2CH(CH_3)Ph$ | — | — | |
| 4-435 | $NHCO_2C(CH_3)_2Ph$ | — | — | |
| 4-436 | $NHCO_2CH_2C_6H_4CF_3-4$ | — | — | |
| 4-437 | $NHCO_2CH_2C_6H_4CN-4$ | — | — | |
| 4-438 | $NHCO_2CH_2C_6H_4CN-3$ | — | — | |
| 4-439 | $NHCO_2CH_2C_6H_4Cl-4$ | — | — | |
| 4-440 | $NHCO_2CH_2C_6H_4Cl-3$ | — | — | |
| 4-441 | $NHCO_2CH_2C_6H_4OMe-3$ | — | — | |
| 4-442 | $NHCO_2CH_2C_6H_4OMe-2$ | — | — | |
| 4-443 | $NHCO_2CH_2C_6H_4Me-4$ | — | — | |
| 4-444 | $NHCO_2CH_2C_6H_4Me-3$ | — | — | |
| 4-445 | $NHCO_2CH_2C_6H_4Me-2$ | — | — | |
| 4-446 | $NHCO_2CH_2C_6H_4SO_2Me-4$ | — | — | |
| 4-447 | $NHCO_2CH_2C_6H_4SO_2Me-3$ | — | — | |
| 4-448 | $NHCO_2CH_2C_6H_4Ph-4$ | — | — | |
| 4-449 | $NHCO_2CH_2C_6H_4Ph-3$ | — | — | |
| 4-450 | $NHCO_2CH_2C_6H_4OCH_3-4$ | — | — | |
| 4-451 | $NHCO_2CH_2C_6H_3(3,4\text{-methylenedioxy})$ | — | — | |
| 4-452 | $NHCO_2CH_2Py-2$ | — | — | |
| 4-453 | $NHCO_2CH_2(6\text{-Me-2-Py})$ | — | — | |
| 4-454 | $NHCO_2C(CH_3)_2Py-4$ | — | — | |
| 4-455 | $NHCO_2CH_2(2\text{-thiazolyl})$ | — | — | |
| 4-456 | $NHCO_2CH_2(2\text{-benzthiazolyl})$ | — | — | |
| 4-457 | $NHCO_2CH_2(3\text{-Py})$ | — | — | |
| 4-458 | $NHCO_2CH_2(4\text{-Py})$ | — | — | |
| 4-459 | $NHCO_2CH(CH_3)(4\text{-Py})$ | — | — | |
| 4-460 | $NHCO_2CH_2CH_2OMe$ | — | — | |
| 4-461 | $NHCO_2CH_2CH_2OEt$ | — | — | |
| 4-462 | $NHCO_2CH_2CH_2OPr-i$ | — | — | |
| 4-463 | $NHCO_2CH_2CH_2OBu-i$ | — | — | |
| 4-464 | $NHCO_2CH_2CH_2OCH_2CH_2OMe$ | — | — | |
| 4-465 | $NHCO_2C(CH_3)_2CH_2OCH_3$ | — | — | |
| 4-466 | $NHCO_2CH(CH_3)CH_2OCH_3$ | — | — | |
| 4-467 | $NHCO_2CH_2CH_2OC_6H_4Cl-4$ | — | — | |
| 4-468 | $NHCO_2CH_2OPh$ | — | — | |
| 4-469 | $NHCO_2CH_2OC_6H_4F-3$ | — | — | |
| 4-470 | $NHCO_2CH_2OC_6H_4OCF_3-3$ | — | — | |
| 4-471 | $NHCO_2CH_2CH_2OCH_2Ph$ | — | — | |
| 4-472 | $NHCO_2CH_2CH_2OCH_2CH_2Ph$ | — | — | |
| 4-473 | $NHCO_2(CH_2)_4SMe$ | — | — | |
| 4-474 | $NHCO_2(CH_2)_4SCF_3$ | — | — | |
| 4-475 | $NHCO_2(CH_2)_4SPh$ | — | — | |
| 4-476 | $NHCO_2(CH_2)_4SOMe$ | — | — | |
| 4-477 | $NHCO_2(CH_2)_4SOCF_3$ | — | — | |
| 4-478 | $NHCO_2(CH_2)_4SOPh$ | — | — | |
| 4-479 | $NHCO_2(CH_2)_4SO_2Me$ | — | — | |
| 4-480 | $NHCO_2(CH_2)_4SO_2CF_3$ | — | — | |
| 4-481 | $NHCO_2(CH_2)_4SO_2Ph$ | — | — | |
| 4-482 | $NHCO_2Ph$ | — | — | |
| 4-483 | $NHCO_2C_6H_4OMe-4$ | — | — | |

Among the compounds shown in Tables 1 to 4, the spectral data ($^1$H-NMR (300 MHz, CDCl$_3$)) of some compounds are as shown in Table 5.

TABLE 5

| No | NMR Data |
|---|---|
| 1-3 | 1.24 (s, 9H), 4.01 (s, 3H), 4.37 (br-s, 2H), 5.21 (s, 2H), 6.41 (d, 1H, J = 1.1 Hz), 6.63 (d, 1H, J = 1.1 Hz), 7.34-7.44 (m, 3H), 7.53-7.56 (m, 2H). |
| 1-4 | 1.38 (t, 3H, J = 7.0 Hz), 3.97-4.04 (m, 2H), 4.01 (s, 3H), 4.35 (br-s, 2H), 5.16 (s, 2H), 5.88 (d, 1H, J = 2.0 Hz), 6.20 (d, 1H, J = 2.0 Hz), 7.35-7.44 (m, 3H), 7.52-7.55 (m, 2H). |
| 1-5 | 2.19 (s, 3H), 3.96 (s, 3H), 4.29 (br-s, 2H), 5.27 (s, 2H), 6.42 (d, 1H, J = 8.2 Hz), 7.23-7.26 (m, 1H), 7.34-7.46 (m, 3H), 7.51-7.54 (m, 2H). |
| 1-6 | 3.77 (s, 3H), 4.00 (s, 3H), 4.40 (br-s, 2H), 5.16 (s, 2H), 5.89 (s, 1H), 6.21 (s, 1H), 7.34-7.54 (m, 5H) |
| 1-7 | 1.19 (t, 3H), 2.52 (q, 2H), 4.00 (s, 3H), 4.45 (br-s, 2H), 5.19 (s, 2H), 6.29 (s, 1H), 6.47 (s, 1H), 7.34-7.55 (m, 5H) |
| 1-17 | 1.33 (s, 9H), 3.85 (s, 3H), 3.99 (s, 3H), 5.20 (s, 2H), 6.54 (d, 1H, J = 2.1 Hz), 7.34-7.53 (m, 5H), 7.82 (d, 1H, J = 2.1 Hz), 7.95 (br-s, 1H). |
| 1-71 | 1.52 (s, 9H), 2.33 (s, 3H), 3.97 (s, 3H), 5.21 (s, 2H), 6.75 (s, 1H), 7.13 (br-s, 1H), 7.34-7.54 (m, 5H), 7.71 (s, 1H). |
| 1-73 | 1.53 (s, 9H), 3.98 (s, 3H), 5.24 (s, 2H), 5.48 (d, 1H, J = 11.1 Hz), 5.99 (d, 1H, J = 17.7 Hz), 6.65 (dd, 1H, J = 17.7, 11.1 Hz), 6.95 (s, 1H), 7.20 (br-s, 1H), 7.35-7.53 (m, 5H), 7.88 (s, 1H). |
| 1-76 | 1.22 (t, 3H, J = 7.0 Hz), 1.51 (s, 9H), 3.58 (q, 2H, J = 7.0 Hz), 3.78 (t, 2H, J = 4.7 Hz), 3.98 (s, 3H), 4.18 (t, 2H, J = 4.7 Hz), 5.17 (s, 2H), 6.52 (d, 1H, J = 2.2 Hz), 7.25 (br-s, 1H), 7.34-7.53 (m, 6H). |
| 1-77 | 1.31 (d, 6H, J = 7.8 Hz), 1.51 (s, 9H), 3.98 (s, 3H), 4.66 (hept, 1H, J = 7.8 Hz), 5.17 (s, 2H), 6.42 (d, 1H, J = 1.8 Hz), 7.22 (br-s, 1H), 7.34-7.53 (m, 6H). |
| 1-78 | 0.96 (t, 3H, J = 7.2 Hz), 1.41-1.48 (m, 2H), 1.52 (s, 9H), 1.71-1.80 (m, 2H), 3.98 (s, 3H), 4.03 (t, 2H, J = 6.6 Hz), 5.19 (s, 2H), 6.47 (d, 1H, J = 1.8 Hz), 7.34-7.62 (m, 7H). |
| 1-82 | 1.51(s, 9H), 3.00(s, 6H), 3.98(s, 3H), 5.16(s, 2H), 6.15(d, 1H), 7.02(brs, 1H), 7.11(d, 1H), 7.37-7.44(m, 3H), 7.52-7.55(m, 2H) |
| 1-83 | 1.49 (s, 9H), 1.52 (s, 9H), 3.30 (s, 3H), 4.01 (s, 3H), 5.21 (s, 2H), 7.12 (d, 1H, J = 1.9 Hz), 7.14 (br-s, 1H), 7.35-7.55 (m, 5H), 7.80 (d, 1H, J = 1.9 Hz). |
| 1-86 | 1.51 (s, 9H), 3.31 (t, 4H, J = 4.9 Hz), 3.81 (t, 4H, J = 4.9 Hz), 3.99 (s, 3H), 5.17 (s, 2H), 6.30 (d, 1H, J = 2.2 Hz), 7.16 (br-s, 1H), 7.32-7.65 (m, 6H). |
| 1-89 | 1.53 (s, 9H), 3.87 (s, 3H), 4.03 (s, 3H), 5.70 (s, 2H), 7.34-7.55 (m, 5H), 7.77 (br-s, 1H), 7.93 (d, 1H), 8.21 (d, 1H). |
| 1-90 | 1.54 (s, 9H), 3.99 (s, 3H), 5.28 (s, 2H), 7.15 (s, 1H), 7.35-7.51 (m, 6H), 8.18 (s, 1H). |
| 1-131 | 0.95(t, 3H, J = 7.3 Hz), 1.37-1.44(m, 2H), 1.60-1.70(m, 2H), 3.99(s, 3H), 4.16(t, 2H, J = 6.7 Hz), 4.25(br-s, 2H), 5.14(s, 2H), 6.18(d, 1H, J = 2.0 Hz), 7.16(d, 1H, J = 2.0 Hz), 7.35-7.47(m, 3H), 7.51-7.54(m, 2H) |
| 1-132 | 0.95(t, 3H, J = 7.4 Hz), 1.41(tq, 2H, J = 7.6, 7.4 Hz), 1.51 or 1.55(s, 9H), 1.66(tt, 2H, J = 7.6, 6.7 Hz), 4.03(s, 3H), 4.18(t, 2H, J = 6.7 Hz), 5.20(s, 2H), 6.72(br-s, 1H), 7.20(br-s, 1H), 7.35-7.54(m, 5H), 7.78(d, 1H, J = 1.8 Hz) |
| 1-197 | 1.23 (t, 3H), 1.24 (d, 6H), 2.90 (septet, 1H), 3.55 (q, 2H), 3.69(t, 2H), 3.99 (s, 3H), 4.34 (t, 2H), 5.23 (s, 2H), 6.82 (s, 1H), 7.35-7.54 (m, 6H), 7.79 (s, 1H). |
| 1-275 | 1.52(s, 9H), 3.99(s, 3H), 5.20(s, 2H), 6.94(d, 1H, J = 1.6 Hz), 7.20(br-s, 1H), 7.35-7.52(m, 5H), 7.96(d, 1H, J = 1.5 Hz) |
| 1-278 | 1.53 (s, 9H), 3.99 (s, 3H), 5.19 (s, 2H), 7.09 (s, 1H), 7.15 (br-s, 1H), 7.36-7.51 (m, 5H), 8.13 (s, 1H) |
| 1-377 | 4.00 (s, 3H), 5.31 (s, 2H), 7.15 (d, 1H), 7.36-7.51 (m, 6H), 7.80 (dd, 1H), 8.12 (d, 1H), 8.65 (br-s, 1H). |
| 1-398 | in CD$_3$OD 1.34-1.70 (m, 6H), 2.37 (t, 2H), 2.84 (t, 2H), 3.92 (s, 3H), 4.59 (br-s, 2H), 5.21 (s, 2H), 7.02 (d, 1H), 7.29-7.67 (m, 6H), 7.70 (t, 1H), 7.93 (d, 1H) |
| 1-399 | 2.13 (br-s, 1H), 3.45 (s, 2H), 3.87 (s, 2H), 3.97 (s, 3H), 5.30 (s, 2H), 7.02 (d, 1H), 7.23-7.54 (m, 10H), 7.70 (t, 1H), 8.17 (d, 1H), 9.69 (br-s, 1H) |
| 1-400 | 1.47 (s, 9H), 3.98 (s, 3H), 4.52 (d, 2H), 4.58 (s, 2H), 5.27 (s, 2H), 7.02 (d, 1H), 7.26-7.52 (m, 11H), 7.71 (t, 1H), 8.14 (d, 1H) |
| 1-405 | 3.95 (s, 3H), 4.64 (s, 3H), 5.30 (s, 3H), 7.01 (d, 1H), 7.02-7.08 (m, 2H), 7.32-7.53 (m, 8H), 7.74 (t, 1H), 8.22 (d, 1H), 8.87 (br-s, 1H). |
| 1-411 | 4.03 (s, 3H), 4.75 (s, 2H), 5.31 (s, 2H), 7.01 (d, 1H), 7.07 (d, 1H), 7.16 (t, 1H), 7.37-7.67 (m, 7H), 7.34 (t, 1H), 8.17 (d, 1H), 8.86 (s, 1H). |
| 1-415 | 3.99 (s, 3H), 4.58 (q, 2H, JC-F = 8.3 Hz), 5.72 (s, 2H), 7.01 (d, 1H, J = 7.7 Hz), 7.35-7.52 (m, 6H), 7.72 (dd, 1H, J = 8.1, 7.7 Hz), 7.86 (d, 1H, J = 8.1 Hz). |
| 1-418 | 1.76 (s, 6H), 3.98 (s, 3H), 5.26 (s, 2H), 6.97 (d, 1H), 7.34-7.52 (m, 6H), 7.68 (t, 1H), 7.80 (d, 1H) |
| 1-420 | 3.99 (s, 3H), 4.66 (t, 2H), 5.27 (s, 2H), 7.01 (d, 1H), 7.33-3.54 (m, 6H), 7.73 (dd, 1H), 7.86 (d, 1H). |
| 1-421 | 3.98 (s, 3H), 4.69 (d, 2H, J = 5.7 Hz), 5.26 (s, 2H), 5.27 (d, 1H, J = 10.8 Hz), 5.37 (d, 1H, J = 17.3 Hz), 5.97 (ddt, 1H, 17.3, 10.8, 5.7 Hz), 6.96 (d, 1H, J = 7.5 Hz), 7.31-7.52 (m, 6H), 7.68 (dd, 1H, J = 8.2, 7.5 Hz), 7.89 (d, 1H, 8.2 Hz). |

TABLE 5-continued

| No | NMR Data |
|---|---|
| 1-422 | 1.75 (s, 3H), 1.78 (s, 3H), 3.98 (s, 3H), 4.68 (d, 2H, J = 7.4 Hz), 5.25 (s, 2H), 5.40 (tdd, 1H, J = 7.4, 1.4, 1.3 Hz), 6.95 (d, 1H, J = 7.6 Hz), 7.24 (br, 1H) , 7.34-7.53 (m, 5H), 7.67 (dd, 1H, J = 8.4, 7.6 Hz), 7.90 (d, 1H, 8.4 Hz). |
| 1-423 | 1.59 (s, 6H), 3.97 (s, 3H), 5.13 (d, 1H), 5.23 (d, 1H), 5.25 (s, 2H), 6.15 (dd, 1H), 6.93 (d, 1H), 7.34-7.52 (m, 6H), 7.64 (t, 1H), 7.86 (d, 1H) |
| 1-424 | 1.33 (d, 3H), 1.74 (d, 6H), 3.97 (s, 3H), 5.18-5.31 (m, 1H), 5.24 (s, 2H), 5.58-5.63 (m, 1H), 6.93 (d, 1H), 7.19 (br-s, 1H), 7.35-7.55 (m, 5H), 7.66 (t, 1H), 7.89 (d, 1H) |
| 1-428 | 1.75 (s, 6H), 2.59 (s, 3H), 3.97 (s, 3H), 5.25 (s, 2H), 6.95 (d, 1H), 7.34-7.52 (m, 6H), 7.64 (t, 1H), 7.93 (d, 1H). |
| 1-430 | 1.71 (s, 6H), 1.86 (s, 3H), 3.97 (s, 3H), 5.25 (s, 2H), 6.94 (d, 1H), 7.34-7.52 (m, 6H), 7.66 (t, 1H), 7.92 (d, 1H) |
| 1-431 | 1.13 (t, 3H), 1.72 (s, 6H), 2.23 (q, 2H), 4.00 (s, 3H), 5.24 (s, 2H), 6.93 (d, 1H), 7.21 (br-s, 1H), 7.34 (m, 5H), 7.66 (t, 1H), 7.92 (d, 1H) |
| 1-435 | 1.84 (s, 6H), 3.97 (s, 3H), 5.25 (s, 2H), 6.94 (d, 1H, J = 7.8 Hz), 7.24-7.52 (m, 11H), 7.66 (dd, 1H, J = 8.1, 7.8 Hz), 7.92 (d, 1H, J = 8.1 Hz). |
| 1-437 | 1.15 (t, 3H), 2.22 (q, 2H), 3.59 (q, 2H), 3.98 (s, 3H), 4.30 (t, 2H), 5.26 (s, 2H), 5.96 (br-s, 1H), 6.98 (d, 1H), 7.35-7.52 (m, 6H), 7.69 (t, 1H), 7.87 (d, 1H). |
| 1-443 | 1.10 (s, 6H), 2.32 (s, 6H), 3.98 (s, 3H), 4.10 (s, 2H), 5.25 (s, 2H), 6.95 (d, 1H), 7.34-7.53 (m, 6H), 7.68 (t, 1H), 7.89 (d, 1H) |
| 1-444 | 1.30 (d, 3H), 2.29 (s, 6H), 2.60 (dd, 1H), 3.98 (s, 3H), 5.05 (tq, 1H), 5.25 (s, 2H), 6.94 (d, 1H), 7.34-7.52 (m, 6H), 7.66 (t, 1H), 7.88 (d, 1H) |
| 1-445 | 0.30-0.35 (m, 2H), 0.57-0.63 (m, 2H), 1.14-1.24 (m, 1H), 3.98 (s, 3H), 4.02 (d, 2H, J = 7.3 Hz), 5.26 (s, 2H), 6.96 (d, 1H, J = 7.1 Hz), 7.28 (br, 1H), 7.35-7.53 (m, 5H), 7.68 (dd, 1H, J = 8.2, 7.1 Hz), 7.89 (d, 1H, J = 8.2 Hz). |
| 1-446 | 0.27-0.32 (m, 1H), 0.43-0.59 (m, 3H), 1.01-1.04 (m, 1H), 1.36 (d, 3H), 3.98 (s, 3H), 4.33 (q, 1H), 5.26 (s, 2H), 6.94 (d, 1H), 7.32-7.52 (m, 6H), 7.67 (t, 1H), 7.88 (d, 1H) |
| 1-448 | 1.30 (d, 3H), 2.82 (dd, 1H), 2.30 (dd, 1H), 3.97 (s, 3H), 5.13 (q, 1H), 5.25 (s, 2H), 6.94 (d, 1H), 7.21-7.52 (m, 11H), 7.66 (t, 1H), 7.86 (d, 1H) |
| 1-449 | 1.61 (d, 3H), 3.97 (s, 3H), 5.24 (s, 2H), 5.89 (q, 1H), 6.94 (d, 1H), 7.31-7.52 (m, 11H), 7.65 (t, 1H), 7.87 (d, 1H) |
| 1-450 | 2.04 (s, 6H), 3.97 (s, 3H), 5.25 (s, 2H), 6.91 (d, 1H), 7.23-7.52 (m, 11H), 7.58 (t, 1H), 7.77 (d, 1H) |
| 1-451 | 3.97 (s, 3H), 5.25 (s, 2H), 5.27 (s, 2H), 6.97 (d, 1H), 7.34-7.71 (m, 11H), 7.88 (d, 1H) |
| 1-456 | 3.81 (s, 3H), 3.97 (s, 3H), 5.19 (s, 2H), 5.24 (s, 2H), 6.86-6.98 (m, 4H), 7.35-7.52 (m, 7H), 7.68 (m, 1H), 7.90 (d, 1H, J = 8.1 Hz). |
| 1-457 | 3.86 (s, 3H), 3.97 (s, 3H), 5.24 (s, 2H), 5.28 (s, 2H), 6.89-6.98 (m, 3H), 7.30-7.52 (m, 8H), 7.67 (m, 1H), 7.92 (d, 1H, J = 8.4 Hz). |
| 1-465 | 3.81 (s, 3H), 3.96 (s, 3H), 5.15 (s, 2H), 5.24 (s, 2H), 6.90 (m, 2H), 6.94 (d, 1H, J = 7.2 Hz), 7.32-7.51 (m, 8H), 7.67 (m, 1H), 7.90 (d, 2H, J = 8.1 Hz). |
| 1-466 | 3.97 (s, 3H), 5.11 (s, 2H), 5.24 (s, 2H), 5.97 (s, 2H), 6.78-6.96 (m, 4H), 7.34-7.52 (m, 6H), 7.68 (t, 1H), 7.90 (d, 1H) |
| 1-467 | 3.98 (s, 3H), 5.26 (s, 2H), 5.34 (s, 2H), 6.97 (d, 1H), 7.23-7.75 (m, 10H), 7.91 (d, 1H), 8.61 (d, 1H) |
| 1-470 | 3.98 (s, 3H), 5.26 (s, 2H), 5.52 (s, 2H), 6.99 (d, 1H), 7.34-7.52 (m, 7H), 7.70 (t, 1H), 7.82 (br-s, 1H), 7.92 (d, 1H) |
| 1-471 | 3.99 (s, 3H), 5.27 (s, 2H), 5.61 (s, 2H), 6.99 (d, 1H), 7.34-7.68 (m, 9H), 7.74 (dd, 1H), 7.91-7.93 (m, 1H), 8.05 (d, 1H). |
| 1-474 | 1.60 (d, 3H), 3.98 (s, 3H), 5.26 (s, 2H), 6.97 (d, 1H), 7.28-7.51 (m, 8H), 7.67 (t, 1H), 7.84 (d, 1H), 8.60 (d, 2H) |
| 1-477 | 1.19 (d, 6H, J = 5.9 Hz), 3.59-3.69 (m, 3H), 3.98 (s, 3H), 4.32 (t, 2H, J = 4.8 Hz), 5.26 (s, 2H), 6.96 (d, 1H, J = 7.6 Hz), 7.34-7.53 (m, 6H), 7.68 (dd, 1H, J = 8.1, 7.6 Hz), 7.89 (d, 1H, J = 8.1 Hz). |
| 1-480 | 1.52 (s, 6H), 3.41 (s, 3H), 3.56 (s, 2H), 3.97 (s, 3H), 5.25 (s, 2H), 6.93 (d, 1H), 7.35-7.53 (m, 6H), 7.65 (t, 1H), 7.85 (d, 1H). |
| 1-481 | 1.31 (d, 3H), 3.39 (s, 3H), 3.47 (d, 2H), 3.98 (s, 3H), 5.09 (tq, 1H), 5.25 (s, 2H), 6.95 (d, 1H), 7.34-7.52 (m, 6H), 7.67 (t, 1H), 7.89 (d, 1H) |
| 1-482 | 3.98 (s, 3H), 4.19 (t, 2H, J = 4.7 Hz), 4.53 (t, 2H, J = 4.7 Hz), 5.25 (s, 2H), 6.85 (d, 2H, J = 9.0 Hz), 6.97 (d, 1H, J = 7.5 Hz), 7.24 (d, 2H, J = 9.0 Hz), 7.34-7.52 (m, 6H), 7.69 (dd, 1H, J = 8.6, 7.5 Hz), 7.88 (d, 1H, 8.6 Hz). |
| 1-486 | 3.73 (t, 2H, J = 4.8 Hz), 3.98 (s, 3H), 4.37 (t, 2H, J = 4.8 Hz), 4.58 (s, 2H), 5.25 (s, 2H), 6.96 (d, 1H, J = 7.5 Hz), 7.29-7.53 (m, 11H), 7.68 (dd, 1H, J = 8.6, 7.5 Hz), 7.88 (d, 1H, J = 8.6 Hz). |
| 1-488 | 1.65-1.85 (m, 4H), 2.11 (s, 3H), 2.54 (t, 2H, J = 7.0 Hz), 3.98 (s, 3H), 4.21 (t, 2H, J = 6.3 Hz), 5.26 (s, 2H), 6.96 (d, 1H, J = 7.5 Hz), 7.28 (s, 1H), 7.34-7.53 (m, 5H), 7.68 (dd, 1H, J = 8.2, 7.5 Hz), 7.89 (d, 1H, J = 8.2 Hz). |
| 1-491 | 1.82-1.98 (m, 4H), 2.59 (s, 3H), 2.67-2.83 (m, 2H), 3.98 (s, 3H), 4.24 (t, 2H, J = 5.8 Hz), 5.26 (s, 2H), 6.96 (d, 1H, J = 7.5 Hz), 7.35-7.53 (m, 6H), 7.69 (dd, 1H, J = 8.4, 7.5 Hz), 7.88 (d, 1H, J = 8.4 Hz). |

TABLE 5-continued

| No | NMR Data |
|---|---|
| 2-68 | 1.53 (s, 6H), 2.42 (s, 3H), 3.89 (s, 3H), 5.18 (s, 2H), 7.33-7.51 (m, 5H), 8.26 (br-s, 1H) |
| 2-82 | 1.55 (s, 9H), 3.97 (s, 3H), 5.32 (s, 2H), 7.35-7.52 (m, 5H), 8.69 (brs, 1H). |
| 2-94 | 1.55 (s, 9H), 3.89 (s, 3H), 5.29 (s, 2H), 7.33-7.49 (m, 10H), 8.67 (br-s, 1H). |
| 2-399 | 2.00 (tt, 2H), 2.16 (s, 3H), 2.49 (t, 2H), 2.59 (t, 2H), 3.95 (s, 3H), 5.25 (s, 2H), 6.91 (s, 1H), 7.34-7.52 (m, 5H), 9.25 (br-s, 1H) |

Each of the tetrazoyloxime derivatives represented by formula (1) or salts thereof (hereinafter referred to as the "compound of the present invention") has excellent fungicidal activity against wide range of fungi belonging to, for example, Oomycetes, Ascomycetes, Deuteromycetes and Basidiomycetes. Therefore, the composition containing the compound of the present invention as the active ingredient can be used for controlling various plant diseases infesting on agricultural and horticultural crops including ornamental flowers, lawns and forage crops by means of seed treatment, foliage application, soil application, or water surface application.

For example, it is possible to use the composition containing the compound of the present invention for controlling plant diseases shown below.

Sugar beet: Cercospora leaf spot (*Cercospora beticola*)
 Aphanomyces root rot (*Aphanomyces cochlioides*)
Peanut: Brown leaf spot (*Mycosphaerella arachidis*)
 Leaf spot (*Mycosphaerella berkeleyi*)
Cucumber: Powdery mildew (*Sphaerotheca fuliginea*)
 Gummy stem blight (*Mycosphaerella melonis*)
 Stem rot (*Sclerotinia sclerotiorum*)
 Gray mold (*Botrytis cinerea*)
 Scab (*Cladosporium cucumerinum*)
 Downy mildew (*Pseudoperonospora cubensis*)
Tomato: Gray mold (*Botrytis cinerea*)
 Leaf mold (*Cladosporium fulvum*)
 Cottony leak (*Pythium aphanidermatum*)
 Late blight (*Phytophthora infestans*)
Eggplant: Gray mold (*Botrytis cinerea*)
 Black rot (*Corynespora melongeneae*)
 Powdery mildew (*Erysiphe cichoracearum*)
Spinach Damping-off (*Pythium ultimum*)
Strawberry:
 Gray mold (*Botrytis cinerea*)
 Powdery mildew (*Sphaerotheca aphanis*)
Onion: Gray-mold neck rot (*Botrytis allii*)
 Gray-mold (*Botrytis cinerea*)
Kidney bean:
 Stem rot (*Sclerotinia sclerotiorum*)
 Gray mold (*Botrytis cinerea*)
Apple: Powdery mildew (*Podosphaera leucotricha*)
 Scab (*Venturia inaequalis*)
 Blossom blight (*Monilinia mali*)
Persimon:
 Powdery mildew (*Phyllactinia kakicola*)
 Anthracnose (*Gloeosporium kaki*)
 Angular leaf spot (*Cercospora kaki*)
Peach & Chemy:
 Brown rot (*Monilinia fructicola*)
Grape: Gray mold (*Botrytis cinerea*)
 Powdery mildew (*Uncinula necator*)
 Ripe rot (*Glomerella cingulata*)
 Downy mildew (*Plasmopara viticola*)
Pear: Scab (*Venturia nashicola*)
 Rust (*Gymnosporangium asiaticum*)
 Black spot (*Alternaria kikuchiana*)
Tea: Gray blight (*Pestalotia theae*)
 Anthracnose (*Colletotrichum theae-sinensis*)
Citrus: Scab (*Elsinoe fawcetti*)
 Blue mold (*Penicillium italicum*)
 Common green mold (*Penicillium digitatum*)
 Gray mold (*Botrytis cinerea*)
Barley: Powdery mildew (*Erysiphe graminis* f. sp. *hordei*)
 Loose smut (*Ustilago nuda*)
Wheat: Scab (*Gibberella zeae*)
 Leaf rust (*Puccinia recondita*)
 Spot blotch (*Cochliobolus sativus*)
  Glume blotch (*Leptosohaeria nodorum*)
 Eye spot (*Pseudocercosporella herpotrichoides*)
 Powdery mildew (*Erysiphe graminis* f. sp. *tritici*)
 Snow mold (*Micronectriella nivalis*)
 Browning root rot (*Pythium iwayamai*)
Rice:
 Blast (*Pyricularia oryzae*)
 Sheath blight (*Rhizoctonia solani*)
 Bakanae disease (*Gibberella fujikuroi*)
 Brown spot (*Cochliobolus miyabeanus*)
 Seeding blight (*Pythiym graminicolum*)
Soybean: Purple speck of seed (*Cercospora kikuchii*)
 Downy mildew (*Peronospora manshurica*) Phytophthora root rot (*Phytophthora sojae*)
Potato: Late blight (*Phytophthora infestans*)
Cruciferous plants:
 Clubroot (*Plasmodiophora brassicae*)
Tobacco: Stem rot (*Sclerotinia sclerotiorum*)
 Powdery mildew (*Erysiphe cichoracearum*)
Tulip: Gray mold (*Botrytis cinerea*)
Bent grass: *Sclerotinia* snow blight (*Sclerotinia borealis*)
 *Pythium* red blight (*Pythium aphanidermatum*)
Orchard grass:
 Powdery mildew (*Erysiphe graminis*)

Besides, in recent years, various plant pathogenic fungi have developed resistance to phenylamide fungicides and strobilurin fungicides. It follows that there is a problem in the control of such a problematic plant disease, because no fungicide can control those plant diseases sufficiently. Therefore, an effective fungicide, which can control such fungi being resistant against those problematic plant diseases is desired. The compounds of the present invention are effective to those resistant strains of fungi to aforementioned fungicides as well as susceptible ones.

For example, the compounds of the present invention are also effective to those resistant strains of fungi to Late blight of potato and tomato (*Phytophthora infestans*), Downy mildew of cucumber (*Pseudoperonospora cubensis*) and Downy mildew of grape (*Plasmopara viticola*) which show resistance to metalaxyl, as well as susceptible ones.

Furthermore, the compounds of the present invention are also effective to Downy mildew of cucumber (*Pseudoperono-*

*spora cubensis*) and Downy mildew of grape (*Plasmopara viticola*) which show resistance to strobilurin fungicides (for example, kresoxim-methyl, azoxystrobin, etc.) similar to susceptible fungi.

Examples of preferred plant injury to which the compounds of the present invention are applied include various plant injuries caused by Oomycetes such as Downy mildew of grape (*Plasmopara viticola*), Downy mildew of gourds (*Pseudoperonospora cubensis*), Late blight of potato and tomato (*Phytophthora infestans*), *Pythium* disease of the grass (*Pythium aphanidermatum*, etc.) and Black root of sugar beet (*Aphanomyces cochlloides*).

Further, the compounds of the present invention can be used also as an antifouling agent which prevents water-dwelling organisms from adhering to structures placed in water such as the outer bottom of a vessel and fishing net.

Moreover, the intermediate chemical compounds of the chemical compounds of the present invention may have fungicidal activities.

Also, the compounds of the present invention can be contained in paints and fibers and thereby used as an antimicrobial and antifungal agent for walls, bathtubs, shoes and clothes.

2) Plant Disease Controlling Agent

The second aspect of the present invention is directed to a plant disease controlling agent containing the compound of the present invention as an active ingredient.

The plant disease controlling agent of the present invention can be used in the state of the compounds of the present invention alone without the addition of other ingredients or, for the use as agricultural chemicals, the compound can be applied in forms of general formulations for agricultural chemicals, such as wettable powders, granules, powders, emulsifiable concentrates, aqueous solutions, suspensions and flowables.

For the additives and carriers to be used in the plant disease controlling agent of the present invention, vegetable powders such as soybean powder and wheat powder, mineral fine powders such as diatomaceous earth, apatite, gypsum, talc, bentonite, pyrophyllite and clay, and organic and inorganic compounds such as sodium benzoate, urea and salt cake can be used, when the compounds are formulated into solid formulations.

When the compounds are formulated into liquid formulations, petroleum fractions such as kerosine, xylene and solvent naphtha, cyclohexane, cyclohexanone, dimethylformamide, dimethylsulfoxide, alcohol, acetone, trichloroethylene, methylisobutylketone, mineral oil, vegetable oil and water, can be used as the solvent.

In the plant disease controlling agent of the present invention, surfactants may be added to the formulations in order to make the formulations homogeneous and stable, if appropriate.

Examples of the surfactants include nonionic surfactants such as alkyl phenyl ether added with polyoxyethylene, alkyl ether added with polyoxyethylene, higher fatty acid ester added with polyoxyethylene, sorbitan higher fatty acid ester added with polyoxyethylene, tristyrylphenyl ether added with polyoxyethylene; sulfuric ester salt of alkyl phenyl ether added with polyoxyethylene, alkylbenzene sulfonate salt, sulfuric ester salt of higher alcohol, alkylnaphthalene sulfonate salt, polycarboxylate salt, lignin sulfonate salt, formaldehyde condensate of alkylnaphthalene sulfonate, and copolymer of isobutylene-maleic anhydride.

In general, the content of an active ingredient in the formulations is within a range from 0.5 to 95% by weight, and preferably from 2 to 70% by weight, based on the total weight of the composition (formulation).

When the plant disease controlling agent of the present invention is in the form of wettable powders, emulsifiable concentrates and flowable formulations, it can be applied in a form prepared by diluting the formulations with water to the suspension or the emulsion at a desired concentrations, while the powders and the granules of the said compound can be directly dispersed to plants.

Needless to say that the compound of the present invention or the plant disease controlling agent of the present invention alone has sufficient fungicidal activity, however, it can be used in combination with one kind, two kinds, or more of various types of fungicides, insecticides, acaricides and synergists.

Typical examples for the fungicides, insecticides, acaricides and plant growth regulators, those which are usable in admixing with the compounds of the present invention or the plant disease controlling agent of the present invention, are shown below.

Fungicides:

Copper agents: basic copper chloride, basic copper sulfate

Sulfur agents: thiuram, zineb, maneb, mancozeb, ziram, propineb, polycarbamate, etc.

Polyhaloalkylthio agents: captan, folpet, dichlorofluanid, etc.

Organic chlorine agents: chlorothalonil, fthalide, etc.

Organic phosphorous agents: IBP, EDDP, trichlophosm-ethyl, pyrazophos, fosetyl, etc.

Benzimidazole agents: thiophanate-methyl, benomyl, carbendazim, thiabendazole, etc.

Dicarboxylmide agents: iprodione, procymidone, vinclozolin, fluoroimide, etc.

Carboxyamide agents: oxycarboxin, mepronil, flutolanil, tecloftalam, trichlamide, pencycuron, etc.

Acylalanine agents: metalaxyl, oxadixyl, furalaxyl, etc.

Strobilurin-based agents: azoxystrobin, kresoxim-methyl, pyraclostrobin, trifloxystrobin, pyribencarb, famoxadone, fenamidone, etc.

Anilinopyrimidine agents: andoprin, mepanipyrim, pyrimethanil, diprozinil, etc.

SBI agents: triadimefon, triadimenol, bitertanol, myclobutanil, hexaconazole, propiconazole, triflumizole, prochloraz, pefurazoate, fenarimol, pyrifenox, triforine, flusilazole, etaconazole, dichlobutorazol, fluotrimazole, flutriafen, penconazole, diniconazole, imazalil, tridemorph, fenpropimorph, buthiobate, epoxiconazole, metoconazole, prothioconazole, spiroxamine, fenhexamid, pyributycarb, etc.

Antibiotic agents: polyoxins, blasticidin-S, kasugamycin, validamycin, dihydrostreptomycin sulfate, etc.

Anilide-based agents: boscalid, penthiopyrad, fluopyram, bixafen, etc.

Guanidine-based agents: iminoctadine acetate salt, iminoctadine albesilate salt, dodine, guazatine, etc.

Valine-based agents: dimethomorph, flumorph, iprovalicarb, benthiavalicarb, mandipropamid, etc.

Others: cymoxanil, cyazofamid, amisulbrom, propamocarb, fluazinam, propamocarb acetate salt, ethaboxam, fluopicolide, zoxamide, cyflufenamid, metrafenone, proquinazid, hydroxy isoxazole, metasulfocarb, anilazine, isoprothiolane, ferimzone, probenazole, tiadinil, acibenzolar s-methyl, isotianil, pyroquilon, phthalide, tricyclazole, carpropamid, fenoxanil, diclocymet, fluazinam, fludioxonil, pyrrolenitrine, hydroxyl isoxazole, flusulfamide, diethofencarb, quintozene, metasulfocarb, anilazine, quinomethionate, dithianon, dinocap, dichlomezine, oxolinic acid, lecithin, sodium bicarbonate, fenaminosulf, phenazine oxide, etc.

Insecticides/Acaricides:

Organic phosphorous and carbamate-based insecticides: fenthion, fenitrothion, diazinon, chlorpyrifos, ESP, vamidothion, phenthoate, dimethoate, formothion, malathion, trichlorfon, thiometon, phosmet, dichlorvos, acephate, EPBP, methyl parathion, oxydemeton-methyl, ethion, salithion, cyanophos, isoxathion, pyridafenthion, phosalone, methidathion, sulprofos, chlorfenvinphos, tetrachlorvinphos, dimethylvinphos, propaphos, isofenphos, ethylthiometon, profenofos, pyraclofos, monocrotophos, azinphos-methyl, aldicarb, methomyl, thiodicarb, carbofuran, carbosulfan, benfuracarb, furathiocarb, propoxur, BPMC, MTMC, MIPC, carbaryl, pirimicarb, ethiophencarb, fenoxycarb, etc.

Pyrethroid-based insecticides: permethrin, cypermethrin, deltamethrin, fenvalerate, fenpropathrin, pyrethrins, allethrin, tetramethrin, resmethrin, dimethrin, propathrin, phenothrin, prothrin, fluvalinate, cyfluthrin, cyhalothrin, flucythrinate, etofenprox, cycloprothrin, tralomethrin, silafluofen, Halfenprox, acrinathrin, etc.

Benzoylurea-based and other insecticides: diflubenzuron, chlorfluazuron, hexaflumuron, triflumuron, tetrabenzuron, flufenoxuron, flucycloxuron, buprofezin, pyriproxyfen, methoprene, benzoepin, diafenthiuron, acetamiprid, imidacloprid, nitenpyram, fipronil, cartap, thiocyclam, bensultap, nicotine sulfate, rotenone, metaldehyde, emamectin, flubendiamide, spinosad, machine oil, BT, insect pathogen viruses and other microbial agricultural chemicals, etc.

Nematicides: phenamiphos, fosthiazate, etc.

Acaricides: chlorobenzilate, phenisobromolate, dicofol, amitraz, BPPS, benzomate, hexathiazox, fenbutatin oxide, polynactin, quinomethionate, CPCBS, tetradifon, abamectin, milbemectin, clofentezine, cyhexatin, pyridaben, fenpyroximate, tebufenpyrad, pyrimidifen, fenothiocarb, dienochlor, fluacrypyrim, etc.

Plant Growth Regulators: gibberellins (e.g., gibberellin A3, gibberellin A4, gibberellin A7, etc.), IAA, NAA, etc.

EXAMPLES

The present invention will be explained in more detail by way of Examples, but the present invention should not be interpreted to be limited to these Examples.

Preparation Example (Step 1)

A mixture of 2.94 g (11.4 mmol) of diethyl 4-chloro-2,6-pyridine dicarboxylate and 20 mL of ethanol was heated to 55° C. and an aqueous solution prepared from 0.27 g (6.8 mmol) of sodium hydroxide and 50 mL of water was added dropwise to the mixture for 8 hours. After completion of the dropwise addition, the mixed solution was stirred for one hour and allowed to stand overnight at room temperature. After the solvent was removed under reduced pressure, the residue was back-extracted with water/ethyl acetate. The organic layer was washed with water and the aqueous layers were combined. Then concentrated hydrochloric acid was added to the aqueous layer thereby adjusting the pH to 2.5. The aqueous layer was extracted with ethyl acetate, washed with saturated brine and then dried over anhydrous magnesium sulfate. The solvent was removed under reduced pressure to obtain 1.42 g (6.2 mmol, yield of 54%) of monoethyl 4-chloro-2,6-pyridine dicarboxylate.

(Step 2)

To a mixture of 1.42 g (6.2 mmol) of monoethyl 4-chloro-2,6-pyridine dicarboxylate, 12 mL of anhydrous tetrahydrofuran and 0.69 g (6.8 mmol) of triethylamine, 1.87 g (6.8 mmol) of diphenyl phosphoryl azide was added at room temperature, followed by heating to 60° C. and further stirring for one hour.

To the reaction mixture, 0.93 g (12.6 mmol) of t-butanol was added, followed by further stirring at 60° C. for 18 hours. The reaction solution was added to water, followed by extraction with ethyl acetate. The organic layer was washed with saturated brine and dried over anhydrous magnesium sulfate, and then the solvent was removed under reduced pressure. The residue was purified by silica gel column chromatography (eluent: n-hexane/ethyl acetate=5/1 (v/v)) to obtain 1.00 g (3.3 mmol, yield of 54%) of ethyl 2-(t-butoxycarbonyl)amino-4-chloropicolinate.

(Step 3)

To a mixture of 1.00 g (3.3 mmol) of ethyl 2-(t-butoxycarbonyl)amino-4-chloropicolinate and 20 mL of anhydrous ethanol, 0.38 g (10.0 mmol) of sodium borohydride was added, followed by stirring at room temperature for 17 hours. To the reaction solution, dilute hydrochloric acid was added thereby adjusting the pH to 2 and the solution was neutralized by adding saturated sodium bicarbonate aqueous solution. After ethanol was removed under reduced pressure, the resultant was extracted with ethyl acetate and dried over anhydrous magnesium sulfate. The solvent was removed under reduced pressure and the resultant residue was purified by silica gel column chromatography (eluent: n-hexane/ethyl acetate=3/1 (v/v)) to obtain 0.75 g (2.9 mmol, yield of 87%) of 2-(t-butoxycarbonyl)amino-4-chloro-6-hydroxymethylpyridine.

To a mixture of 0.74 g (2.9 mmol) of 2-(t-butoxycarbonyl)amino-4-chloro-6-hydroxymethylpyridine and 20 mL of dichloromethane 20 mL, 0.29 g (3.7 mmol) of pyridine was added, and 0.41 g (3.5 mmol) of thionyl chloride was further added, followed by stirring at room temperature for 3.5 hours. The reaction solution was added to water and saturated sodium bicarbonate aqueous solution was added thereby adjusting the pH to 6, followed by extraction with chloroform. The organic layer was dried over anhydrous magnesium sulfate and the solvent was removed under reduced pressure. The resultant residue was purified by silica gel column chromatography (eluent: n-hexane/ethyl acetate=9/1 (v/v)) to obtain 0.56 g (2.0 mmol, yield of 71%) of 2-(t-butoxycarbonyl)amino-4-chloro-6-chloromethylpyridine.

(Step 5)

A mixture of 5 mL of dry N,N-dimethylformamide and 0.12 g (0.6 mmol) of (Z)-(1-methyl-1H-tetrazol-5-yl)phenylmethanone oxime was cooled in an ice bath and 0.03 g (60% in oil, 0.75 mmol) of sodium hydride was added to the solution. After the suspension was stirred for 5 minutes, a mixture of 0.19 g (0.69 mmol) of 2-(t-butoxycarbonyl)amino-4-chloro-6-chloromethylpyridine and 5 mL of N,N-dimethylformamide was added, followed by stirring at room temperature for 3 hours.

The reaction mixture was added to an aqueous saturated ammonium chloride solution and then extracted with ethyl acetate. The organic layer was dried over anhydrous magnesium sulfate and the solvent was removed under reduced pressure. The resultant residue was purified by silica gel column chromatography (eluent: n-hexane/ethyl acetate=4/1 (v/v)) to obtain 0.16 g (0.3 mmol, yield of 62%) of (Z)-(1-methyl-1H-tetrazol-5-yl)phenylmethanone-O-[2-(t-butoxycarbonyl)amino-4-chloropyridin-6-ylmethyl]-oxime (compound of a compound number 1-275 in Table 1)

Although several Formulation Examples of the plant disease controlling agent of the present invention are shown below, additives and the additive ratio should not be limited thereto and can be broadly changed. Parts shown in the Formulation Examples are by weight.

Formulation Example 1

Wettable Powders

| Compound of the present invention | 40 parts |
|---|---|
| Clay | 53 parts |
| Sodium dioctyl sulfosuccinate | 4 parts |
| Sodium lignin sulfonate | 3 parts |

The above components are uniformly mixed and finely ground to obtain wettable powders containing 40% of an active ingredient.

Formulation Example 2

Emulsifiable Concentrates

| Compound of the present invention | 10 parts |
|---|---|
| Sorbesso 200 | 53 parts |
| Cyclohexanone | 26 parts |
| Calcium dodecylbenzene sulfonate | 1 part |
| Polyoxyethylene alkyl allyl ether | 10 parts |

The above components are mixed and dissolved to obtain emulsifiable concentrates containing 10% of an active ingredient.

Formulation Example 3

Powders

| Compound of the present invention | 10 parts |
|---|---|
| Clay | 90 parts |

The above components are uniformly mixed and finely ground to obtain powders containing 10% of an active ingredient.

Formulation Example 4

Granules

| Compound of the present invention | 5 parts |
|---|---|
| Clay | 73 parts |
| Bentonite | 20 parts |
| Sodium dioctyl sulfosuccinate | 1 part |
| Potassium phosphate | 1 part |

The above components are well ground and mixed, well kneaded with water, granulated and then dried to obtain granules containing 5% of an active ingredient.

Formulation Example 5

Suspensions

| Compound of the present invention | 10 parts |
|---|---|
| Polyoxyethylene alkyl allyl ether | 4 parts |
| Sodium polycarboxylate | 2 parts |
| Glycerin | 10 parts |
| Xanthan gum | 0.2 part |
| Water | 73.8 parts |

The above components are mixed, and ground by wet grinding to a particle size of 3 micron or less to obtain suspensions containing 10% of an active ingredient.

Formulation Example 6

Granular Wettable Powders

| Compound of the present invention | 40 parts |
|---|---|
| Clay | 36 parts |
| Potassium chloride | 10 parts |
| Sodium alkylbenzene sulfonate | 1 part |
| Sodium lignin sulfonate | 8 parts |
| Formaldehyde condensate of sodium alkylbenzene sulfonate | 5 parts |

The above components are uniformly mixed and finely ground and then kneaded with an appropriate amount of water to form a clay-like substance. The clay-like substance is granulated and then dried to obtain granular wettable powders containing 40% of an active ingredient.

Test Example

Tomato Late Blight Control Test

An emulsifiable concentrate of Formulation Example 2 was sprayed over the tomato seedling (cultivar: "Regina", 4-5 leaves stage) grown in an unglazed pot, at the concentration of an active ingredient of 100 ppm. After spraying, the tomato seedling was air-dried at room temperature and a zoosporangium suspension of tomato phytophthora (Phytophthora infestans) was spray-inoculated, and then the tomato seedling was retained in a high-humidity thermostatic chamber (20° C.) maintained at a light or dark state every 12 hours for 4 days. The state of appearance of lesions on leaves was examined and compared with the non-treated tomato seedling and thus the control effect was determined. As a result, the compounds shown below exhibited a preventive value of 80%. The compound numbers correspond to the compound numbers in Table 1.

Compound numbers: 1-17, 1-68 to 1-82, 1-84 to 1-87, 1-131, 1-197, 1-275 to 1-278, 1-323, 1-377, 1-380, 1-399, 1-400, 1-405 to 1-407, 1-415, 1-418, 1-420 to 1-424, 1-429 to 1-431, 1-435, 1-445 to 1-450, 1-452 to 1-460, 1-464, 1-467 to 1-479, 1-481, 1-486, 1-488, and 1-491

INDUSTRIAL APPLICABILITY

The present invention provides a tetrazoyloxime derivative or a salt thereof, which is excellent in a control effect against plant disease injury, and a plant disease controlling agent containing the same as an active ingredient, and is therefore industrially quite useful.

The invention claimed is:

1. A tetrazoyloxime derivative represented by formula (1):

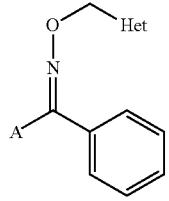

(1)

wherein
A represents a tetrazoyl group represented by formula (2):

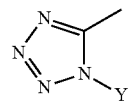

(2)

in which Y represents a $C_{1-8}$ alkyl group; and
Het represents a pyridyl group represented by formula (4):

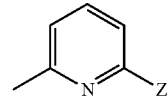

(4)

in which
Z represents a group represented by formula: $Q^1C(=O)NH-$ (in which $Q^1$ represents a $C_{5-6}$ alkenyloxy group, or a $C_{4-7}$ alkynyloxy group), or a salt thereof.

2. The tetrazoyloxime derivative according to claim 1, wherein Y is a methyl group, or a salt thereof.

* * * * *